US006113912A

United States Patent [19]
Funkhouser et al.

[11] Patent Number: 6,113,912
[45] Date of Patent: Sep. 5, 2000

[54] HEPATITIS A VIRUS VACCINES

[75] Inventors: Ann W. Funkhouser, Ellicott City; Suzanne U. Emerson, Rockville; Robert H. Purcell, Boyds, all of Md.; Eric D'Hondt, Ottenburg, Belgium

[73] Assignee: The United States of America as represented by the Department of Health and Human Services, Washington, D.C.

[21] Appl. No.: 08/475,886

[22] Filed: Jun. 7, 1995

Related U.S. Application Data

[63] Continuation-in-part of application No. 08/397,232, filed as application No. PCT/US93/08610, Sep. 17, 1993, which is a continuation-in-part of application No. 08/947,338, Sep. 18, 1992, abandoned.

[51] Int. Cl.[7] ........................... H61K 39/29; C12N 7/00; C12N 7/01

[52] U.S. Cl. .................... 424/226.1; 424/93.1; 424/93.6; 435/235.1; 435/236.1; 435/237; 435/172.3; 435/320.1

[58] Field of Search ................................ 435/235.1, 236, 435/237, 172.3; 424/93.1, 93.6, 226.1

[56] References Cited

U.S. PATENT DOCUMENTS

| | | | |
|---|---|---|---|
| 4,532,215 | 7/1985 | Daemer et al. . | |
| 4,620,978 | 11/1986 | Daemer et al. . | |
| 4,636,469 | 1/1987 | Daemer et al. . | |
| 4,783,407 | 11/1988 | Provost et al. . | |
| 4,894,228 | 1/1990 | Purcell et al. ........................... | 424/89 |

FOREIGN PATENT DOCUMENTS

| | | |
|---|---|---|
| 0323900 | 7/1989 | European Pat. Off. . |
| 2398504 | 3/1979 | France . |
| WOA9219268 | 11/1992 | WIPO . |
| WO93/09139 | 5/1993 | WIPO . |

OTHER PUBLICATIONS

Emerson et al., J. Virol. 66(2):650–654, Feb. 1992.
Provost et al. J. Med. Virol. 34(4):227–231, 1991.
Fineschi et al. J. Hepatol. 13(4):S146–S151, Apr. 1991.
Karron et al. J. Infect. Dis. 157(2):338–345, Feb. 1988.

Day et al., "A Single Base Mutation in the 5' Noncoding Region of HAV Enhances Replication of Virus In Vitro", *Vaccines 90. Modern Approaches to New Vaccines Including Prevention of Aids,* pp. 175–178 (1990).

Ross et al., "Molecular Cloning of cDNA From Hepatitis A Virus Strain HM–175 After Multiple Passages In Vivo and In Vitro", *J. Med. Virol.,* vol. 67, pp. 1741–1744 (1986).

Najarian et al., "Primary Structure and Gene Organization Of Human Hepatitis A Virus", *Proc. Nat'l. Acad. Sci. USA,* vol. 82 pp. 2627–2631 (1985).

B. Ross et al, "Nucleotide Sequence of High–Passage Hepatitis A Virus Strain HM175: Comparison with Wild–type and Cell Culture–adapted Strains", *J. Gen. Virol.,* 70:2805–2810 (Oct., 1989).

R. Jansen et al, "Complete Nucleotide Sequence of a Cell Culture–Adapted Variant of Hepatitis A Virus: Comparison with Wild–Type Virus with Restricted Capacity for in Vitro Replication", *Virol.,* 163:299–307 (1988).

V. Tedeschi et al, "Partial Characterzation of Hepatitis A Viruses from Three Intermediate Passage Levels of a Series Resulting in Adaptation to Growth in Cell Culture and Attenuation of Virulence", *J. Med., Virol.,* 39(1):16–21 (Jan. 1993).

N. Fineschi et al, "Characterization of a Hepatitis A Virus Strain Suitable for Vaccine Production", *J. Hepatol.,* 13(4):S146–S151 (Apr., 1991).

P. Provost et al, "New Findings in Live, Attenuated Hepatitis A Vaccine Development", *J. Med. Virol.,* 20:165–175 (1986) [Provost].

K. Midthun et al, "Safety and Immunogenicity of a Live Attenuated Hepatitis A Virus Vaccine in Seronegative Volunteers", *J. Infect. Dis.,* 163:735–739 (Apr., 1991).

J. Mao et al, "Primary Study of Attenuated Live Hepatitis A Vaccine (H2 Strain) in Humans", *J. Infect. Dis.,* 159(4):621–624 (Apr., 1989).

I. Gust et al, "The Origin of the HM175 Strain of Hepatitis A Virus", *J. Infect. Dis.,* 151(2):365–366 (Feb., 1985).

F. Andre et al, "Inactivated Candidate Vaccines for Hepatitis A", *Prog. Med. Virol. Basel, Karger,* 37:72–95 (1990).

R. Daemer et al, "Propagation of Human Hepatitis A Virus in African Green Monkey Kidney Cell Culture: Primary Isolation and Serial Passage", *Infect. Immun.,* 32:388–393 (Apr., 1981).

J. Melnick, "New Picornavirus Vaccines for Hepatitis A, and Lessons from the Control of Poliomyelitis by the Prototype Picornavirus Vaccines", *Prog. Med. Virol. Basel, Karger,* 37:47–55 (1990).

R. Karron et al, "Studies of Prototype Live Hepatitis A Virus Vaccines in Primate Models", *J. Infect. Dis.,* 157(2):338–345 (Feb., 1988).

S. Emerson et al, "Mutations Responsible for Adaptation of Hepatitis A Virus to Efficient Growth in Cell Culture", *J. Virol.,* 65(9):4882–4886 (Sep., 1991).

J. Cohen et al, "Complete Nucleotide Sequence of Wild–Type Hepatitis A Virus: Comparison with Different Strains of Hepatitis A Virus and Other Picornaviruses", *J. Virol.,* 61(1):50–59 (Jan., 1987) [Cohen I].

J. Cohen et al, "Complete Nucleotide Sequence of an Attenuated Hepatitis A Virus: Comparison with Wild–Type Virus", *Proc. Natl. Acad. Sci. USA,* 84(8):2497–2501 (Apr., 1987) [Cohen II].

(List continued on next page.)

*Primary Examiner*—Michael P. Woodward
*Assistant Examiner*—Mary K Zeman
*Attorney, Agent, or Firm*—Morgan & Finnegan, L.L.P.

[57] ABSTRACT

A live hepatitis A virus adapted to growth in MRC-5 cells, which HAV is preferably characterized by suitable attenuation for effective vaccine administration to humans and animals without inactivation, methods for adapting HAV to growth in MRC-5, vaccine compositions and method of vaccinating humans against HAV infection.

5 Claims, 17 Drawing Sheets

OTHER PUBLICATIONS

S. Lemon et al, "Serum Neutralizing Antibody Response to Hepatitis A Virus", *J. Infect. Dis.,* 148(6):1033–1039 (Dec., 1983).

R. Purcelle et al, "A Microtiter Solid–Phase Radioimmunoassay for Hepatitis A Antigen and Antibody",*J. Immunol.,* 116(2):349–356 (Feb., 1976).

J. Ticehurst et al, "Detection of Hepatitis A Virus by Extraction of Viral RNA and Molecular Hybridization", *J. Clin. Microbiol.,* 25(10):1822–1829 (Oct., 1987).

J. Cohen et al, "Hepatitis A Virus cDNA and its RNA Transcripts are Infectious in Cell Culture", *J. Virol.,* 61(10):3035–3039 (Oct., 1987) [Cohen III].

P. Provost et al, "Further Evaluation of a Live Hepatitis A Vaccine in Marmosets", *J. Med. Virol.,* 34(4):227–231 (Aug., 1991) [Provost II].

B. Robertson et al, "Genetic Relatedness of Hepatitis A Virus Strains Recovered from Different Geographical Regions", *J. Gen. Virol.,* 73:1365–1377 (May, 1992).

J. Graff et al, "Nucleotide Sequence of Wild–Type Hepatitis A Virus GBM in Comparison with Two Cell Culture–Adapted Variants", *J. Virol.,* 68(1):548–554 (Jan., 1994).

F. Andre, "Approaches to a Vaccine Against Hepatitis A: Development and Manufacture of an Inactivated Vaccine", *J. Infect. Dis.,* 171(Suppl 1):S33–S39 (Mar., 1995).

J. Peetermans, "Production, Quality Control and Characterization of an Inactivated Hepatitis A Vaccine", *Vaccine,* 10(Suppl 1):S99–S101 (Nov., 1992).

F. Andre, "Hepatitis A in Travellers: Development of a Safe, Immunogenic and Efficacious Inactivated Vaccine", *Travel Medicine International,* 13(1):10–14 (Jan., 1995).

Product Insert, "HA:L3A Prescribing Information, Hepatitis A Vaccine, Inactivated Havrix", distributed by SmithKline Beecham Pharmaceuticals (Feb., 1995).

Emerson et al., J. Virol., 66(2):650–654, Feb. 1992.

Provost et al., J. Med. Virol., 34(4):227–231, 1991 (Ref. B.S.).

Kineschi et al., J. Hepatol., 13(4):S146–S151, Apr. 1991 (Ref A.U.).

Karron et al., J. Infect. Dis., 157(2):338–345, Feb. 1988, (Ref. AAT).

```
TTCAAGAGGG GTCTCCGGGA ATTTCCGGAG TCCCTCTTGG AAGTCCATGG TGAGGGGACT  60

TGATACCTCA CCGCCGTTTG CCTAGGCTAT AGGCTAAATT TTCCCTTTCC CTTTTCCCTT 120
    C         ----                    G
TCCTATTCCC TTTGTTTTGC TTGTAAATAT TAATTCCTGC AGGTTCAGGG TTCTTAAATC 180
                          -
TGTTTCTCTA TAAGAACACT CATTTTTCAC GCTTTCTGTC TTCTTTCTTC CAGGGCTCTC 240

CCCTTGCCCT AGGCTCTGGC CGTTGCGCCC GGCGGGGTCA ACTCCATGAT AGCATGGAG  300

CTGTAGGAGT CTAAATTGGG GACACAGATG TTTGGAACGT CACCTTGCAG TGTTAACTTG 360

GCTTTCATGA ATCTCTTTGA TCTTCCACAA GGGGTAGGCT ACGGGTGAAA CCTCTTAGGC 420

TAATACTTCT ATGAAGAGAT GCCTTGGATA GGGTAACAGC GGCGGATATT GGTGAGTTGT 480

TAAGACAAAA ACCATTCAAC GCCGGAGGAC TGACTCTCAT CCAGTGGATG CATTGAGTGG 540

ATTGACTGTC AGGGCTGTCT TTAGGCTTAA TTCCAGACCT CTCTGTGCTT AGGGCAAACA 600

TCATTTGGCC TTAAATGGGA TTCTGTGAGA GGGGATCCCT CCATTGACAG CTGGACTGTT 660

CTTTGGGGCC TTATGTGGTG TTTGCCTCTG AGGTACTCAG GGGCATTTAG GTTTTTCCTC 720
```

| | | | | | | | | | | | | | | |
|---|---|---|---|---|---|---|---|---|---|---|---|---|---|---|
| ATTCTTAAAT | AATA | ATG | AAC | ATG | TCT | AGA | CAA | GGT | ATT | TTC | CAG | ACT | GTT | 770 |
| | | Met | Asn | Met | Ser | Arg | Gln | Gly | Ile | Phe | Gln | Thr | Val | |
| | | 1 | | | 5 | | | | | 10 | | | | |

| | | | | | | | | | | | | | | |
|---|---|---|---|---|---|---|---|---|---|---|---|---|---|---|
| GGG | AGT | GGT | CTT | GAC | CAC | ATC | CTG | TCT | TTG | GCA | GAC | ATT | GAG | GAA GAG 818 |
| Gly | Ser | Gly | Leu | Asp | His | Ile | Leu | Ser | Leu | Ala | Asp | Ile | Glu | Glu Glu |
| | | 15 | | | | 20 | | | | 25 | | | | |

| | | | | | | | | | | | | | | |
|---|---|---|---|---|---|---|---|---|---|---|---|---|---|---|
| CAA | ATG | ATT | CAA | TCA | GTT | GAT | AGG | ACT | GCA | GTG | ACT | GGT | GCT | TCT TAT 866 |
| Gln | Met | Ile | Gln | Ser | Val | Asp | Arg | Thr | Ala | Val | Thr | Gly | Ala | Ser Tyr |
| | 30 | | | | 35 | | | | | 40 | | | | |

| | | | | | | | | | | | | | | |
|---|---|---|---|---|---|---|---|---|---|---|---|---|---|---|
| TTT | ACT | TCT | GTG | GAT | CAA | TCT | TCA | GTT | CAT | ACA | GCT | GAG | GTT | GGA TCA 914 |
| Phe | Thr | Ser | Val | Asp | Gln | Ser | Ser | Val | His | Thr | Ala | Glu | Val | Gly Ser |
| 45 | | | | | 50 | | | | | 55 | | | | 60 |

| | | | | | | | | | | | | | | |
|---|---|---|---|---|---|---|---|---|---|---|---|---|---|---|
| CAC | CAG | GTT | GAA | CCT | TTG | AGA | ACC | TCT | GTT | GAT | AAA | CCC | GGT | TCA AAG 962 |
| His | Gln | Val | Glu | Pro | Leu | Arg | Thr | Ser | Val | Asp | Lys | Pro | Gly | Ser Lys |
| | | | | 65 | | | | 70 | | | | | 75 | |
| G | | | | | | | | | | | | | | |

| | | | | | | | | | | | | | | |
|---|---|---|---|---|---|---|---|---|---|---|---|---|---|---|
| AAG | ACT | CAG | GGA | GAG | AAA | TTT | TTC | TTG | ATT | CAT | TCT | GCA | GAT | TGG CTT 1010 |
| Lys | Thr | Gln | Gly | Glu | Lys | Phe | Phe | Leu | Ile | His | Ser | Ala | Asp | Trp Leu |
| Arg | | | 80 | | | | | 85 | | | | | 90 | |

| | | | | | | | | | | | | | | |
|---|---|---|---|---|---|---|---|---|---|---|---|---|---|---|
| ACT | ACA | CAT | GCT | CTT | TTC | CAT | GAA | GTT | GCA | AAA | TTG | GAT | GTG | GTG AAA 1058 |
| Thr | Thr | His | Ala | Leu | Phe | His | Glu | Val | Ala | Lys | Leu | Asp | Val | Val Lys |
| | | 95 | | | | | 100 | | | | | 105 | | |

| | | | | | | | | | | | | | | |
|---|---|---|---|---|---|---|---|---|---|---|---|---|---|---|
| TTA | TTA | TAC | AAT | GAG | CAG | TTT | GCT | GTT | CAA | GGG | TTG | TTG | AGA | TAC CAT 1106 |
| Leu | Leu | Tyr | Asn | Glu | Gln | Phe | Ala | Val | Gln | Gly | Leu | Leu | Arg | Tyr His |
| | 110 | | | | | 115 | | | | | 120 | | | |

FIG. 6A

| | | | | | | | | | | | | | | | | |
|---|---|---|---|---|---|---|---|---|---|---|---|---|---|---|---|---|
|ACA|TAT|GCA|AGA|TTT|GGC|ATT|GAA|ATT|CAA|GTT|CAG|ATA|AAC|CCT|ACA|1154|
|Thr|Tyr|Ala|Arg|Phe|Gly|Ile|Glu|Ile|Gln|Val|Gln|Ile|Asn|Pro|Thr| |
|125| | | |130| | | |135| | | |140| | | | |

```
ACA TAT GCA AGA TTT GGC ATT GAA ATT CAA GTT CAG ATA AAC CCT ACA   1154
Thr Tyr Ala Arg Phe Gly Ile Glu Ile Gln Val Gln Ile Asn Pro Thr
125             130             135             140

CCT TTC CAA CAG GGG GGA TTG ATC TGT GCT ATG GTT CCT GGT GAC CAG   1202
Pro Phe Gln Gln Gly Gly Leu Ile Cys Ala Met Val Pro Gly Asp Gln
                145             150             155

AGC TAT GGT TCT ATA GCA TCA TTG ACT GTT TAT CCT CAT GGT TTG TTA   1250
Ser Tyr Gly Ser Ile Ala Ser Leu Thr Val Tyr Pro His Gly Leu Leu
                160             165             170

AAT TGC AAT ATT AAC AAT GTG GTT AGA ATA AAG GTT CCA TTT ATT TAC   1298
Asn Cys Asn Ile Asn Asn Val Val Arg Ile Lys Val Pro Phe Ile Tyr
            175             180             185

ACA AGA GGT GCT TAC CAC TTT AAA GAT CCA CAA TAC CCA GTT TGG GAA   1346
Thr Arg Gly Ala Tyr His Phe Lys Asp Pro Gln Tyr Pro Val Trp Glu
        190             195             200

TTG ACA ATT AGA GTT TGG TCA GAA TTA AAT ATT GGG ACA GGA ACT TCA   1394
Leu Thr Ile Arg Val Trp Ser Glu Leu Asn Ile Gly Thr Gly Thr Ser
205             210             215             220

GCT TAT ACT TCA CTC AAT GTT TTA GCT AGA TTT ACA GAT TTG GAG TTG   1442
Ala Tyr Thr Ser Leu Asn Val Leu Ala Arg Phe Thr Asp Leu Glu Leu
                225             230             235

CAT GGA TTA ACT CCT CTT TCT ACA CAA ATG ATG AGA AAT GAA TTT AGG   1490
His Gly Leu Thr Pro Leu Ser Thr Gln Met Met Arg Asn Glu Phe Arg
                240             245             250

GTC AGT ACT ACT GAG AAT GTG GTG AAT CTG TCA AAT TAT GAA GAT GCA   1538
Val Ser Thr Thr Glu Asn Val Val Asn Leu Ser Asn Tyr Glu Asp Ala
            255             260             265

AGA GCA AAG ATG TCT TTT GCT TTG GAT CAG GAA GAT TGG AAA TCT GAT   1586
Arg Ala Lys Met Ser Phe Ala Leu Asp Gln Glu Asp Trp Lys Ser Asp
        270             275             280

CCG TCC CAG GGT GGT GGG ATC AAA ATT ACT CAT TTT ACT ACT TGG ACA   1634
Pro Ser Gln Gly Gly Gly Ile Lys Ile Thr His Phe Thr Thr Trp Thr
285             290             295             300

TCT ATT CCA ACT TTG GCT GCT CAG TTT CCA TTT AAT GCT TCA GAC TCA   1682
Ser Ile Pro Thr Leu Ala Ala Gln Phe Pro Phe Asn Ala Ser Asp Ser
                305             310             315

GTT GGT CAA CAA ATT AAA GTT ATT CCA GTT GAC CCA TAT TTT TTC CAA   1730
Val Gly Gln Gln Ile Lys Val Ile Pro Val Asp Pro Tyr Phe Phe Gln
                320             325             330
                 A
ATG ACA AAT ACG AAT CCT GAC CAA AAA TGT ATA ACT GCT TTG GCT TCT   1778
Met Thr Asn Thr Asn Pro Asp Gln Lys Cys Ile Thr Ala Leu Ala Ser
                335             340             345
```

FIG. 6B

```
ATT TGT CAG ATG TTT TGT TTT TGG AGA GGA GAT CTT GTC TTT GAT TTT    1826
Ile Cys Gln Met Phe Cys Phe Trp Arg Gly Asp Leu Val Phe Asp Phe
    350             355             360

CAA GTT TTT CCC ACC AAA TAT CAT TCA GGT AGA TTA CTG TTT TGT TTT    1874
Gln Val Phe Pro Thr Lys Tyr His Ser Gly Arg Leu Leu Phe Cys Phe
365             370             375             380

GTT CCT GGC AAT GAG CTA ATA GAT GTT TCT GGA ATC ACA TTA AAG CAA    1922
Val Pro Gly Asn Glu Leu Ile Asp Val Ser Gly Ile Thr Leu Lys Gln
                385             390             395

GCA ACT ACT GCT CCT TGT GCA GTA ATG GAT ATT ACA GGA GTG CAG TCA    1970
Ala Thr Thr Ala Pro Cys Ala Val Met Asp Ile Thr Gly Val Gln Ser
            400             405             410

ACT TTG AGA TTT CGT GTT CCC TGG ATT TCT GAC ACT CCT TAC AGA GTG    2018
Thr Leu Arg Phe Arg Val Pro Trp Ile Ser Asp Thr Pro Tyr Arg Val
        415             420             425

AAC AGG TAT ACA AAG TCA GCA CAT CAG AAA GGT GAG TAC ACT GCC ATT    2066
Asn Arg Tyr Thr Lys Ser Ala His Gln Lys Gly Glu Tyr Thr Ala Ile
    430             435             440

GGG AAG CTT ATT GTG TAT TGT TAT AAC AGA TTG ACC TCT CCT TCT AAC    2114
Gly Lys Leu Ile Val Tyr Cys Tyr Asn Arg Leu Thr Ser Pro Ser Asn
445             450             455             460

GTT GCT TCC CAT GTC AGA GTG AAT GTT TAT CTT TCA GCA ATT AAC TTG    2162
Val Ala Ser His Val Arg Val Asn Val Tyr Leu Ser Ala Ile Asn Leu
                465             470             475

GAA TGT TTT GCT CCT CTT TAT CAT GCT ATG GAT GTT ACT ACA CAA GTT    2210
Glu Cys Phe Ala Pro Leu Tyr His Ala Met Asp Val Thr Thr Gln Val
            480             485             490

GGA GAT GAT TCT GGA GGT TTT TCA ACA ACA GTT TCT ACA GAA CAG AAT    2258
Gly Asp Asp Ser Gly Gly Phe Ser Thr Thr Val Ser Thr Glu Gln Asn
        495             500             505

GTT CCA GAT CCC CAA GTT GGT ATA ACA ACC ATG AAA GAT TTG AAA GGA    2306
Val Pro Asp Pro Gln Val Gly Ile Thr Thr Met Lys Asp Leu Lys Gly
    510             515             520

AAA GCT AAC AGA GGG AAA ATG GAT GTT TCA GGA GTA CAA GCA CCT GTG    2354
Lys Ala Asn Arg Gly Lys Met Asp Val Ser Gly Val Gln Ala Pro Val
525             530             535             540

GGA GCT ATC ACA ACA ATT GAG GAT CCA GTT TTA GCA AAG AAA GTA CCT    2402
Gly Ala Ile Thr Thr Ile Glu Asp Pro Val Leu Ala Lys Lys Val Pro
                545             550             555

GAG ACA TTT CCT GAA TTG AAA CCT GGA GAA TCC AGA CAT ACA TCA GAT    2450
Glu Thr Phe Pro Glu Leu Lys Pro Gly Glu Ser Arg His Thr Ser Asp
            560             565             570
```

FIG. 6C

```
CAT ATG TCC ATC TAC AAG TTT ATG GGA AGG TCT CAT TTC TTG TGC ACT    2498
His Met Ser Ile Tyr Lys Phe Met Gly Arg Ser His Phe Leu Cys Thr
        575             580             585

TTT ACA TTC AAT TCA AAT AAT AAA GAG TAC ACA TTT CCT ATA ACC TTG    2546
Phe Thr Phe Asn Ser Asn Asn Lys Glu Tyr Thr Phe Pro Ile Thr Leu
        590             595             600

TCT TCA ACC TCT AAT CCT CCT CAT GGT TTG CCA TCA ACA CTG AGG TGG    2594
Ser Ser Thr Ser Asn Pro Pro His Gly Leu Pro Ser Thr Leu Arg Trp
605             610             615             620

TTT TTC AAC TTG TTT CAG TTG TAT AGA GGG CCT TTA GAT CTG ACA ATT    2642
Phe Phe Asn Leu Phe Gln Leu Tyr Arg Gly Pro Leu Asp Leu Thr Ile
                625             630             635

ATT ATT ACA GGA GCA ACT GAT GTA GAT GGC ATG GCC TGG TTC ACT CCA    2690
Ile Ile Thr Gly Ala Thr Asp Val Asp Gly Met Ala Trp Phe Thr Pro
            640             645             650

GTA GGT CTT GCC GTT GAT ACT CCT TGG GTA GAG AAG GAG TCA GCT TTG    2738
Val Gly Leu Ala Val Asp Thr Pro Trp Val Glu Lys Glu Ser Ala Leu
        655             660             665

TCT ATT GAC TAC AAA ACT GCT CTT GGA GCT GTC AGA TTT AAC ACA AGG    2786
Ser Ile Asp Tyr Lys Thr Ala Leu Gly Ala Val Arg Phe Asn Thr Arg
    670             675             680

AGA ACA GGG AAC ATT CAG ATT AGA TTA CCA TGG TAT TCT TAT TTA TAT    2834
Arg Thr Gly Asn Ile Gln Ile Arg Leu Pro Trp Tyr Ser Tyr Leu Tyr
685             690             695             700
                                      A
GCT GTG TCT GGA GCA CTG GAT GGT TTG GGT GAC AAG ACA GAT TCT ACA    2882
Ala Val Ser Gly Ala Leu Asp Gly Leu Gly Asp Lys Thr Asp Ser Thr
            705             710             715

TTT GGA TTG GTT TCT ATT CAG ATT GCA AAT TAC AAT CAT TCT GAT GAA    2930
Phe Gly Leu Val Ser Ile Gln Ile Ala Asn Tyr Asn His Ser Asp Glu
        720             725             730

TAC TTG TCT TTT AGT TGT TAT TTG TCT GTC ACA GAA CAA TCA GAG TTT    2978
Tyr Leu Ser Phe Ser Cys Tyr Leu Ser Val Thr Glu Gln Ser Glu Phe
        735             740             745         T
TAT TTT CCC AGA GCT CCA TTG AAC TCA AAT GCC ATG TTA TCC ACT GAA    3026
Tyr Phe Pro Arg Ala Pro Leu Asn Ser Asn Ala Met Leu Ser Thr Glu
    750             755             760             Val

TCA ATG ATG AGC AGA ATT GCA GCT GGA GAC TTG GAG TCA TCA GTG GAT    3074
Ser Met Met Ser Arg Ile Ala Ala Gly Asp Leu Glu Ser Ser Val Asp
765             770             775             780

GAT CCT AGA TCA GAG GAA GAT AAA AGA TTT GAG AGT CAT ATA GAA TGC    3122
Asp Pro Arg Ser Glu Glu Asp Lys Arg Phe Glu Ser His Ile Glu Cys
            785             790             795
```

FIG. 6D

| | | | | | | | | | | | | | | | | |
|---|---|---|---|---|---|---|---|---|---|---|---|---|---|---|---|---|
| AGG | AAG | CCA | TAT | AAA | GAA | CTG | AGA | TTA | GAA | GTT | GGG | AAA | CAA | AGA | CTC | 3170 |
| Arg | Lys | Pro | Tyr | Lys | Glu | Leu | Arg | Leu | Glu | Val | Gly | Lys | Gln | Arg | Leu | |
| | | | 800 | | | | | 805 | | | | | | 810 | | |
| | | | | | | | | G | | | | | | | | |

AAG TAT GCT CAG GAA GAA TTG TCA AAT GAA GTA CTT CCA CCC CCT AGG 3218
Lys Tyr Ala Gln Glu Glu Leu Ser Asn Glu Val Leu Pro Pro Pro Arg
            815               820 Ser              825

AAA ATG AAG GGA CTG TTT TCA CAA GCC AAA ATT TCT CTT TTT TAT ACT 3266
Lys Met Lys Gly Leu Phe Ser Gln Ala Lys Ile Ser Leu Phe Tyr Thr
        830              835              840

GAG GAG CAT GAA ATA ATG AAG TTT TCC TGG AGA GGT GTG ACT GCT GAT 3314
Glu Glu His Glu Ile Met Lys Phe Ser Trp Arg Gly Val Thr Ala Asp
845              850              855              860

ACT AGA GCT TTA AGG AGG TTT GGA TTC TCT TTG GCC GCA GGC AGA AGT 3362
Thr Arg Ala Leu Arg Arg Phe Gly Phe Ser Leu Ala Ala Gly Arg Ser
                865              870              875

GTG TGG ACT CTT GAA ATG GAT GCT GGG GTT CTT ACT GGG AGA CTG ATT 3410
Val Trp Thr Leu Glu Met Asp Ala Gly Val Leu Thr Gly Arg Leu Ile
            880              885              890

AGA TTG AAT GAT GAG AAA TGG ACA GAA ATG AAG GAT GAC AAG ATT GTT 3458
Arg Leu Asn Asp Glu Lys Trp Thr Glu Met Lys Asp Asp Lys Ile Val
        895              900              905

TCA TTG ATT GAA AAG TTT ACA AGT AAC AAA TAT TGG TCC AAA GTG AAT 3506
Ser Leu Ile Glu Lys Phe Thr Ser Asn Lys Tyr Trp Ser Lys Val Asn
    910              915              920

TTC CCA CAT GGG ATG TTG GAT CTT GAA GAA ATT GCT GCC AAT TCT AAG 3554
Phe Pro His Gly Met Leu Asp Leu Glu Glu Ile Ala Ala Asn Ser Lys
925              930              935              940

GAT TTT CCT AAC ATG TCT GAA ACG GAT TTG TGT TTC TTG CTG CAT TGG 3602
Asp Phe Pro Asn Met Ser Glu Thr Asp Leu Cys Phe Leu Leu His Trp
            945              950              955

TTA AAT CCA AAG AAA ATT AAT TTA GCA GAT AGA ATG CTT GGA TTG TCT 3650
Leu Asn Pro Lys Lys Ile Asn Leu Ala Asp Arg Met Leu Gly Leu Ser
        960              965              970

GGA GTT CAG GAA ATT AAA GAA CAA GGT GTT GGA TTA ATA GCA GAG TGT 3698
Gly Val Gln Glu Ile Lys Glu Gln Gly Val Gly Leu Ile Ala Glu Cys
    975              980              985

AGA ACT TTC TTA GAT TCT ATT GCT GGA ACT TTA AAA TCT ATG ATG TTT 3746
Arg Thr Phe Leu Asp Ser Ile Ala Gly Thr Leu Lys Ser Met Met Phe
    990              995              1000

GGA TTT CAT CAT TCT GTG ACT GTT GAA ATT ATA AAC ACT GTG CTC TGT 3794
Gly Phe His His Ser Val Thr Val Glu Ile Ile Asn Thr Val Leu Cys
1005              1010              1015              1020

FIG. 6E

```
TTT GTT AAG AGT GGA ATT TTG CTT TAT GTA ATA CAA CAA TTG AAT CAG   3842
Phe Val Lys Ser Gly Ile Leu Leu Tyr Val Ile Gln Gln Leu Asn Gln
            1025                1030                1035
                                                             T
GAT GAA CAT TCT CAC ATA ATT GGT TTG TTG AGA GTC ATG AAT TAT GCA   3890
Asp Glu His Ser His Ile Ile Gly Leu Leu Arg Val Met Asn Tyr Ala
            1040                1045                1050    Val
                                 C
GAT ATT GGT TGT TCA GTT ATT TCA TGT GGC AAA GTT TTT TCC AAA ATG   3938
Asp Ile Gly Cys Ser Val Ile Ser Cys Gly Lys Val Phe Ser Lys Met
            1055                1060     1065
                                 Ala
CTG GAA ACA GTC TTT AAT TGG CAA ATG GAC TCC AGA ATG ATG GAG TTA   3986
Leu Glu Thr Val Phe Asn Trp Gln Met Asp Ser Arg Met Met Glu Leu
    1070                1075                1080
AGG ACT CAG AGT TTT TCC AAC TGG TTA AGA GAT ATT TGT TCT GGG ATC   4034
Arg Thr Gln Ser Phe Ser Asn Trp Leu Arg Asp Ile Cys Ser Gly Ile
1085             1090                1095                1100
         C
ACC ATT TTT AAA AAC TTC AAG GAT GCA ATT TAT TGG CTT TAT ACA AAA   4082
Thr Ile Phe Lys Asn Phe Lys Asp Ala Ile Tyr Trp Leu Tyr Thr Lys
            1105                1110                1115
 T
TTA AAG GAC TTT TAT GAA GTG AAT TAT GGC AAG AAG AAG GAC ATT TTA   4130
Leu Lys Asp Phe Tyr Glu Val Asn Tyr Gly Lys Lys Lys Asp Ile Leu
Met         1120                1125                1130
AAT ATT CTT AAA GAT AAC CAA CAA AAA ATA GAG AAA GCC ATT GAG GAA   4178
Asn Ile Leu Lys Asp Asn Gln Gln Lys Ile Glu Lys Ala Ile Glu Glu
            1135                1140                1145
         A                                               C
GCC GAT GAA TTT TGC ATT TTG CAA ATC CAA GAT GTG GAA AAA TTT GAA   4226
Ala Asp Glu Phe Cys Ile Leu Gln Ile Gln Asp Val Glu Lys Phe Glu
    1150Lys             1155                1160        Ser
CAG TAT CAG AAA GGG GTT GAC TTG ATA CAA AAA TTG AGA ACT GTT CAT   4274
Gln Tyr Gln Lys Gly Val Asp Leu Ile Gln Lys Leu Arg Thr Val His
1165                1170                1175                1180
TCA ATG GCT CAG GTT GAT CCA AAT TTA ATG GTT CAT TTG TCA CCT TTG   4322
Ser Met Ala Gln Val Asp Pro Asn Leu Met Val His Leu Ser Pro Leu
            1185                1190                1195
AGA GAT TGT ATA GCA AGA GTT CAT CAG AAA CTT AAA AAC CTT GGA TCT   4370
Arg Asp Cys Ile Ala Arg Val His Gln Lys Leu Lys Asn Leu Gly Ser
            1200                1205                1210
ATA AAT CAG GCA ATG GTA ACG AGA TGT GAG CCA GTT GTT TGT TAT TTA   4418
Ile Asn Gln Ala Met Val Thr Arg Cys Glu Pro Val Val Cys Tyr Leu
            1215                1220                1225
TAT GGC AAA AGA GGG GGA GGA AAG AGC TTA ACA TCA ATT GCA TTG GCA   4466
Tyr Gly Lys Arg Gly Gly Gly Lys Ser Leu Thr Ser Ile Ala Leu Ala
            1230                1235                1240
```

FIG. 6F

```
ACC AAA ATT TGT AAA CAT TAT GGT GTT GAG CCT GAA AAG AAT ATC TAT    4514
Thr Lys Ile Cys Lys His Tyr Gly Val Glu Pro Glu Lys Asn Ile Tyr
1245            1250            1255            1260

ACT AAA CCT GTG GCT TCA GAT TAC TGG GAT GGA TAT AGT GGA CAA TTA    4562
Thr Lys Pro Val Ala Ser Asp Tyr Trp Asp Gly Tyr Ser Gly Gln Leu
            1265            1270            1275
A
GTT TGC ATC ATT GAT GAT ATT GGC CAA AAC ACA ACA GAT GAG GAT TGG    4610
Val Cys Ile Ile Asp Asp Ile Gly Gln Asn Thr Thr Asp Glu Asp Trp
Ile         1280            1285            1290

TCA GAT TTT TGT CAG TTA GTG TCA GGA TGT CCA ATG AGA TTA AAC ATG    4658
Ser Asp Phe Cys Gln Leu Val Ser Gly Cys Pro Met Arg Leu Asn Met
            1295            1300            1305

GCC TCT CTT GAG GAG AAG GGT AGG CAT TTT TCT TCT CCT TTT ATA ATA    4706
Ala Ser Leu Glu Glu Lys Gly Arg His Phe Ser Ser Pro Phe Ile Ile
            1310            1315            1320

GCA ACT TCA AAT TGG TCA AAT CCA AGT CCA AAA ACA GTT TAT GTT AAG    4754
Ala Thr Ser Asn Trp Ser Asn Pro Ser Pro Lys Thr Val Tyr Val Lys
1325            1330            1335            1340

GAA GCA ATT GAC CGC AGA CTC CAT TTC AAG GTT GAA GTT AAA CCT GCT    4802
Glu Ala Ile Asp Arg Arg Leu His Phe Lys Val Glu Val Lys Pro Ala
            1345            1350            1355

TCA TTT TTC AAA AAT CCT CAC AAT GAT ATG TTG AAT GTT AAT TTA GCT    4850
Ser Phe Phe Lys Asn Pro His Asn Asp Met Leu Asn Val Asn Leu Ala
            1360            1365            1370

AAA ACA AAT GAT GCA ATC AAA GAT ATG TCT TGT GTT GAT TTG ATA ATG    4898
Lys Thr Asn Asp Ala Ile Lys Asp Met Ser Cys Val Asp Leu Ile Met
            1375            1380            1385

GAT GGA CAT AAT GTT TCA TTG ATG GAT TTG CTC AGT TCT TTA GTC ATG    4946
Asp Gly His Asn Val Ser Leu Met Asp Leu Leu Ser Ser Leu Val Met
            1390            1395            1400

ACA GTT GAA ATT AGA AAA CAA AAC ATG ACT GAA TTC ATG GAG TTG TGG    4994
Thr Val Glu Ile Arg Lys Gln Asn Met Thr Glu Phe Met Glu Leu Trp
1405            1410            1415            1420

TCT CAG GGA ATT TCA GAT GAT GAT AAT GAT AGT GCA GTA GCT GAG TTT    5042
Ser Gln Gly Ile Ser Asp Asp Asp Asn Asp Ser Ala Val Ala Glu Phe
            1425            1430            1435

TTC CAG TCT TTT CCA TCT GGT GAA CCA TCG AAC TCT AAA TTA TCT GGC    5090
Phe Gln Ser Phe Pro Ser Gly Glu Pro Ser Asn Ser Lys Leu Ser Gly
            1440            1445            1450

TTT TTC CAA TCT GTT ACT AAT CAC AAG TGG GTT GCT GTG GGA GCT GCA    5138
Phe Phe Gln Ser Val Thr Asn His Lys Trp Val Ala Val Gly Ala Ala
            1455            1460            1465
```

FIG. 6G

```
GTT GGC ATT CTT GGA GTG CTC GTT GGA GGA TGG TTT GTG TAT AAG CAT      5186
Val Gly Ile Leu Gly Val Leu Val Gly Gly Trp Phe Val Tyr Lys His
        1470            1475                1480
                     A                                         T
TTC TCC CGC AAA GAG GAG GAA CCA ATC CCA GCT GAA GGG GTA TAT CAT      5234
Phe Ser Arg Lys Glu Glu Glu Pro Ile Pro Ala Glu Gly Val Tyr His
1485                1490                1495                1500
                                                             Tyr
GGT GTA ACT AAG CCC AAG CAA GTG ATT AAA TTA GAT GCA GAT CCA GTA      5282
Gly Val Thr Lys Pro Lys Gln Val Ile Lys Leu Asp Ala Asp Pro Val
                1505                1510                1515
GAA TCT CAG TCA ACT TTG GAA ATA GCA GGA CTG GTT AGG AAG AAC TTG      5330
Glu Ser Gln Ser Thr Leu Glu Ile Ala Gly Leu Val Arg Lys Asn Leu
            1520                1525                1530
GTT CAG TTT GGA GTT GGA GAG AAG AAT GGA TGT GTG AGA TGG GTT ATG      5378
Val Gln Phe Gly Val Gly Glu Lys Asn Gly Cys Val Arg Trp Val Met
        1535                1540                1545
AAT GCC TTG GGA GTG AAA GAT GAT TGG CTG CTT GTG CCT TCC CAT GCT      5426
Asn Ala Leu Gly Val Lys Asp Asp Trp Leu Leu Val Pro Ser His Ala
    1550                1555                1560
TAT AAA TTT GAG AAA GAT TAT GAA ATG ATG GAG TTT TAT TTT AAT AGA      5474
Tyr Lys Phe Glu Lys Asp Tyr Glu Met Met Glu Phe Tyr Phe Asn Arg
1565                1570                1575                1580
GGT GGA ACT TAC TAT TCA ATT TCA GCT GGT AAT GTT GTT ATT CAA TCT      5522
Gly Gly Thr Tyr Tyr Ser Ile Ser Ala Gly Asn Val Val Ile Gln Ser
                1585                1590                1595
TTG GAT GTG GGA TTC CAG GAT GTT GTT CTG ATG AAG GTT CCT ACA ATT      5570
Leu Asp Val Gly Phe Gln Asp Val Val Leu Met Lys Val Pro Thr Ile
            1600                1605                1610
CCT AAG TTT AGA GAT ATT ACT CAG CAT TTT ATT AAG AAA GGG GAT GTG      5618
Pro Lys Phe Arg Asp Ile Thr Gln His Phe Ile Lys Lys Gly Asp Val
        1615                1620                1625
CCT AGA GCT TTG AAT CGC CTG GCA ACA TTA GTG ACA ACT GTA AAT GGA      5666
Pro Arg Ala Leu Asn Arg Leu Ala Thr Leu Val Thr Thr Val Asn Gly
    1630                1635                1640
ACC CCT ATG TTA ATT TCT GAG GGC CCA CTA AAG ATG GAA GAG AAA GCT      5714
Thr Pro Met Leu Ile Ser Glu Gly Pro Leu Lys Met Glu Glu Lys Ala
1645                1650                1655                1660
ACT TAT GTT CAT AAG AAA AAT GAT GGT ACA ACA GTT GAT TTA ACT GTG      5762
Thr Tyr Val His Lys Lys Asn Asp Gly Thr Thr Val Asp Leu Thr Val
                1665                1670                1675
GAT CAG GCA TGG AGA GGA AAA GGC GAA GGT CTT CCT GGA ATG TGT GGT      5810
Asp Gln Ala Trp Arg Gly Lys Gly Glu Gly Leu Pro Gly Met Cys Gly
            1680                1685                1690
```

FIG. 6H

```
GGG GCC TTG GTT TCA TCG AAT CAA TCT ATA CAG AAT GCA ATC TTG GGC    5858
Gly Ala Leu Val Ser Ser Asn Gln Ser Ile Gln Asn Ala Ile Leu Gly
        1695            1700            1705

ATC CAT GTT GCT GGA GGA AAT TCA ATT CTT GTT GCA AAA TTG GTT ACT    5906
Ile His Val Ala Gly Gly Asn Ser Ile Leu Val Ala Lys Leu Val Thr
    1710            1715            1720

CAA GAA ATG TTC CAA AAT ATT GAT AAG AAA ATT GAA AGT CAG AGA ATT    5954
Gln Glu Met Phe Gln Asn Ile Asp Lys Lys Ile Glu Ser Gln Arg Ile
1725            1730            1735            1740

ATG AAA GTG GAG TTT ACT CAG TGT TCA ATG AAT GTG GTC TCC AAA ACG    6002
Met Lys Val Glu Phe Thr Gln Cys Ser Met Asn Val Val Ser Lys Thr
            1745            1750            1755

CTT TTT AGA AAG AGT CCC ATT TAT CAT CAC ATT GAT AAA ACC ATG ATT    6050
Leu Phe Arg Lys Ser Pro Ile Tyr His His Ile Asp Lys Thr Met Ile
            1760            1765            1770

AAT TTT CCT GCA GCT ATG CCC TTT TCT AAA GCT GAA ATT GAT CCA ATG    6098
Asn Phe Pro Ala Ala Met Pro Phe Ser Lys Ala Glu Ile Asp Pro Met
            1775            1780            1785

GCT GTG ATG TTA TCT AAG TAT TCA TTA CCT ATT GTA GAA GAA CCA GAG    6146
Ala Val Met Leu Ser Lys Tyr Ser Leu Pro Ile Val Glu Glu Pro Glu
    1790            1795            1800
A
GAT TAT AAA GAG GCT TCA ATT TTT TAT CAA AAT AAA ATA GTG GGT AAG    6194
Asp Tyr Lys Glu Ala Ser Ile Phe Tyr Gln Asn Lys Ile Val Gly Lys
1805            1810            1815            1820
Asn
ACT CAG TTA GTT GAT GAT TTT TTA GAT CTT GAT ATG GCC ATT ACA GGG    6242
Thr Gln Leu Val Asp Asp Phe Leu Asp Leu Asp Met Ala Ile Thr Gly
            1825            1830            1835

GCC CCA GGA ATT GAT GCT ATC AAC ATG GAT TCA TCT CCT GGA TTT CCT    6290
Ala Pro Gly Ile Asp Ala Ile Asn Met Asp Ser Ser Pro Gly Phe Pro
            1840            1845            1850

TAT GTC CAG GAG AAG TTG ACC AAA AGA GAT TTA ATT TGG TTG GAT GAA    6338
Tyr Val Gln Glu Lys Leu Thr Lys Arg Asp Leu Ile Trp Leu Asp Glu
            1855            1860            1865

AAT GGT TTA TTG CTG GGA GTT CAT CCA AGA TTG GCT CAG AGA ATC TTA    6386
Asn Gly Leu Leu Leu Gly Val His Pro Arg Leu Ala Gln Arg Ile Leu
    1870            1875            1880

TTC AAT ACT GTC ATG ATG GAA AAT TGT TCT GAT TTG GAT GTT GTT TTT    6434
Phe Asn Thr Val Met Met Glu Asn Cys Ser Asp Leu Asp Val Val Phe
1885            1890            1895            1900

ACA ACC TGT CCA AAA GAT GAA TTG AGA CCA TTA GAG AAA GTG TTG GAA    6482
Thr Thr Cys Pro Lys Asp Glu Leu Arg Pro Leu Glu Lys Val Leu Glu
            1905            1910            1915
```

FIG. 6I

```
                                                      A
TCA AAA ACA AGA GCT ATT GAT GCT TGT CCT CTG GAT TAC TCA ATT TTG      6530
Ser Lys Thr Arg Ala Ile Asp Ala Cys Pro Leu Asp Tyr Ser Ile Leu
        1920            1925            1930
                                        Thr
TGC CGA ATG TAT TGG GGT CCA GCT ATT AGT TAT TTT CAT TTG AAT CCA      6578
Cys Arg Met Tyr Trp Gly Pro Ala Ile Ser Tyr Phe His Leu Asn Pro
        1935            1940            1945
GGT TTC CAT ACA GGT GTT GCT ATT GGC ATA GAT CCT GAT AGA CAG TGG      6626
Gly Phe His Thr Gly Val Ala Ile Gly Ile Asp Pro Asp Arg Gln Trp
        1950            1955            1960
GAT GAA TTA TTT AAA ACA ATG ATA AGA TTC GGA GAT GTT GGT CTT GAT      6674
Asp Glu Leu Phe Lys Thr Met Ile Arg Phe Gly Asp Val Gly Leu Asp
1965            1970            1975            1980
TTA GAT TTC TCT GCT TTT GAT GCT AGT CTT AGT CCA TTT ATG ATT AGA      6722
Leu Asp Phe Ser Ala Phe Asp Ala Ser Leu Ser Pro Phe Met Ile Arg
                1985            1990            1995
GAA GCA GGT AGA ATC ATG AGT GAA CTA TCT GGA ACT CCA TCC CAT TTT      6770
Glu Ala Gly Arg Ile Met Ser Glu Leu Ser Gly Thr Pro Ser His Phe
                2000            2005            2010
GGC ACA GCT CTT ATC AAT ACT ATC ATT TAT TCC AAG CAT TTG CTG TAT      6818
Gly Thr Ala Leu Ile Asn Thr Ile Ile Tyr Ser Lys His Leu Leu Tyr
        2015            2020            2025
AAC TGT TGT TAC CAT GTC TGT GGT TCA ATG CCC TCT GGG TCT CCT TGT      6866
Asn Cys Cys Tyr His Val Cys Gly Ser Met Pro Ser Gly Ser Pro Cys
        2030            2035            2040
ACA GCT TTG CTA AAT TCA ATT ATT AAT AAT GTC AAT TTG TAT TAT GTG      6914
Thr Ala Leu Leu Asn Ser Ile Ile Asn Asn Val Asn Leu Tyr Tyr Val
2045            2050            2055            2060
TTT TCC AAG ATA TTT GGA AAG TCT CCA GTT TTC TTT TGT CAG GCT TTG      6962
Phe Ser Lys Ile Phe Gly Lys Ser Pro Val Phe Phe Cys Gln Ala Leu
                2065            2070            2075
AAG ATT CTC TGT TAT GGA GAT GAT GTT TTA ATA GTT TTC TCT CGA GAT      7010
Lys Ile Leu Cys Tyr Gly Asp Asp Val Leu Ile Val Phe Ser Arg Asp
                2080            2085            2090
                        C
GTT CAG ATT GAT AAT CTT GAT TTG ATT GGA CAA AAA ATT GTA GAT GAG      7058
Val Gln Ile Asp Asn Leu Asp Leu Ile Gly Gln Lys Ile Val Asp Glu
                2095            2100            2105
TTT AAG AAA CTT GGC ATG ACA GCT ACT TCT GCT GAC AAG AAT GTA CCT      7106
Phe Lys Lys Leu Gly Met Thr Ala Thr Ser Ala Asp Lys Asn Val Pro
        2110            2115            2120
CAG CTG AAA CCA GTT TCG GAA TTG ACT TTT CTC AAA AGA TCT TTC AAT      7154
Gln Leu Lys Pro Val Ser Glu Leu Thr Phe Leu Lys Arg Ser Phe Asn
2125            2130            2135            2140
```

FIG. 6J

```
TTG GTA GAG GAT AGA ATT AGA CCT GCA ATT TCG GAA AAA ACA ATT TGG    7202
Leu Val Glu Asp Arg Ile Arg Pro Ala Ile Ser Glu Lys Thr Ile Trp
                2145            2150                2155

TCT TTA ATA GCA TGG CAG AGA AGT AAC GCT GAG TTT GAG CAG AAT TTA    7250
Ser Leu Ile Ala Trp Gln Arg Ser Asn Ala Glu Phe Glu Gln Asn Leu
                2160            2165                2170

GAA AAT GCT CAG TGG TTT GCT TTT ATG CAT GGC TAT GAG TTT TAT CAG    7298
Glu Asn Ala Gln Trp Phe Ala Phe Met His Gly Tyr Glu Phe Tyr Gln
            2175            2180                2185

AAA TTT TAT TAT TTT GTT CAG TCC TGT TTG GAG AAA GAG ATG ATA GAA    7346
Lys Phe Tyr Tyr Phe Val Gln Ser Cys Leu Glu Lys Glu Met Ile Glu
        2190            2195                2200

TAC AGA CTT AAA TCT TAT GAT TGG TGG AGA ATG AGA TTT TAT GAC CAG    7394
Tyr Arg Leu Lys Ser Tyr Asp Trp Trp Arg Met Arg Phe Tyr Asp Gln
2205            2210                2215                2220
                                                     G
TGT TTC ATT TGT GAC CTT TCA TGATTTGTTT AAACAAATTT TCTTAAAATT       7445
Cys Phe Ile Cys Asp Leu Ser
                2225

TCTGAGGTTT GTTTATTTCT TTTATCAGTA AATAAAAAAA AAAAAAAA               7493
```

FIG. 6K

HEPATITIS A VIRUS VACCINES

CROSS-REFERENCE TO RELATED PATENT APPLICATIONS

This is a continuation-in-part of U.S. patent application Ser. No. 08/397,232, filed on Mar. 10, 1995, which is the national phase filing of International Patent Application No. PCT/US93/08610, filed on Sep. 17, 1993, which is a continuation-in-part of U.S. patent application Ser. No. 07/947,338, filed on Sep. 18, 1992, now abandoned.

This invention was made with government support under certain Collaborative Research and Development Agreements awarded by the Department of Health and Human Services. The government has certain rights in this invention.

FIELD OF THE INVENTION

The present invention relates generally to the field of vaccinal compositions useful in the prophylaxis of hepatitis A. More specifically, the invention provides a novel live hepatitis A virus (HAV), and recombinant and chimeric HAVs, the genomes of which are modified from that of their parental strain HM-175 to provide them with the ability to propagate in MRC-5 cells and retain appropriate attenuation for use as live vaccines in humans and other primates.

BACKGROUND OF THE INVENTION

In the United States, hepatitis A virus is the cause of approximately 25% of all clinical hepatitis cases, accounting for approximately 150,000 such cases. Populations at high risk of acquiring hepatitis A in industrialized countries include the socially disadvantaged, medical personnel, military personnel, staff and adult contacts of children in daycare centers, male homosexuals, drug addicts, and travelers to endemic areas.

In developing countries, virtually the entire population is infected with hepatitis A virus at an early age. Much of this infection results in subclinical and inapparent infection, but, as countries improve their hygienic conditions, infection with hepatitis A virus occurs at progressively older ages, resulting in a higher proportion of clinical disease. Thus, there is a paradoxical increase in clinical hepatitis A as the overall rate of infection diminishes. To successfully immunize against hepatitis A in the United States and in other industrialized countries as well as in developing countries, it will be necessary to vaccinate the entire pediatric population. There will be an increasing need for hepatitis A vaccines in such countries for the foreseeable future.

Research in HAV vaccines has focused on inactivated, or killed, viruses. However, in vaccine therapy there are several advantages to a live vaccine, rather than an inactivated, vaccine. With a live vaccine, one can use a lower dosage and smaller number of doses, because a live vaccine replicates in the vaccinee to produce more antigen and can stimulate the immune system of the vaccinee to make both IgA and IgM. Inactivated vaccines, such as the Salk polio vaccine which stimulates production of IgG only in vaccinees, do not protect against infection by ingested virus, only against disease.

A major obstacle to the development of live, attenuated vaccine has been the difficulty in adapting HAV to a cell line that supports rapid viral growth and is licensed for vaccine production. Wild type hepatitis A virus (HAV) grows poorly in cell culture.

U.S. Pat. Nos. 4,532,215 and 4,636,469 describe, respectively, a strain of wild-type HAV, designated HM-175 [see FIG. 6 below; also SEQ ID NOS: 1 and 2], initially isolated from human feces of a patient in Melbourne, Australia, and adapted to passage in vitro in African green monkey kidney (AGMK) culture cells and methods for obtaining same by serial passaging. U.S. Pat. No. 4,620,978 describes a vaccine employing the HAV HM-175, triply cloned in AGMK cell culture and attenuated. U.S. Pat. No. 4,894,228 describes the HAV strain, HM-175, Pass 35, passaged 35 times in AGMK, which differs from wild-type HM-175 by nucleotide changes in the genome, is attenuated for chimpanzees, elicits serum neutralizing antibodies, and is suitable for use as an attenuated HAV vaccine. It discloses the complete nucleotide sequence of clone 7 of the HAV, designated HM-175/7 or pHAV/7. See FIG. 6 below; the nucleotide changes in pHAV/7 from wt HM-175 appear above the wt sequence; the amino acid changes in pHAV/7 from wt HM-175 appear below the wt amino acid. See, also, B. C. Ross et al, *J. Gen. Virol.*, 70:2805–2810 (1989); R. W. Jansen et al, *Virol.*, 163:299–307 (1988); and Tedeschi et al, *J. Med. Virol.*, 39:16–22 (1993). The disclosures of these patents and articles are incorporated by reference herein.

N. Fineschi et al, *J. Hepatol.*, 13(4):S146–S151 (1991) describes an HAV isolate, LSH/S, which is a candidate for an inactivated vaccine. It was adapted to grow in human diploid MRC-5 cells, a preferred licensed cell for vaccine development. This document compares only a small part of its nucleotide sequence to that of wild-type HM-175.

Provost et al, *J. Med. Virol.*, 20:165–175 (1986) described the F and F' variants of the CR326 hepatitis A virus strain. While it is reported to be immunogenic in volunteer vaccinees, the F variant also caused abnormal serum ALT levels in a substantial proportion of individuals.

Another publication from this group of investigators has described further work with the F' variant [K. Midthun et al, *J. Infect. Dis.*, 163:735–739 (1991)]. They observed that the immunogenicity of the F' vaccine product is dose dependent, i.e., a $10^{7.3}$ $TCID_{50}$ evoked an antibody response in 100% of volunteers within 9 weeks after immunization whereas lower doses were immunogenic in a smaller percentage of volunteers, and anti-HAV was observed 4 to 6 months after immunization. Chinese investigators have also described studies of a potential live attenuated hepatitis A vaccine prepared from the H2 strain of HAV [J. S. Mao et al, *J. Infect. Dis.*, 159:621–624 (1989)]. Twelve volunteers received the vaccine by the subcutaneous route.

A live attenuated hepatitis A vaccine could have a significant impact on the eradication of the disease. It could be anticipated that a live attenuated vaccine which requires minimal purification and no adjuvant would be less costly than presently available inactivated hepatitis A vaccines.

There is a need in the art for methods and compositions for effective vaccination of humans and animals against hepatitis A.

SUMMARY OF THE INVENTION

In one aspect, the present invention provides a live hepatitis A virus adapted to growth in MRC-5 cells. This virus is preferably characterized by attenuation. The attenuated virus may be recombinant or chimeric. More preferably, the HAV is characterized by suitable attenuation for effective vaccine administration to primates or humans, without inactivation. The HAV may be characterized by containing one or more of 16 specific nucleotides which differ from nucleotides in the same position in the genome of HAV HM-175, Pass 35 [SEQ ID NO: 3].

In another aspect, the invention provides a vaccine useful for protecting humans or other primates against hepatitis A which vaccine contains at least one above-described HAV adapted to growth in MRC-5 cells. Preferably, the vaccine is effective in inducing a protective antibody response without adjuvant.

In still another aspect, the invention provides a method for protecting humans against hepatitis A virus infection which comprises administering to the human patient an effective amount of a vaccine composition of this invention.

In a further aspect, the invention provides a method for preparing a live HAV adapted to growth in MRC-5 cells by incorporating into a selected area of the genome of an HAV one or more of thirteen specific nucleotides. The HAV genome so modified is preferably HAV HM-175, Pass 35 [SEQ ID NO: 3] or a related cell culture-adapted mutant.

In another embodiment, the HAV may be constructed using another HAV cDNA clone and inserting appropriate nucleotides into its genome. According to this method an attenuated, MRC-5-adapted HAV is provided without requiring further passaging in MRC-5 or other primate cell lines.

In still another aspect, the invention provides polynucleotide sequences encoding the recombinant or chimeric HAVs described above. Preferably these sequences are cDNAs useful as master seeds for vaccine preparation.

Other aspects and advantages of the present invention are described further in the following detailed description of the preferred embodiments thereof.

BRIEF DESCRIPTION OF THE DRAWINGS

FIGS. 6A–6K illustrate the nucleotide sequence of wt HM-175 [SEQ ID NO: 1] and its amino acid sequence [SEQ ID NO: 2]. Appearing above the nucleotides are the nucleotide changes of HM-175/7 (pHAV/7) [SEQ ID NO: 3] and appearing below the amino acids of wt HM-175 are the amino acid residues which are characteristic of pHAV/7 [SEQ ID NO: 4]. The dashes represent nucleotides present in wt HM-175 which do not appear in pHAV/7.

DETAILED DESCRIPTION OF THE INVENTION

Figure 1:
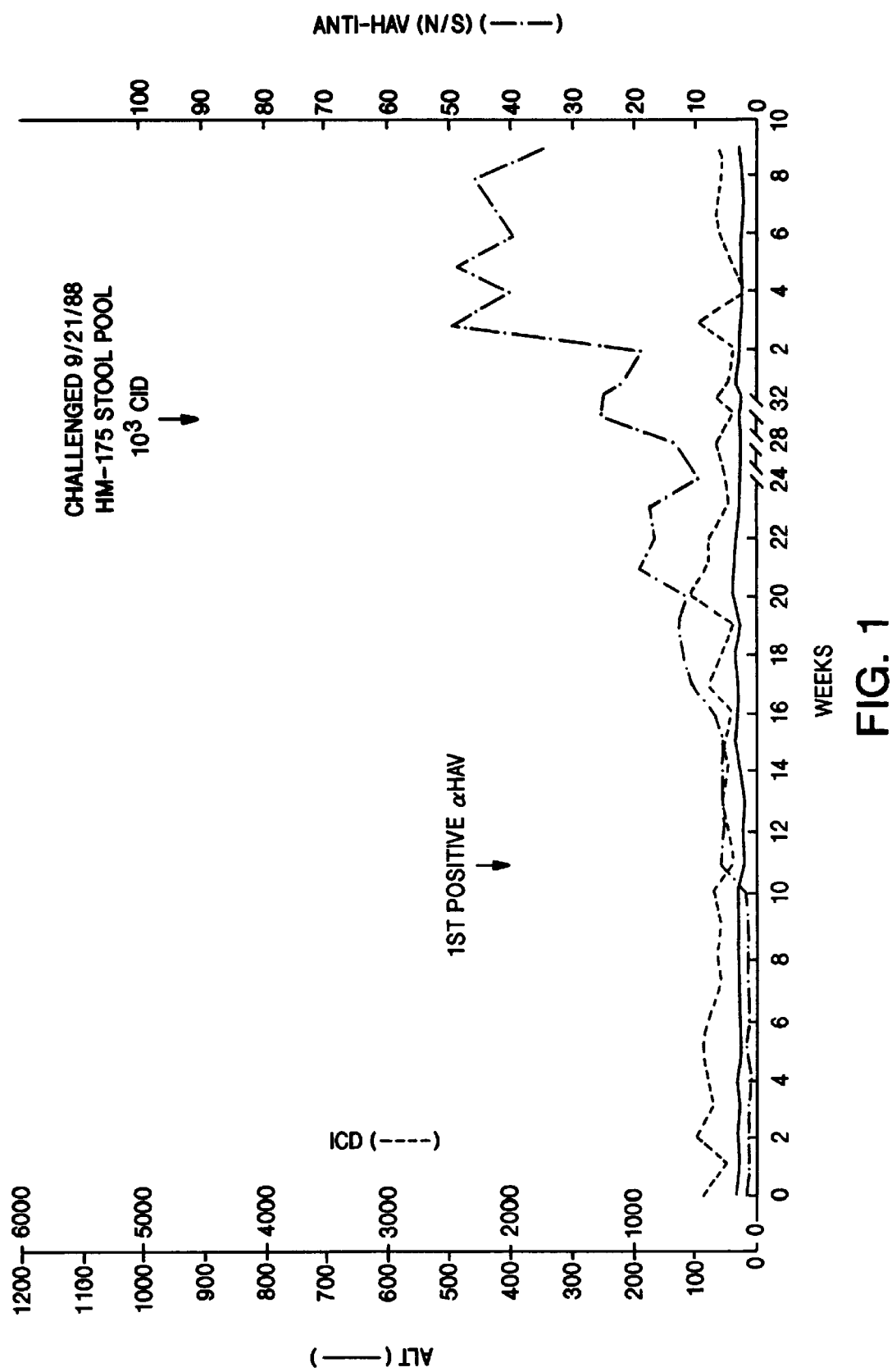
FIG. 1 is a graph plotting anti-HAV antibody production vs. time (weeks) vs. ALT and ICD levels for the chimpanzee studies with HAV virus 4380 and subsequent challenge with wild-type HAV, as described in Example 1. These results were obtained from a chimpanzee that was infected with the attenuated HAV at time 0 and challenged with virulent virus at week 28.

The present invention provides hepatitis A virus (HAV) adapted to growth in the human fibroblast-like cell line, MRC-5, a cell substrate suitable for commercial production and licensing of inactivated and live, attenuated hepatitis A vaccines. In addition to such adapted HAVs, the invention provides a method for adapting a selected HAV to growth in that human cell line and preparing an MRC-5-adapted, attenuated HAV without passaging in other primate cells. The HAV of this invention and the preparative method also preferably provides the HAV with sufficient attenuation to enable its efficacy as a vaccine for humans and animals.

Although the prior art discloses other candidate vaccine strains of hepatitis A virus which have been adapted to growth in human diploid fibroblasts, the genetic changes in the virus genome necessary and sufficient for such adaptation have not been characterized. Thus, these strains cannot be manipulated in vitro to assure a reproducible and fully-characterized vaccine product.

The present invention is based on the wild-type HAV, strain HM-175, which is described in detail in the above-cited and incorporated art [Cohen et al., *J. Virol.*, 61:50–59 (1987); SEQ ID NOS: 1 and 2]. Briefly described, the wild type, infectious HAV HM-175 virus was previously adapted to growth in primary African green monkey kidney (AGMK) cells at 37° C. After 26 passages in AGMK, the virus was cloned three times in AGMK cells by serial dilution, then passaged three more times to provide passage 32 (P-32). P-32 was found to be attenuated as described in R. A. Karron et al, *J. Infec. Dis.*, 157:338–345 (1988).

The P-32 virus described above was passaged three more times in AGMK, and molecularly cloned. The virus that was cloned was called P-35 and the full-length clone was referred to as pHAV/7 [SEQ ID NOS: 3 and 4]. pHAV/7 is an infectious cDNA clone of the virus that can be maintained in a monoclonal state and amplified at will with diminished risk of spontaneous mutations. The resulting P-35 virus grew well in fetal rhesus monkey kidney (FRhK) cells and minimally in human fibroblastoid lung cells (MRC-5).

U.S. Pat. No. 4,894,228 and Cohen et al., *Proc. Natl. Acad. Sci., USA*, 84:2497–2501 (1987) provide the HAV nucleotide sequence of wild-type HAV strain HM-175 (see, FIG. 1 of the patent; SEQ ID NO: 1) and the nucleotide differences between HAV HM-175, Pass 35, clone pHAV/7 [SEQ ID NO: 3], and the wild-type sequence. Thus, these documents, incorporated by reference, provide the nucleotide sequence of pHAV/7, P-35 [SEQ ID NO: 3]. The nucleotide numbers used herein to which the nucleotides of this invention correspond (Tables I and VI below) are the nucleotide numbers assigned to positions of the wild-type sequence of FIGS. 6A–6K [SEQ ID NOS: 1 AND 2] from U.S. Pat. No. 4,894,228 containing the mutations for P-35. Note that the nucleotides which are deleted from wild-type virus to P-35 are assigned the nucleotide position of the wild-type sequence and appear above the wt sequence of FIGS. 6A–6K as dashes (–). Thus, for example, nucleotide position 131 represents a nucleotide that was deleted between wild-type and P-35.

The P-35 cDNA, i.e., HAV/HM-175/7, is on deposit at the American Type Culture Collection, 12301 Parklawn Drive, Rockville, Md. under Accession No. 67495, deposited Aug. 7, 1987. One of skill in the art can readily construct the nucleotide and amino acid sequences of P-35 by use of the above-cited art and its deposit. See, also, SEQ ID NOS: 3 and 4.

Yet another HAV virus was provided as follows. The P-32 AGMK cell-adapted and attenuated virus was manipulated to enable it to be adapted for growth in MRC-5 cells, so that it is available for large scale vaccine production. Passage 32 was double plaque cloned in MRC-5 to form Passage 37. A selected clone 25-4-21 of Passage 37 was passaged once in MRC-5. The resulting Passage 38 was passaged three times in MRC-5 cells, resulting in Passage 41, the master seed, designated 87J19. This master seed virus stock is also referred to as HAV 4380 or MRC5/9 (the latter term reflects its ability to grow in MRC5 cell, as well as the fact that it is 9 passages from P32). This virus is referred to throughout this disclosure by the name HAV 4380.

Live attenuated virus HAV 4380, was deposited on Apr. 4, 1990 at the Collection Nationale de Cultures de Microorganismes, Institut Pasteur, 25, rue du Docteur Roux, 75724, Paris CEDEX 15 under Accession No. I-936 the deposited HAV 4380 virus has a nucleic acid sequence shown in SEQ ID NO: 5.

```
TTCAAGAGGG GTCTCCGGGA ATTTCCGGAG TCCCTCTTGG AAGTCCATGG TGAGGGGACT      60

TGATACCTCA CCGCCGTTTG CCTAGGCTAT AGGCTAAATT TTCCCTTTCC CTTTTCCCTT     120

TCCCATTCCC TTTTGCTTGT AAATATTGAT TCCTGCAGGT TCAGGGTTCT TAAATCTGTT     180

TCTCTATAAG AACACTCATT TTCACGCTTT CTGTCTTCTT TCTTCCAGGG CTCTCCCCTT     240

GCCCTAGGCT CTGGCCGTTG CGCCCGGCGG GGTCAACTCC ATGATTAGCA TGGAGCTGTA     300

GGAGTCTAAA TTGGGGACAC AGATGTTTGG AACGTCACCT TGCAGTGTTA ACTTGGCTTT     360

CATGAATCTC TTTGATCTTC CACAAGGGGT AGGCTACGGG TGAAACCTCT TAGGCTAATA     420

CTTCTATGAA GAGATGCCTT GGATAGGGTA ACAGCGGCGG ATATTGGTGA GTTGTTAAGA     480

CAAAAACCAT TCAACGCCGG AGGACTGACT CTCATCCAGT GGATGCATTG AGTGGATTGA     540

CTGTCAGGGC TGTCTTTAGG CTTAATTCCA GACCTCTCTG TGCTTGGGGC AAACATCATT     600

TGGCCTTAAA TGGGATTCTG TGAGAGGGGA TCCCTCCATT AACAGCTGGA CTGTTCTTTG     660

GGGTCTTATG TGGTGTTTGC CGCTGAGGTA CTCAGGGGCA TTTAGGTTTT TCCTCATTCT     720

TAAATAATA  ATG AAC ATG TCT AGA CAA GGT ATT TTC CAG ACT GTT GGG AGT   771

GGT CTT GAC CAC ATC CTG TCT TTG GCA GAC ATT GAG GAA GAG CAA ATG   819

ATT CAA TCA GTT GAT AGG ACT GCA GTG ACT GGT GCT TCT TAT TTT ACT   867

TCT GTG GAT CAA TCT TCA GTT CAT ACA GCT GAG GTT GGA TCA CAC CAG   915

GTT GAA CCT TTG AGA ACC TCT GTT GAT AAA CCC GGT TCA AAG AGG ACT   963

CAG GGA GAG AAA TTT TTC TTG ATT CAT TCT GCA GAT TGG CTT ACT ACA  1011

CAT GCT CTT TTC CAT GAA GTT GCA AAA TTG GAT GTG GTG AAA TTA TTA  1059

TAC AAT GAG CAG TTT GCT GTT CAA GGG TTG TTG AGA TAC CAT ACA TAT  1107

GCA AGA TTT GGC ATT GAA ATT CAA GTT CAG ATA AAC CCT ACA CCT TTC  1155

CAA CAG GGG GGA TTG ATC TGT GCT ATG GTT CCT GGT GAC CAG AGC TAT  1203

GGT TCT ATA GCA TCA TTG ACT GTT TAT CCT CAT GGT TTG TTA AAT TGC  1251

AAT ATT AAC AAT GTG GTT AGA ATA AAG GTT CCA TTT ATT TAC ACA AGA  1299

GGT GCT TAC CAC TTT AAA GAT CCA CAA TAC CCA GTT TGG GAA TTG ACA  1347

ATT AGA GTT TGG TCA GAA TTA AAT ATT GGG ACA GGA ACT TCA GCT TAT  1395

ACT TCA CTC AAT GTT TTA GCT AGA TTT ACA GAT TTG GAG TTG CAT GGA  1443

TTA ACT CCT CTT TCT ACA CAA ATG ATG AGA AAT GAA TTT AGG GTC AGT  1491

ACT ACT GAG AAT GTG GTG AAT CTG TCA AAT TAT GAA GAT GCA AGA GCA  1539

AAG ATG TCT TTT GCT TTG GAT CAG GAA GAT TGG AAA TCT GAT CCG TCC  1587
```

-continued

```
CAG GGT GGT GGG ATC AAA ATT ACT CAT TTT ACT ACT TGG ACA TCT ATT       1635
CCA ACT TTG GCT GCT CAG TTT CCA TTT AAT GCT TCA GAC TCA GTT GGT       1683
CAA CAA ATT AAA GTT ATT CCA GTT GAC CCA TAT TTT TTC CAA ATG ACA       1731
AAT ACA AAT CCT GAC CAA AAA TGT ATA ACT GCT TTG GCT TCT ATT TGT       1779
CAG ATG TTT TGT TTT TGG AGA GGA GAT CTT GTC TTT GAT TTT CAA GTT       1827
TTT CCC ACC AAA TAT CAT TCA GGT AGA TTA CTG TTT TGT TTT GTT CCT       1875
GGC AAT GAG CTA ATA GAT GTT TCT GGA ATC ACA TTA AAG CAA GCA ACT       1923
ACT GCT CCT TGT GCA GTA ATG GAT ATT ACA GGA GTG CAG TCA ACT TTG       1971
AGA TTT CGT GTT CCC TGG ATT TCT GAC ACT CCT TAC AGA GTG AAC AGG       2019
TAT ACA AAG TCA GCA CAT CAG AAA GGT GAG TAC ACT GCC ATT GGG AAG       2067
CTT ATT GTG TAT TGT TAT AAC AGA TTG ACC TCT CCT TCT AAC GTT GCT       2115
TCC CAT GTC AGA GTG AAT GTT TAT CTT TCA GCA ATT AAC TTG GAA TGT       2163
TTT GCT CCT CTT TAT CAT GCT ATG GAT GTT ACT ACA CAA GTT GGA GAT       2211
GAT TCT GGA GGT TTT TCA ACA ACA GTT TCT ACA GAA CAG AAT GTT CCA       2259
GAT CCC CAA GTT GGT ATA ACA ACC ATG AAA GAT TTG AAA GGA AAA GCT       2307
AAC AGA GGG AAA ATG GAT GTT TCA GGA GTA CAA GCA CCT GTG GGA GCT       2355
ATC ACA ACA ATT GAG GAT CCA GTT TTA GCA AAG AAA GTA CCT GAG ACA       2403
TTT CCT GAA TTG AAA CCT GGA GAA TCC AGA CAT ACA TCA GAT CAT ATG       2451
TCC ATC TAC AAG TTT ATG GGA AGG TCT CAT TTC TTG TGC ACT TTT ACA       2499
TTC AAT TCA AAT AAT AAA GAG TAC ACA TTT CCT ATA ACC TTG TCT TCA       2547
ACC TCT AAT CCT CCT CAT GGT TTG CCA TCA ACA CTG AGG TGG TTT TTC       2595
AAC TTG TTT CAG TTG TAT AGA GGG CCT TTA GAT CTG ACA ATT ATT ATT       2643
ACA GGA GCA ACT GAT GTA GAT GGC ATG GCC TGG TTC ACT CCA GTA GGT       2691
CTT GCC GTT GAT ACT CCT TGG GTA GAG AAG GAG TCA GCT TTG TCT ATT       2739
GAC TAT AAA ACT GCT CTT GGA GCT GTC AGA TTT AAC ACA AGG AGA ACA       2787
GGG AAC ATT CAG ATT AGA TTA CCA TGG TAT TCT TAT TTA TAT GCT GTG       2835
TCT GGA GCA CTG GAT GGT TTG GGA GAC AAG ACA GAT TCT ACA TTT GGA       2883
TTG GTT TCT ATT CAG ATT GCA AAT TAC AAT CAT TCT GAT GAA TAC TTG       2931
TCT TTT AGT TGT TAT TTG TCT GTC ACA GAA CAA TCA GAG TTT TAT TTT       2979
CCC AGA GCT CCA TTG AAC TCA AAT GCC ATG TTA TCC ACT GTA ACA ATG       3027
ATG AGC AGA ATT GCA GCT GGA GAC TTG AGG TCA TCA GTG GAT GAT CCT       3075
AGA TCA GAG GAA GAT AAA AGA TTT GAG AGT CAT ATA GAA TGC AGG AAG       3123
CCA TAT AAA GAA CTG AGA TTA GAA GTT GGG AAA CAA AGA CTC AAG TAT       3171
GCT CAG GAA GAA TTG TCA AAT GAA GTA CTT CCA CCC CCT AGG AAA ATG       3219
AAG GGA CTG TTT TCA CAA GCC AAA ATT TCT CTT TTT TAT ACT GAG GAG       3267
CAT GAA ATA ATG AAG TTT TCC TGG AGA GGT GTG ACT GCT GAT ACT AGA       3315
GCT TTA AGG AGG TTT GGA TTC TCT TTG CCG CCA GGC AGA AGT GTG TGG       3363
ACT CTT GAA ATG GAT GCT GGG GTT CTT ACT GGG AGA CTG ATT AGA TTG       3411
AAT GAT GAG AAA TGG ACA GAA ATG AAG GAT GAC AAG ATT GTT TCA TTG       3459
ATT GAA AAG TTT ACA AGT AAC AAA TAT TGG TCC AAA GTG AAT TTC CCA       3507
```

-continued

```
CAT GGG ATG TTG GAT CTT GAA GAA ATT GCT GCC AAT TCT AAG GAT TTT        3555
CCT AAC ATG TCT GAA ACG GAT TTG TGT TTC TTG CTG CAT TGG TTA AAT        3603
CCA AAG AAA ATT AAT TTA GCA GAT AGA ATG CTT GGA TTG TCT GGA GTT        3651
CAG GAA ATT AAA GAA CAA GGT GTT GGA TTA ATA GCA GAG TGT AGA ACT        3699
TTC TTA GAT TCT ATT GCT GGA ACT TTA AAA TCT ATG ATG TTT GGA TTT        3747
CAT CAT TCT GTG ACT GTT GAA ATT ATA AAC ACT GTG CTC TGT TTT GTT        3795
AAG AGT GGA ATT TTG CTT TAT GTA ATA CAA CAA TTG AAT CAG GAT GAA        3843
CAT TCT CAC ATA ATT GGT TTG TTG AGA GTC ATG AAT TAT GTA GAT ATT        3891
GGT TGT TCA GTT ATT TCA TGT GCC AAA GTT TTT TCC AGA ATG CTG GAA        3939
ACA GTC TTT AAT TGG CAA ATG GAC TCC AGA ATG ATG GAG TTA AGG ACT        3987
CAG AGT TTT TCC AAC TGG TTA AGA GAT ATT TGT TCT GGG ATC ACC ATT        4035
TTC AAA AAC TTC AAG GAT GCA ATT TAT TGG CTT TAT ACA AAA TTA ATG        4083
GAC TTT TAT GAA GTG AAT TAT GGC AAG AAG AAG GAC ATT TTA AAT ATT        4131
CTT AAA GAT AAC CAA CAA AAA ATA GAG AAA GCC ATT GAG GAA GCC GAT        4179
AAA TTT TGC ATT TTG CAA ATC CAA GAT GTG GAA AAA TCT GAA CAG TAT        4227
CAG AAA GGG GTT GAC TTG ATA CAA AAA TTG AGA ACT GTT CAT TCA ATG        4275
GCT CAG GTT GAT CCA AAT TTA ATG GTT CAT TTG TCA CCT TTG AGA GAT        4323
TGT ATA GCA AGA GTT CAT CAG AAA CTT AAA AAC CTT GGA TCT ATA AAT        4371
CAG GCA ATG GTA ACG AGA TGT GAG CCA GTT GTT TGT TAT TTT TAT GGC        4419
AAA AGA GGG GGA GGA AAG AGC TTA ACA TCA ATT GCA TTG GCA ACC AAA        4467
ATT TGT AAA CAT TAT GGT GTT GAG CCT GAA AAG AAT ATC TAT ACT AAA        4515
CCT GTG GCT TCA GAT TAC TGG GAT GGA TAT AGT GGA CAA TTA GTT TGC        4563
ATC ATT GAT GAT ATT GGC CAA AAC ACA ACA GAT GAG GAT TGG TCA GAT        4611
TTT TGT CAG TTA GTG TCA GGA TGT CCT ATG AGA TTA AAC ATG GCC TCT        4659
CTT GAG GAG AAG GGT AGG CAT TTT TCT TCT CCT TTT ATA ATA GCA ACT        4707
TCA AAT TGG TCA AAT CCA AGT CCA AAA ACA GTT TAT GTT AAG GAA GCA        4755
ATT GAC CGC AGA CTC CAT TTC AAG GTT GAA GTT AAA CCT GCT TCA TTT        4803
TTC AAA AAT CCT CAC AAT GAT ATG TTG AAT GTT AAT TTA GCT AAA ACA        4851
AAT GAT GCA ATC AAA GAT ATG TCT TGT GTT GAT TTG ATA ATG GAT GGA        4899
CAT AAT GTT TCA TTG ATG GAT TTG CTC AGT TCT TTA GTC ATG ACA GTT        4947
GAA ATT AGA AAA CAA AAC ATG ACT GAA TTC ATG GAG TTG TGG TCT CAG        4995
GGA ATT TCA GAT GAT GAT AAT GAT AGT GCA GTA GCT GAG TTT TTC CAG        5043
TCT TTT CCA TCT GGT GAA CCA TCG AAC TCT AAA TTA TCT GGC TTT TTC        5091
CAA TCT GTT ACT AAT CAC AAG TGG GTT GCT GTG GGA GCT GCA GTT GGC        5139
GTT CTT GGA GTG CTC GTT GGA GGA TGG TTT GTG TAT AAG CAT TTC TCC        5187
CGC AAA GAG GAA GAA CCA ATC CCA GCT GAA GGG GTA TAT TAT GGT GTA        5235
ACT AAG CCC AAG CAA GTG ATT AAA TTA GAT GCA GAT CCA GTA GAA TCT        5283
CAG TCA ACT TTG GAA ATA GCA GGA CTG GTT AGG AAG AAC TTG GTT CAG        5331
TTT GGA GTT GGA GAG AAG AAT GGA TGT GTG AGA TGG GTT ATG AAT GCC        5379
TTG GGA GTG AAA GAT GAT TGG CTG CTT GTG CCT TCC CAT GCT TAT AAA        5427
```

-continued

```
TTT GAG AAA GAT TAT GAA ATG ATG GAG TTT TAT TTT AAT AGA GGT GGA       5475
ACT TAC TAT TCA ATT TCA GCT GGT AAT GTT GTT ATT CAA TCT TTG GAT       5523
GTG GGA TTC CAG GAT GTT GTT CTG ATG AAG GTT CCT ACA ATT CCT AAG       5571
TTT AGA GAT ATT ACT CAG CAT TTT ATT AAG AAA GGG GAT GTG CCT AGA       5619
GCT TTG AAT CGC CTG GCA ACA TTA GTG ACA ACT GTA AAT GGA ACC CCT       5667
ATG TTA ATT TCT GAG GGC CCA CTA AAG ATG GAA GAG AAA GCT ACT TAT       5715
GTT CAT AAG AAA AAT GAT GGT ACA TCA GTT GAT TTA ACT GTG GAT CAG       5763
GCA TGG AGA GGA AAA GGC GAA GGT CTT CCT GGA ATG TGT GGT GGG GCC       5811
TTG GTT TCA TCG AAT CAA TCT ATA CAG AAT GCA ATC TTG GGC ATC CAT       5859
GTT GCT GGA GGA AAT TCA ATT CTT GTT GCA AAA TTG GTT ACT CAA GAA       5907
ATG TTC CAA AAT ATT GAT AAG AAA ATT GAA AGT CAG AGA ATT ATG AAA       5955
GTG GAG TTT ACT CAG TGT TCA ATG AAT GTG GTC TCC AAA ACG CTT TTT       6003
AGA AAG AGT CCC ATT TAT CAT CAC ATT GAT AAA ACC ATG ATT AAT TTT       6051
CCT GCA GCT ATG CCC TTT TCT AAA GCT GAA ATT GAT CCA ATG GCT GTG       6099
ATG TTA TCT AAG TAT TCA TTA CCT ATT GTA GAA GAA CCA GAG AAT TAT       6147
AAA GAG GCT TCA ATT TTT TAT CAA AAT AAA ATA GTG GGT AAG ACT CAG       6195
TTA GTT GAT GAT TTT CTA GAT CTT GAT ATG GCC ATT ACA GGG GCC CCA       6243
GGA ATT GAT GCT ATC AAC ATG GAT TCA TCT CCT GGA TTT CCT TAT GTC       6291
CAG GAG AAG TTG ACC AAA AGA GAT TTA ATT TGG TTG GAT GAA AAT GGT       6339
TTA TTG CTG GGA GTT CAT CCA AGA TTG GCT CAG AGA ATC TTA TTC AAT       6387
ACT GTC ATG ATG GAA AAT TGT TCT GAT TTG GAT GTT GTT TTT ACA ACC       6435
TGT CCA AAA GAT GAA TTG AGA CCA TTA GAG AAA GTG TTG GAA TCA AAA       6483
ACA AGA GCT ATT GAT GCT TGT CCT CTG GAT TAC ACA ATT TTG TGC CGA       6531
ATG TAT TGG GGT CCA GCT ATT AGT TAT TTT CAT TTG AAT CCA GGT TTC       6579
CAT ACA GGT GTT GCT ATT GGC ATA GAT CCT GAT AGA CAG TGG GAT GAA       6627
TTA TTT AAA ACA ATG ATA AGA TTC GGA GAT GTT GGT CTT GAT TTA GAT       6675
TTC TCT GCT TTT GAT GCT AGT CTT AGT CCA TTT ATG ATT AGA GAA GCA       6723
GGT AGA ATC ATG AGT GAA CTA TCT GGA ACT CCA TCC CAT TTT GGC ACA       6771
GCT CTT ATC AAT ACT ATC ATT TAT TCC AAG CAT TTG CTG TAT AAC TGT       6819
TGT TAC CAT GTC TGT GGT TCA ATG CCC TCT GGG TCT CCT TGT ACA GCT       6867
TTG CTA AAT TCA ATT ATT AAT AAT GTC AAT TTG TAC TAT GTG TTT TCC       6915
AAG ATA TTT GGA AAG TCT CCA GTT TTC TTT TGT CAG GCT TTG AAG ATT       6963
CTC TGT TAT GGA GAT GAT GTT TTA ATA GTT TTC TCT CGA GAT GTT CAG       7011
ATT GAT AAT CTT GAT TTG ATT GGA CAA AAA ATT GTA GAT GAG TTT AAG       7059
AAA CTT GGC ATG ACA GCT ACT TCT GCT GAC AAG AAT GTA CCT CAG CTG       7107
AAA CCA GTT TCG GAA TTG ACT TTT CTC AAA AGA TCT TTC AAT TTG GTA       7155
GAG GAT AGA ATT AGA ACC TGC AAT TCG GAA AAA ACA ATT TGG TCT TTA       7203
ATA GCA TGG CAG AGA AGT AAC GCT GAG TTT GAG CAG AAT TTA GAA ATT       7251
GCT CAG TGG TTT GCT TTT ATG CAT GGC TAT GAG TTT TAT CAG AAA TTT       7299
TAT TAT TTT GTT CAG TCC TGT TTG GAG AAA GAG ATG ATA GAA TAC AGA       7347
```

```
                         -continued
CTT AAA TCT TAT GAT TGG TGG AGA ATG AGA TTT TAT GAC CAG TGT TTC          7395

ATT TGT GAC CTT TCA TGATTTGTTT AAACGAATTT TCTTAAAATT TCTGAGGTTT          7450

GTTTATTTCT TTTATCAGTA AATAAAAAAA AAAAAA                                  7486
```

This deposit was made under the Budapest Treaty on the International Recognition of the Deposit of Microorganisms and has not been publicly disseminated. HAV 4380 is a cell culture-adapted and attenuated strain of hepatitis A virus strain HM-175, adapted to growth in a human fibroblast cell line (MRC-5) suitable for vaccine development by incubation at a reduced temperature of 32–35° C. Growth of the virus is determined by detection of viral antigen in a serological assay. The adapted virus is purified by plaque-purification, using an accepted method (radioimmunofocus assay).

As stated above, after a total of nine passages in MRC-5 cells at reduced temperature, the resultant virus was examined for its biological characteristics in cell culture and in two primate species that are considered to be surrogates for man, i.e., marmosets and chimpanzees. See, e.g., Example 1 below. The HAV 4380 virus was found to be temperature-sensitive (i.e., only grew at reduced temperatures) in MRC-5 cells but was still capable of growing at 37° C. in primary African green monkey kidney cells. The virus was further attenuated in virulence, compared to the parent virus HM-175, P-32, when tested in chimpanzees and marmoset monkeys, in which species the virus replicated poorly or not at all. This reduced capacity for replication in primates was further confirmed in human volunteers, as described in Example 2.

A candidate inactivated hepatitis A vaccine was prepared from the HAV 4380 and demonstrated to be safe (i.e., it does not produce hepatitis or other serious adverse effects) and immunogenic in humans. It was also found to induce antibody production without adjuvant. HAV 4380, as it currently exists, grows well in a cell substrate suitable for commercial vaccine production. It also does not infect human beings when administered by the oral or intravenous route at doses of up to $10^7$ tissue culture infectious doses, even when not inactivated. HAV 4380 is suitable for use as a live HAV vaccine in humans. However, as indicated in Example 2, vaccine 4380 is believed to be somewhat over-attenuated, because it is not infectious, which characteristic reduces its efficiency when used as an attenuated vaccine.

In order to produce other vaccine candidates which are maximized for desirable levels of attenuation and good growth in MRC-5 cells, the inventors determined the genetic changes that occurred in the genome of the MRC-5-adapted HAV 4380 virus that altered its growth characteristics and made it more suitable for vaccine production than the related AGMK-adapted virus HM-175, Passage 35 [SEQ ID NO: 3]. The discovery of the following mutations in the nucleotide sequences in HAV 4380, when compared to HM-175 Pass 35 [SEQ ID NO: 3; Cohen et al, cited above; and U.S. Pat. No. 4,894,228, FIG. 1], permit the manipulation of the HAV genome by genetic engineering techniques.

Thus, knowledge of the genomic differences between the AGMK-adapted passages of HM-175 and the more attenuated 4380 permit the construction of chimeric viruses having the improved growth characteristics, i.e., rapid and efficient growth in MRC-5 cell culture, but with a level of attenuation of virulence for primate species, including man, that will permit the virus to replicate efficiently without producing hepatitis or other untoward effects. This invention permits the design of a chimeric HAV that can achieve the optimum characteristics for a candidate live-attenuated hepatitis A vaccine. Such a virus will also permit the design of preferred inactivated vaccine candidates, if desired. The present invention identifies the mutations that are believed to have occurred during adaptation to growth of the HM-175 HAV, passage 32, strain in MRC-5 cells. One or a combination of these mutations are responsible for MRC-5 cell adaptation and overattenuation in HAV 4380.

The nucleotide sequence of the MRC-5 cell adapted virus HAV 4380 was compared with that of the AGMK-adapted, HM-175 virus, passage 35, clone 7 [SEQ ID NO: 3]. Nucleotide consensus sequences were determined directly from polymerase chain reaction products.

The inventors have discovered that there are at least sixteen unique nucleotide differences between the Pass-35 HM-175/7 virus and the MRC-5-adapted virus 4380. Table I lists these sixteen mutations by nucleotide differences and resulting amino acid (AA) differences, if any, acquired by the MRC-5-adapted virus HAV 4380. Note that the partial sequence of LSH/S HAV of Fineschi et al., cited above, overlaps with only the mutation observed at position 5145.

In the Table, A represents adenine, G represents guanine, C represents cytosine, and T represents thymine; Leu represents leucine, Phe represents phenylalanine, Ile represents isoleucine, Val represents valine, Ser represents serine, Lys represents lysine, Asn represents asparagine, Thr represents threonine and Arg represents arginine. Note that the nucleotide positions in Table I correspond with the nucleotide positions of wt HM-175 [SEQ ID NO: 1]; see FIGS. 6A–6K. This is true for all nucleotide positions referred to throughout this specification.

TABLE I

Difference in Nucleotide Sequence of MRC-5-Adapted Hepatitis A Virus: Comparison with Sequence of HM-175/7 (P-35)

| Nucleotide Change | Region of Genome | AA Change |
| --- | --- | --- |
| 591 A to G | 5' nc | NA |
| 646 G to A | 5' nc | NA |
| 669 C to T | 5' nc | NA |
| 687 T to G | 5' nc | NA |
| 2750 C to T | VP1 | No change |
| 3027 T to A | 2A | Ser to Thr |
| 3196 G to A | 2A | Ser to Asn |
| 3934 A to G | 2B | Lys to Arg |
| 4418 A to T | 2C | Leu to Phe |
| 4563 A to G | 2C | Ile to Val |
| 4643 A to T | 2C | No change |
| 5145 A to G | 3A | Ile to Val |
| 5745 A to T | 3C | Thr to Ser |
| 6908 T to C | 3D | No change |
| 7032 C to T | 3D | No change |
| 7255 A to T | 3D | Asn to Ile |

Note that two previously reported changes at nucleotide position 2864 from U to A in VP1, resulting in no amino acid change, and at nucleotide position 6216 from U to C in 3D, resulting in no amino acid change, are nucleotides that were actually present in a subset of HM175 wild-type cDNA clones made from virus before passage in cell culture. These changes occur due to microheterogeneity in some wild-type subpopulations of HM-175/7, as reported in Cohen, *Proc. Natl. Acad. Sci., USA*, 84:2497 (1987) and Cohen, *J. Virol.*, 61:50 (1987), cited above. These nucleotides were present in the wt HM-175 sequence used to prepare HAV 4380.

The nucleotide changes at positions 2750, 3027 and 7255 were previously unreported. However, all of these nucleotide changes are contained in the HAV 4380 deposited virus.

A nucleotide change at nucleotide position 6383 from a C to a U in region 3D of the HAV genome, which would cause no change in amino acid sequence, has also been detected in some clones. This change is also believed to occur in some HAV strains due to microheterogeneity in the Virus 4380, since it was not present in a PCR consensus sequence, but was present in a subclone used to make a full length virus cDNA.

New HAV vaccine candidates are designed by introducing one or more of the nucleotides mentioned in Table 1 and discussed above into an HAV at a nucleotide position homologous to the nucleotide position in the genomic sequence of the wt HM-175 [SEQ ID NO: 1] or the AGMK-adapted virus HM-175, Pass 35 [SEQ ID NO: 1]. These nucleotides identified in Table I may be introduced at analogous and/or homologous nucleotide positions to those of P-35 in the genomic sequences of other HAV strains and variants to produce a recombinant or chimeric HAV of this invention. By the phrase "analogous or homologous nucleotide position" is meant a nucleotide in an HAV other than HAV HM-175, Pass 35 which is present in the same viral region, e.g., 2C, 3D and the like, at a position in that region similar to that of the nucleotide of Table I. In other words, the nucleotide position may differ in position number due to deletions in other regions of the virus; but one of skill in the art can readily determine its functional similarity to the nucleotide position in HM-175 [SEQ ID NO: 1] or in HM-175, Pass 35 [SEQ ID NO: 3].

While such nucleotide positions may not have the identical nucleotide position numbers corresponding to the wild-type HM-175 [SEQ ID NO: 1], it is anticipated that these analogous and/or homologous positions can be readily identified to enable HAVs other than strain HM-175 derivatives to be modified to create novel HAVs according to this invention.

Similarly, the inventors are able to manipulate the genome of a progenitor or intermediate of HAV 4380 with resort to this knowledge and can thereby 'reverse' certain mutations in 4380 to create new chimeric HAV viruses. One or more of these nucleotides, or varying combinations thereof, can be incorporated, by chimera formation or oligonucleotide-directed mutagenesis, into an HAV strain, most readily the cDNA clone HAV/HM-175/7, to produce new viable virus which has acquired the ability to grow in MRC-5 cells. Other HM-175 HAV derivatives are available from the American Type Culture Collection under ATCC designation numbers VR 2089, VR 2090, VR 2091, VR 2092, VR 2093, VR 2097, VR 2098, and VR 2099. These and other HAVs may be employed to derive desired HAVs of this invention. Since there are indications that the MRC-5-adapted virus 4380 may be over-attenuated for humans, it is important to be able to remove or introduce selected mutations into HM-175. The construction of nine exemplary chimeric viruses containing one or more such mutations is described in detail in Example 3 below.

The mutagenic and genetic engineering techniques employed to construct chimeric or recombinant HAVs which incorporate one or more of these mutations are conventional and known to those of skill in the art [see, for example, Sambrook et al., *Molecular Cloning. A Laboratory Manual*, 2d edition, Cold Spring Harbor Laboratory, Cold Spring Harbor, N.Y., (1989)]. Other conventional techniques, including polymerase chain reactions and chemical synthetic techniques may also be used to design HAVs of this invention. Similarly, it is anticipated that homologous mutations may be made using other HM-175 passages. It also may be possible to adapt similar changes to HAV strains other than HM-175 by introducing these nucleotides into homologous regions.

Chimeric and recombinant viruses of this invention may be designed by application of similar techniques and selecting one or more different combinations of the nucleotides (mutations) appearing in Tables I and VI. For example, data from growth analyses of the chimeric viruses of Example 3 demonstrate that one or more of the four MRC-5 specific mutations in the 5' non-coding region (mutations at nucleotide positions 591, 646, 669, and 687 of HM-175/7) and one or both of the MRC-5 specific mutations in the 2C region (mutations at nucleotide positions 4418 and 4643 of HM-175/7) are desirable for optimal growth of the virus in MRC-5 cells.

Additional viruses employing other combinations of these mutations were prepared by conventional cloning and PCR techniques. When acting together and in the presence of the 5' non-coding and 2C mutations of Table I, MCR-5-specific mutations in P3 and VP1/2AB in every instance increased growth efficiency in MRC-5 cells. Similarly it was noted that the mutations in the 5' non-coding region increased growth efficiency in every virus and in different background genotypes. Studies have shown that the 5' non-coding mutations can reduce biochemical evidence of hepatitis. Other mutations may also be involved.

Specific exemplary chimeric HAVs of this invention are characterized by the mutations in the genome of HAV HM-175/7 that appear in viruses designated #2 through #10 in Table VI of Example 3 below. However, other chimeric HAVs may be readily prepared by application of the same methods known to those of skill in the art.

HAVs of this invention may be characterized by the presence of one or more of these nucleotides of Tables I or VI in analogous genomic positions of HAV HM-175 derivatives or other HAV strains. HAVs of this invention may also be characterized by two or more such nucleotides, where one nucleotide in the HAV parent strain is a guanine (G) at position 5145 of pHAV/7 or the analogous position of another HAV strain.

It is further anticipated that additional mutations may appear in a few regions of HAV that have yet to be sequenced. The mutations appearing in Table I may be incorporated in any combination, and/or with other mutations yet to be identified to construct a number of chimeric or recombinant HAVs with desired characteristics for use as live HAV vaccines.

Additional chimeras and recombinant viruses constructed by oligonucleotide-directed mutagenesis may be designed and evaluated for assessment of the individual effects of the mutations and combinations thereof on viral growth in MRC-5 cells and on adaptation to growth in selected cell culture. The attenuation phenotype of these chimeric viruses may be evaluated in marmosets or chimpanzees by techniques such as described below in Example 1 for HAV 4380.

Also provided by this invention are the polynucleotide sequences encoding the HAVs of this invention. Such polynucleotide sequences are preferably cDNA sequences, which can form a master seed for the HAV vaccine. A cDNA sequence of this invention comprises a DNA sequence encoding a selected HAV genome characterized by the presence of one or more of the nucleotides identified as the thirteen mutations in Table I in any desired combination which imparts desired characteristics to the novel HAV. Such cDNAs may be obtained by conventional techniques known to those of skill in the art. See, e.g., Sambrook et al, cited above, and U.S. Pat. No. 4,894,228.

Thus, the present invention provides a live vaccine composition useful in protecting against HAV infection and a prophylactic method entailing administering to a primate, preferably a human, an effective amount of such a composition. This vaccine composition may contain one or more of the HAVs of the invention, including HAV 4380, as well as the chimeric and recombinant HAVs described herein. The vaccine composition may also contain mixtures of two or more of the HAVs, if desired.

A vaccinal composition may be formulated to contain a carrier or diluent and one or more of the HAVs of the invention. Suitable pharmaceutically acceptable carriers facilitate administration of the viruses but are physiologically inert and/or nonharmful. Carriers may be selected by one of skill in the art. Exemplary carriers include sterile saline, lactose, sucrose, calcium phosphate, gelatin, dextrin, agar, pectin, peanut oil, olive oil, sesame oil, and water. Additionally, the carrier or diluent may include a time delay material, such as glycerol monostearate or glycerol distearate alone or with a wax. In addition, slow release polymer formulations can be used.

Optionally, the vaccine composition may further contain preservatives, chemical stabilizers, other antigenic proteins, and conventional pharmaceutical ingredients. Suitable ingredients which may be used in a vaccinal composition in conjunction with the viruses include, for example, casamino acids, sucrose, gelatin, phenol red, N-Z amine, monopotassium diphosphate, lactose, lactalbumin hydrolysate, and dried milk. Typically, stabilizers, adjuvants, and preservatives are optimized to determine the best formulation for efficacy in the target human or animal. Suitable preservatives include chlorobutanol, potassium sorbate, sorbic acid, sulfur dioxide, propyl gallate, the parabens, ethyl vanillin, glycerin, phenol, parachlorophenol.

A vaccine composition of this invention is most preferably produced without an adjuvant. However, where necessary, one or more of the above described vaccine components may be admixed or adsorbed with a conventional adjuvant. The adjuvant is used as a non-specific irritant to attract leukocytes or enhance an immune response. Such adjuvants include, among others, mineral oil and water, aluminum hydroxide, Amphigen, Avridine, L121/ squalene, D-lactide-polylactide/glycoside, pluronic plyois, muramyl dipeptide, killed Bordetella, saponins, and Quil A.

Alternatively, or in addition to the HAV of the invention, other agents useful in treating HAV infection, e.g., immunostimulatory agents, are expected to be useful in reducing and eliminating disease symptoms. The development of vaccine or therapeutic compositions containing these agents is within the skill of one of skill in the art in view of the teaching of this invention.

According to the method of the invention, a human or an animal may be vaccinated against HAV infection by administering an effective amount of a vaccine composition described above. An effective amount is defined as that amount of HAV vaccine capable of inducing protection in the vaccinee against HAV infection and/or against hepatitis. The vaccine may be administered by any suitable route.

Such a composition may be administered parenterally, preferably intramuscularly or subcutaneously. However, it may also be formulated to be administered by any other suitable route, including orally.

Suitable effective amounts of the HAVs of this invention can be determined by one of skill in the art based upon the level of immune response desired. Such a composition may be administered once, and/or a booster may also be administered. However, suitable dosage adjustments may be made by the attending physician or veterinarian depending upon the age, sex, weight and general health of the human or animal patient.

Similarly, suitable doses of the vaccine composition of the invention can be readily determined by one of skill in the art. The dosage can be adjusted depending upon the human patient or the animal species being treated, i.e. its weight, age, and general health.

The following examples illustrate the preferred methods for obtaining HAVs of the invention and using them as vaccine compositions. These examples are not intended to limit the scope thereof.

EXAMPLE 1

Test of MRC-5-Adapted HAV 4380 Vaccine in Marmosets and Chimpanzees

The attenuation of hepatitis A virus (HAV), strain HM-175, by serial passage in cell culture has previously been demonstrated. Following 32 passages in primary AGMK cells, the virus was completely attenuated for chimpanzees and almost completely attenuated for marmosets. Subsequently, according to this invention, the virus was adapted to growth in MRC-5 cells and recloned by plaque purification.

HAV 4380 was prepared from Volunteer lot 87J19, passage level 41 of strain HM-175 HAV that was derived from previously characterized passage levels of the virus that have also been prepared as volunteer pools. Two such earlier passage pools were shown to be attenuated for chimpanzees and marmosets. However, neither was administered to volunteers because it was recognized that primary African green monkey kidney cells, the substrate for those volunteer pools, would not be available in sufficient quantities to produce an economically viable vaccine. Therefore, the virus was adapted to MRC-5 cells and further passaged to prepare volunteer lot 87J19 or HAV 4380.

The purpose of this experiment is to test the level of attenuation of this virus for marmosets and chimpanzees, prior to phase I trials in volunteers. Lot 87J19 was tested for safety and immunogenicity in four chimpanzees and four *Saguinus mystax* marmosets. Two additional marmosets served as uninoculated controls. The chimpanzees used in this study were bred and raised in captivity; the marmosets were wild-caught animals. An inoculum of $10^4$ TCID$_{50}$ of candidate vaccine lot 87J19 was administered intravenously to each animal. Residual inoculum was frozen and the titer reconfirmed subsequently in two different laboratories.

According to the experimental protocol, marmosets identified by the arbitrary ID numbers 570, 572, 566, and 575 and chimpanzees identified by the arbitrary ID numbers 1300, 1333, 1309 and 1313 received an inoculum of HAV 4380 from Clone 25-4-21, Lot 87 J 19575, 17/11/87 at a dose and route of administration of $10^{-3}$ dilution/1 ml/I.V. Marmosets No. 541 and 578 received a diluent at a dose and route of 1 ml/I.V.

A. Infection: Three of four chimpanzees and one of four marmosets were infected, as determined by development of anti-HAV detectable by commercial radioimmunoassay (HAVAB, Abbott Laboratories, Chicago, Ill.). The chimpanzees seroconverted ten to eleven weeks following inoculation; the single marmoset seroconversion occurred eight weeks following inoculation. This marmoset subsequently died on week eleven of the study and another, noninfected, marmoset subsequently died on week fourteen, but neither death was attributable to the inoculum.

All three chimpanzees that seroconverted also developed IgM anti-HAV. Two of these, Chimp 1309 and Chimp 1313, developed IgM anti-HAV on weeks ten and thirteen, respectively, when tested by the standard HAVAB-M (Abbott Laboratories, Chicago, Ill.) at a final serum dilution of 1:4,000. When sera were tested at a dilution of 1:40, Chimp 1313 and Chimp 1333 seroconverted at weeks nine and five, respectively. The HAVAB-M test is a capture assay utilizing anti-human IgM and has not been standardized for use with sera from primates less closely related to man than to the chimpanzee. For this reason, the marmosets were not tested for IgM anti-HAV.

B. Biochemistry: Biochemical evidence of hepatitis was monitored by weekly determinations of serum alanine amino transferase (ALT) and isocitric dehydrogenase (ICD). The former is the most reliable indirect means of diagnosing hepatitis in the chimpanzee and the latter is comparably sensitive for evaluating marmosets. None of the chimpanzees or marmosets had elevation of liver enzymes attributable to the inoculum. All values for chimpanzees were within normal limits. The only infected marmoset, number 582, had normal liver enzymes up to the time of its death. Marmosets 566, 570, and 578 each had one or more abnormal liver enzyme values, but the first two of these animals were not infected by the inoculum, as judged by failure to seroconvert, and the third was an uninoculated negative control.

Marmosets often have less stable liver enzyme values than chimpanzees, in part because they are, by nature, relatively fragile animals and because they are jungle-caught and therefore usually infected with a variety of endo- and ecto-parasites, including microfilaria.

C. Histology: Histologic sections prepared from serial weekly liver biopsies obtained from the chimpanzees and marmosets were evaluated under code for histopathologic changes. Although some animals had a high base-line of histopathologic changes, none of the animals had evidence of histopathologic changes more severe than those seen in preinoculation biopsies. Equally important, there were no histologic changes that were temporally related to seroconversion in infected animals. The two marmosets that died were subjected to more extensive evaluation. Both animals had evidence of systemic disease that was probably etiologically related to their deaths, but histologic changes in the liver were diagnostic of chronic, not acute, disease and therefore not related to the inoculum.

A comparison of histopathologic changes observed in chimpanzees and marmosets with these various volunteer pools and wild-type virus was performed. See Tables II and III below.

TABLE II

HISTOPATHOLOGY: CHIMPANZEES

| | | | Liver Histopathology | |
|---|---|---|---|---|
| Inoculum* | # Inoc. | # Infected | # | Range of Severity** |
| W.T. | 4 | 4 | 4 | ±–3+ |
| P-21 | 6 | 6 | 1 | 0–3+ |
| P-32 | 6 | 6 | 0 | 0 |
| MRC-5 | 4 | 3 | 0 | 0 |

*Dose: $10^3$–$10^5$ $ID_{50}$ IV
**Scale of 0–3+

TABLE III

HISTOPATHOLOGY: MARMOSETS

| | | | Liver Histopathology | |
|---|---|---|---|---|
| Inoculum* | # Inoc. | # Infected | # | Range of Severity** |
| W.T. | 4 | 4 | 4 | 1+–2+ |
| P-21 | 8 | 8 | 8 | 1+–3+ |
| P-32 | 5 | 5 | 3 | 0–2+ |
| MRC-5 | 4 | 1 | 0 | 0 |

*Dose: $10^3$–$10^5$ $ID_{50}$ IV
**Scale of 0–3+

Lot 87J19 appears to be more attenuated than the other volunteer pools or wild-type virus, based upon infectivity and severity of histopathologic changes.

D. Immunofluorescence: Serial snap-frozen liver biopsies obtained from infected animals were evaluated for expression of viral antigen by immunofluorescence. Only one animal, Chimp 1313, was definitely but weakly positive for intrahepatic viral antigen. This animal was positive for only one week. These results were compared with those obtained in the previous study of other volunteer pools and wild-type virus. As seen in Tables IV and V, intrahepatic replication was further diminished in both chimpanzees and marmosets when compared with the AGMK-grown virus and wild-type virus.

TABLE IV

VIRAL REPLICATION IN THE LIVER: MARMOSETS (IMMUNOFLUORESCENCE)

| Inoculum* | # Inoc. | # Infected | Mean Peak | Mean Duration (wks) |
|---|---|---|---|---|
| W.T. | 4 | 4 | 2.5+ | 12.2 |
| P-21 | 8 | 8 | 1+ | 3.5 |
| P-32 | 5 | 5 | <1+ | 2.4 |
| MRC-5 | 4 | 1 | 0 | 0 |

*Dose: $10^3$–$10^5$ $ID_{50}$ I.V.

TABLE V

VIRAL REPLICATION IN THE LIVER: CHIMPANZEES (IMMUNOFLUORESCENCE)

| Inoculum* | # Inoc. | # Infected | Mean Peak | Mean Duration (wks) |
|---|---|---|---|---|
| W.T. | 4 | 4 | 1+ | 1.8 |
| P-21 | 6 | 6 | <1+ | 0.5 |

TABLE V-continued

VIRAL REPLICATION IN THE LIVER:
CHIMPANZEES (IMMUNOFLUORESCENCE)

| Inoculum* | # Inoc. | # Infected | Mean Peak | Mean Duration (wks) |
|---|---|---|---|---|
| P-32 | 6 | 6 | <1+ | 0.6 |
| MRC-5 | 4 | 3 | <1+ | 0.3 |

*Dose: $10^3$–$10^5$ ID$_{50}$ I.V.

E. Protection: Although the single infected marmoset on study died, all four chimpanzees were available for challenge with wild-type parent HAV to determine if the levels of anti-HAV present in infected animals were protective. Consequently, the three infected and one uninfected animal were challenged with approximately $10^3$ chimpanzee infectious doses of wild-type HM-175 strain HAV (human stool suspension), administered intravenously (FIGS. 1 through 4).

Figure 2:
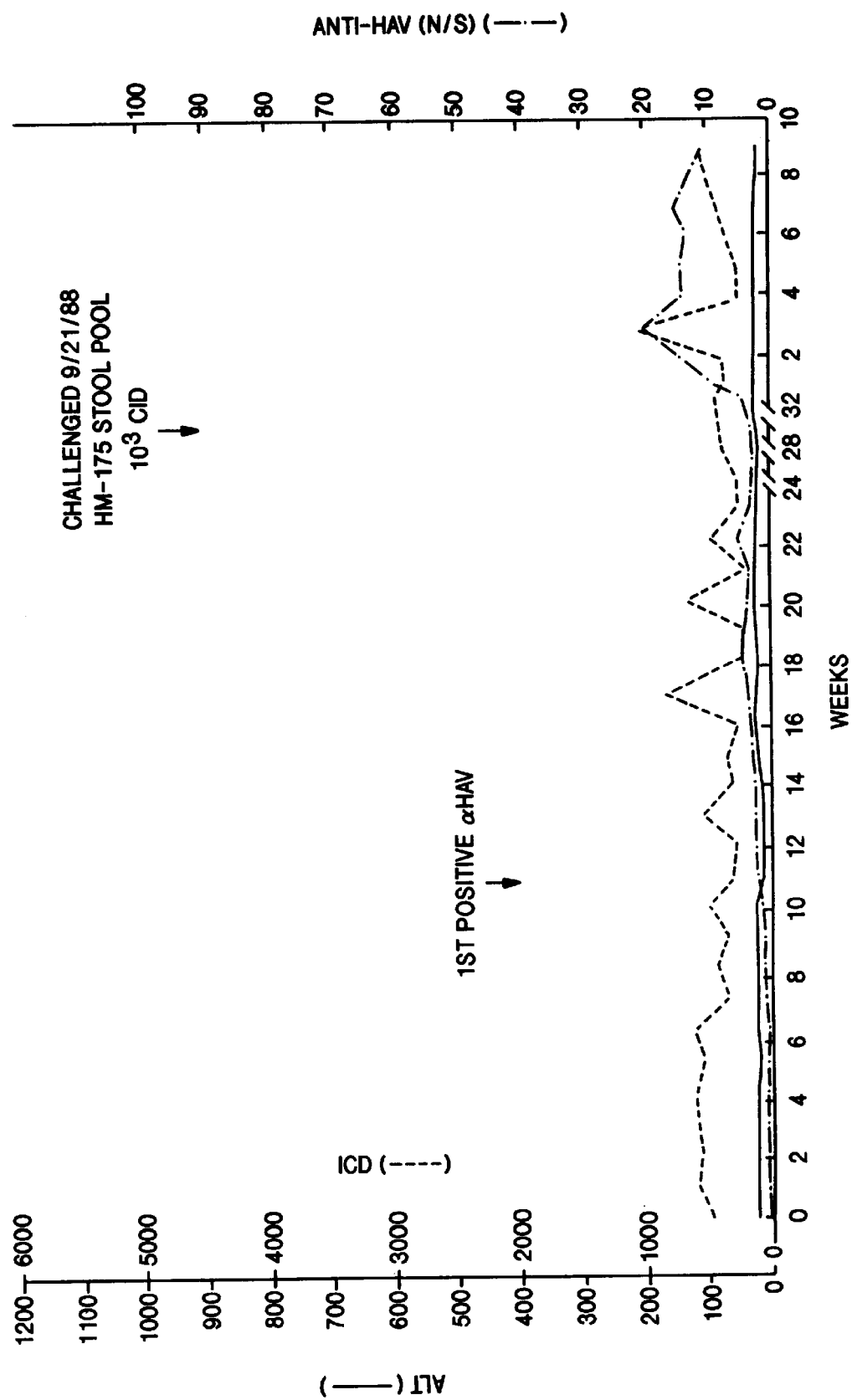
FIG. 2 is a graph plotting anti-HAV antibody production vs. time (weeks) vs. ALT and ICD levels for the chimpanzee studies with HAV virus 4380 and subsequent challenge with wild-type HAV, as described in Example 1. The conditions were the same as for FIG. 1.
Figure 3:
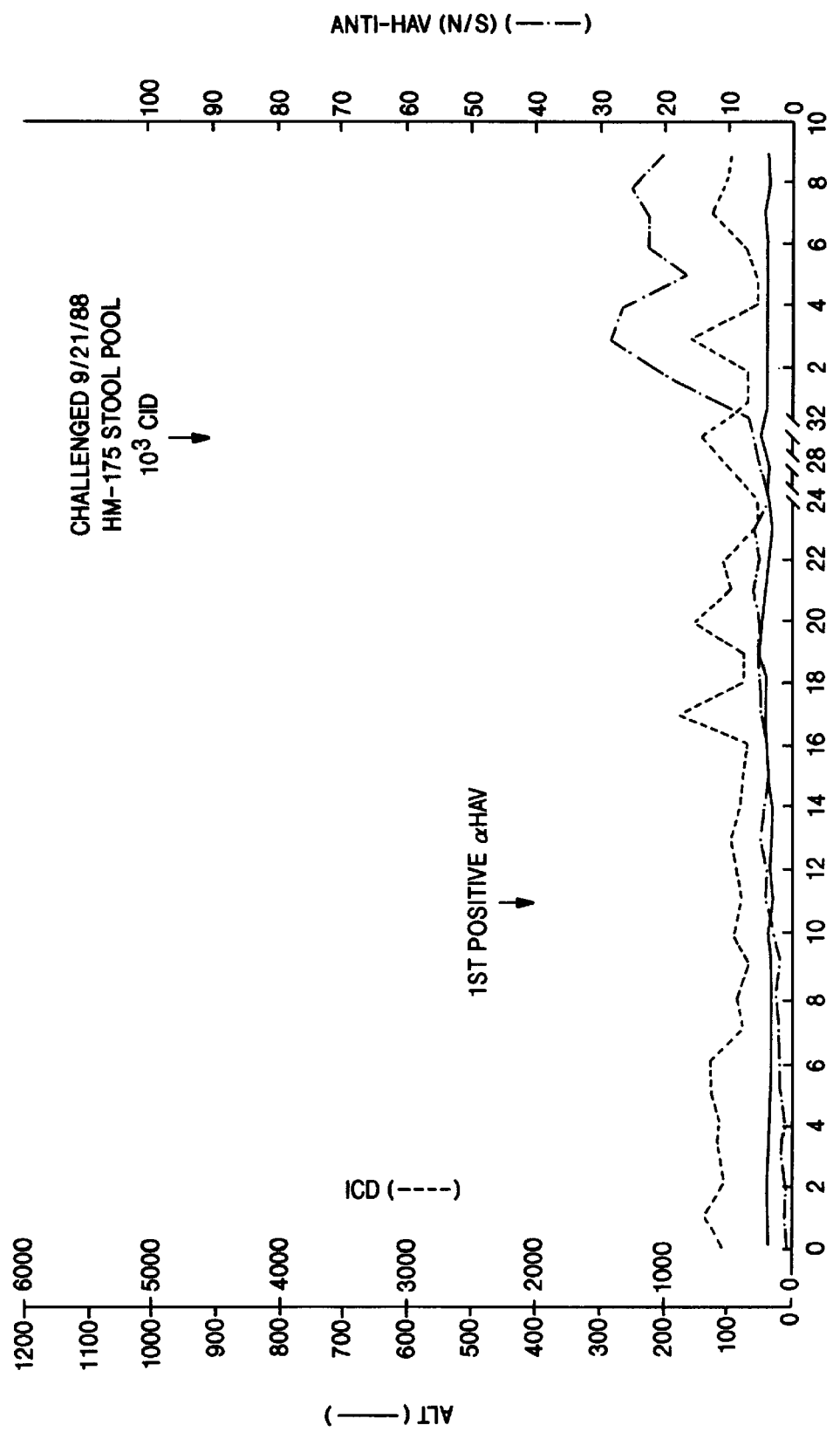
FIG. 3 is a graph plotting anti-HAV antibody production vs. time (weeks) vs. ALT and ICD levels for the chimpanzee studies with HAV virus 4380 and subsequent challenge with wild-type HAV, as described in Example 1. The conditions were the same as for FIG. 1.
Figure 4:
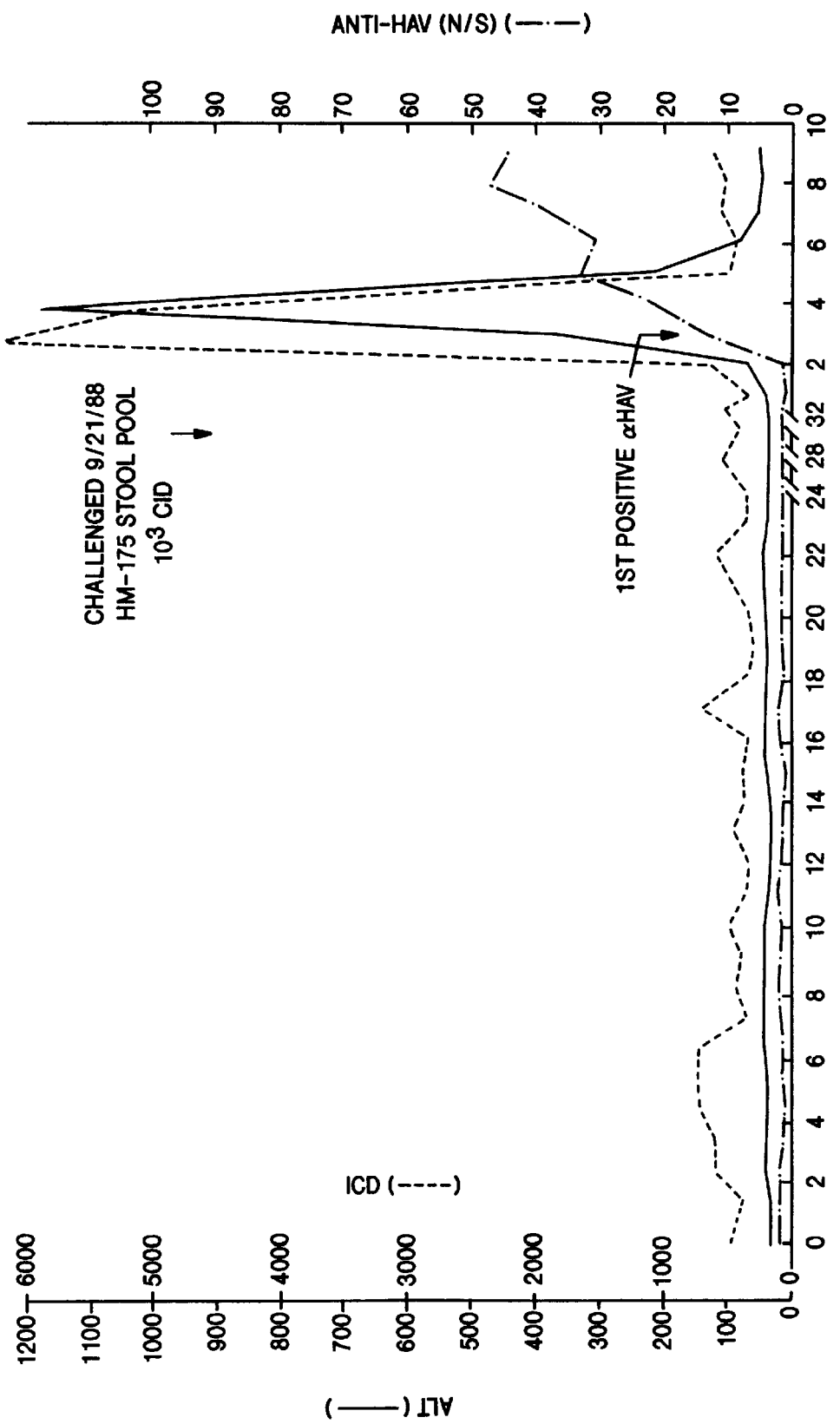
FIG. 4 is a graph plotting anti-HAV antibody production vs. time (weeks) vs. ALT and ICD levels for the chimpanzee studies with HAV virus 4380 and subsequent challenge with wild-type HAV, as described in Example 1. These results were obtained from the chimpanzee that was not infected with the attenuated HAV, and therefore developed hepatitis following challenge with the virulent virus. The conditions were the same as for FIG. 1.

All three previously infected chimpanzees were protected against type A hepatitis, as measured by persistently normal serum enzyme values (FIGS. 1 through 3). All three protected animals had an anamnestic antibody response to the challenge virus, suggesting that there was limited replication. In contrast, the previously uninfected chimpanzee developed high enzyme values diagnostic of hepatitis following challenge with wild-type virus (FIG. 4). Thus, volunteer pool 87J19 produced an inapparent infection in chimpanzees that stimulated protection against subsequent challenge with virulent wild-type virus.

The results of these portions of the experiment demonstrate that volunteer pool 87J19 of HAV 4380, strain HM-175 (adapted to MRC-5 cells) was significantly more attenuated for chimpanzees and marmosets than its parent, HAV, strain HM-175 (AGMK, Pass-32). It is clear from these studies that HAV 4380, strain HM-175 volunteer pool 87J19, is highly attenuated for chimpanzees and marmosets which are accepted surrogates for man in the study of hepatitis A viruses.

EXAMPLE 2

Clinical Study of Volunteers

In this clinical trial, volunteers received increasing titers of the live attenuated hepatitis A vaccine 4380, volunteer pool 87J19, which was previously tested in chimpanzees and marmosets as described in Example 1. These pre-clinical studies demonstrated that the vaccine was safe, immunogenic, and efficacious in experimental animal models.

Volunteers were admitted to a closed clinical ward at the United States Army Medical Research Institute of Infectious Diseases, Fort Detrick, Md. Eight volunteers received the live attenuated hepatitis A vaccine (1 ml) by the oral route in the following manner: two received a $10^4$ TCID$_{50}$ dose, two a $10^5$ TCID$_{50}$ dose, two a $10^6$ TCID$_{50}$ dose, and two a $10^7$ TCID$_{50}$ dose. Six volunteers received the vaccine by the intramuscular route in the deltoid area in the following manner: 2 received a $10^5$ TCID$_{50}$ dose, 2 a $10^6$ TCID$_{50}$ dose and 2 a $10^7$ TCID$_{50}$ dose.

Each volunteer remained on the ward for three days after immunization. Local or systemic side effects were monitored during the admission period and for 12 weeks following the immunization. Volunteers were asked to return at 6 and 12 months for serological follow-up.

Sera were obtained prior to immunization and once a week for the next 12 weeks. In volunteers who completed the appropriate follow-up time, sera were also obtained at 6 and 12 months after initial administration of vaccine. Serum specimens were tested for alanine aminotransferase (ALT) and antibody to hepatitis A. ALT was tested with a Kodak EKTA Chem 700XR analyzer (Rochester, N.Y.); normal values were 0 to 50 IU/ml. Antibody to hepatitis A was tested by four different methods, including a commercial radioimmunoassay (HAVAB, Abbott Laboratories, N. Chicago, Ill.). Second, an enzyme-linked immunoassay developed by SmithKline Beecham (SKB-ELISA), which was more sensitive than the standard HAVAB, in which a level of $\geq 20$ milli-International Units (mIU) was considered positive. Selected sera were tested by the RIFIT (radioimmunofocus) assay for neutralizing antibody to hepatitis A. With this test, a serum titer of $\geq 1:10$ was considered positive [S. M. Lemon et al, *J. Infect. Dis.*, 148:1033–1039 (1983)]. Finally sera were tested for IgM anti-HAV by commercial radioimmunoassay (HAVAB-M, Abbott Laboratories, N. Chicago, Ill.).

Stools were collected from the volunteers two to three times per week for the first 12 weeks and were tested for the presence of hepatitis A virus by radioimmunoassay [R. H. Purcell et al, *J. Immunol.*, 116:349–356 (1976)] and molecular biology techniques [J. Ticehurst et al, *J. Clin. Microbiol.*, 25:1822–1829 (1987)].

All volunteers remained healthy during the follow-up period (14 weeks to one year). No systemic complaints were present immediately after immunization or during long-term follow-up. Serum alanine aminotransferase levels remained normal in all 14 individuals during the period of observation.

Antibody to hepatitis A was not observed in any of the eight volunteers who received the vaccine by the oral route or in the two volunteers who received the $10^5$ TCID$_{50}$ dose by the intramuscular route. The four volunteers who received higher doses of vaccine ($10^6$ TCID$_{50}$ or $10^7$ TCID$_{50}$) all had detectable antibody by the SKB ELISA as early as 3 weeks after immunization. Detectable levels persisted for the 12 weeks of observation. Selected sera tested for neutralizing antibody had titers ranging from 1:10 to 1:40 in a volunteer who received a $10^6$ dose and 1:40 to 1:2560 in a volunteer who received a $10^7$ TCID$_{50}$ dose. The commercial HAVAB assay detected anti-HAV in only one of the volunteers, who received the $10^7$ dose. IgM anti-HAV was not detected in any of the volunteers who received the vaccine orally. Sera from volunteers who received $10^7$ TCID$_{50}$ I.M. had detectable IgM anti-HAV.

Stools from all volunteers who received the oral vaccine were negative for hepatitis A virus, while those from volunteers who had received the vaccine by intramuscular route are in the process of being tested.

Although only a small number of volunteers received the vaccine orally, it appeared that the vaccine is not immunogenic by this route. This is likely due to over-attenuation of the virus, although other causes, such as inactivation in the gastrointestinal tract or too small an inoculum, should be considered. The vaccine was safe and immunogenic by the intramuscular route at doses of $10^6$ and $10^7$ TCID$_{50}$. The antibody response was prompt: anti-HAV was observed within 3 weeks of immunization, persisted during the period of observation, and did not diminish in titer. Such a response to one single inoculation of a preparation which lacked an adjuvant, is remarkable. If indeed, anti-HAV persists for a long time after one dose, the logistics of administration of this product would be much simpler and more successful than with present hepatitis A vaccines. The presence of IgM anti-HAV in volunteers who received $10^7$ TCID$_{50}$ without evidence of hepatitis is suggestive of asymptomatic replication of the virus.

EXAMPLE 3

Construction of Chimeric Viruses

Several exemplary chimeric viruses were generated to evaluate the effect of several of the mutations of Table I on host range and/or attenuation in primates. The sequence of the MRC-5-adapted virus 4380 was obtained using reverse-transcriptase:polymerase chain reaction (RT:PCR) to amplify regions of the virus as cDNA prior to sequencing (hence T instead of U in Table VI below). Numbers 2–10 in Table VI designate chimeric viruses made by inserting mutations found in the MRC-5-adapted virus 4380 into the cDNA clone of pHAV/7 encoding the attenuated HM-175 virus, Pass 35, of Cohen et al., *J. Virol.*, 61:3035–3039 (1987) [SEQ ID NOs: 3 and 4]. Mutations introduced by "chimera" means a portion of the 4380 virus genome was amplified by RT:PCR, digested with specific restriction enzymes and the fragment used to replace the homologous fragment in the cDNA clone pHAV/7. Mutations introduced by mutagenesis were inserted by oligonucleotide-directed mutagenesis of the cDNA clone pHAV/7 using the Amersham mutagenesis protocol.

The chimeric cDNAs were transcribed into RNA in vitro and the nucleic acids (both RNA and DNA) transfected into FRhK-4 cells to generate chimeric viruses. Quantification of chimeric virus growth for the exemplary chimeras was performed by slot-blot assay.

Table VI reports the results of the construction and testing of nine chimeric viruses. As used in Table VI, the following terms are defined: Cell culture refers to virus containing indicated mutations selected by growth in MRC-5 cells. Mutagenesis refers to oligonucleotide-directed mutagenesis of P-35 or HM-175 cDNA clones. A chimeric viral genome refers to the construction of a chimeric viral genome using portions of P-35 cDNA clone and PCR-generated fragments of the MRC-5 cell-adapted virus 4380. ND means that this study has not yet been performed. The + symbol refers to virus that has some growth in that cell type. The—symbol refers to virus that has little or no growth in that cell type. The two cell types employed to test the growth of the chimeric viruses are the human lung fibroblast-like cell line MRC-5 and fetal rhesus monkey kidney epithelial-like cell line, FRhK-4. Note that Virus #1 in the Table refers to MRC-5-adapted HAV 4380. Viruses #2 through 10 are chimeric viruses of this invention.

TABLE VI

Differences in Nucleotide Sequence of MRC-5-Adapted Hepatitis A Virus: Comparison with P-35 HM-175 Virus

| Nucleotide Differences from P-35 HM-175 | Method Mutation Introduced | Growth of Mutated Virus in Cell Cultures FRhKA | MRC-5 |
|---|---|---|---|
| Virus #1 (MRC-5-adapted) | Cell Culture | + | + |
| 591 A to G | | | |
| 646 G to A | | | |
| 669 C to T | | | |
| 687 T to G | | | |
| 2750 C to T | | | |
| 3027 T to A | | | |
| 3196 G to A | | | |
| 3934 A to G | | | |
| 4418 A to T | | | |
| 4563 A to G | | | |
| 4643 A to T | | | |
| 5145 A to G | | | |
| 5745 A to T | | | |
| 6908 T to C | | | |
| 7032 C to T | | | |
| 7255 A to T | | | |
| Virus #2 | Chimera | + | + |
| 591 A to G | | | |
| 646 G to A | | | |
| 669 C to T | | | |
| 687 T to G | | | |
| Virus #3 | Chimera | + | + |
| 124 C to T | | | |
| 131 d to T | | | |
| 132 d to T | | | |
| 133 d to T | | | |
| 134 d to G | | | |
| 152 G to A | | | |
| 203–207 d to T | | | |
| 591 A to G | | | |
| 646 G to A | | | |
| 669 C to T | | | |
| 687 T to G | | | |
| Virus #4 | Chimera | + | + |
| 591 A to G | | | |
| 646 G to A | | | |
| 669 C to T | | | |
| 687 T to G | | | |
| 4418 A to T | | | |
| 4563 A to G | | | |
| 4643 A to T | | | |
| Virus #5 | Chimera | + | + |
| 124 C to T | | | |
| 131 d to T | | | |
| 132 d to T | | | |
| 133 d to T | | | |
| 134 d to T | | | |
| 152 G to A | | | |
| 203–207 d to T | | | |
| 591 A to G | | | |
| 646 G to A | | | |
| 669 C to T | | | |
| 687 T to G | | | |
| 4418 A to T | | | |
| 4563 A to G | | | |
| 4643 A to T | | | |
| Virus #6 | Chimera | + | − |
| 4418 A to T | | | |
| 4563 A to G | | | |
| 4643 A to T | | | |
| Virus #7 | Chimera Mutagenesis | + | ND |
| 591 A to G | | | |
| 4418 A to T | | | |
| 4563 A to G | | | |
| 4643 A to T | | | |
| Virus #8 | Chimera Mutagenesis | + | ND |
| 646 G to A | | | |
| 4418 A to T | | | |
| 4563 A to G | | | |
| 4643 A to T | | | |
| Virus #9 | Chimera Mutagenesis | + | ND |
| 669 C to T | | | |

TABLE VI-continued

Differences in Nucleotide Sequence
of MRC-5-Adapted Hepatitis A Virus:
Comparison with P-35 HM-175 Virus

| Nucleotide Differences from P-35 HM-175 | Method Mutation Introduced | Growth of Mutated Virus in Cell Cultures FRhKA | MRC-5 |
|---|---|---|---|
| 4418 A to T | | | |
| 4563 A to G | | | |
| 4643 A to T | | | |
| Virus #10 | Chimera Mutagenesis | + | ND |
| 687 T to G | | | |
| 4418 A to T | | | |
| 4563 A to G | | | |
| 4643 A to T | | | | d = Base at this position deleted in P-35 compared to wild-type

Introduction of four mutations found in the 5' noncoding region, at nucleotide positions 591, 646, 669, and 687 of the P-35 genome, appear to be important for HAV host range in cell culture. They allow some growth of the transfected virus in MRC-5 cells, but do not account entirely for MRC-5 cell culture adaptation.

Introduction of three mutations, at nucleotides 4418, 4563 and 4643 in the 2C region of the MRC-5-adapted virus, with the 5' mutations allows full growth in MRC-5 cells. Thus the four mutations in the 5' noncoding region and the three mutations in the 2C region of the genome of the MRC-5 cell-adapted virus appear to act synergistically in adaptation of this virus to efficient growth in MRC-5 cells. Introduction of only the three mutations in the 2C region into the P-35 AGMK genome does not permit discernible growth of the transfected virus in MRC-5 cells.

EXAMPLE 4

Figure 5:
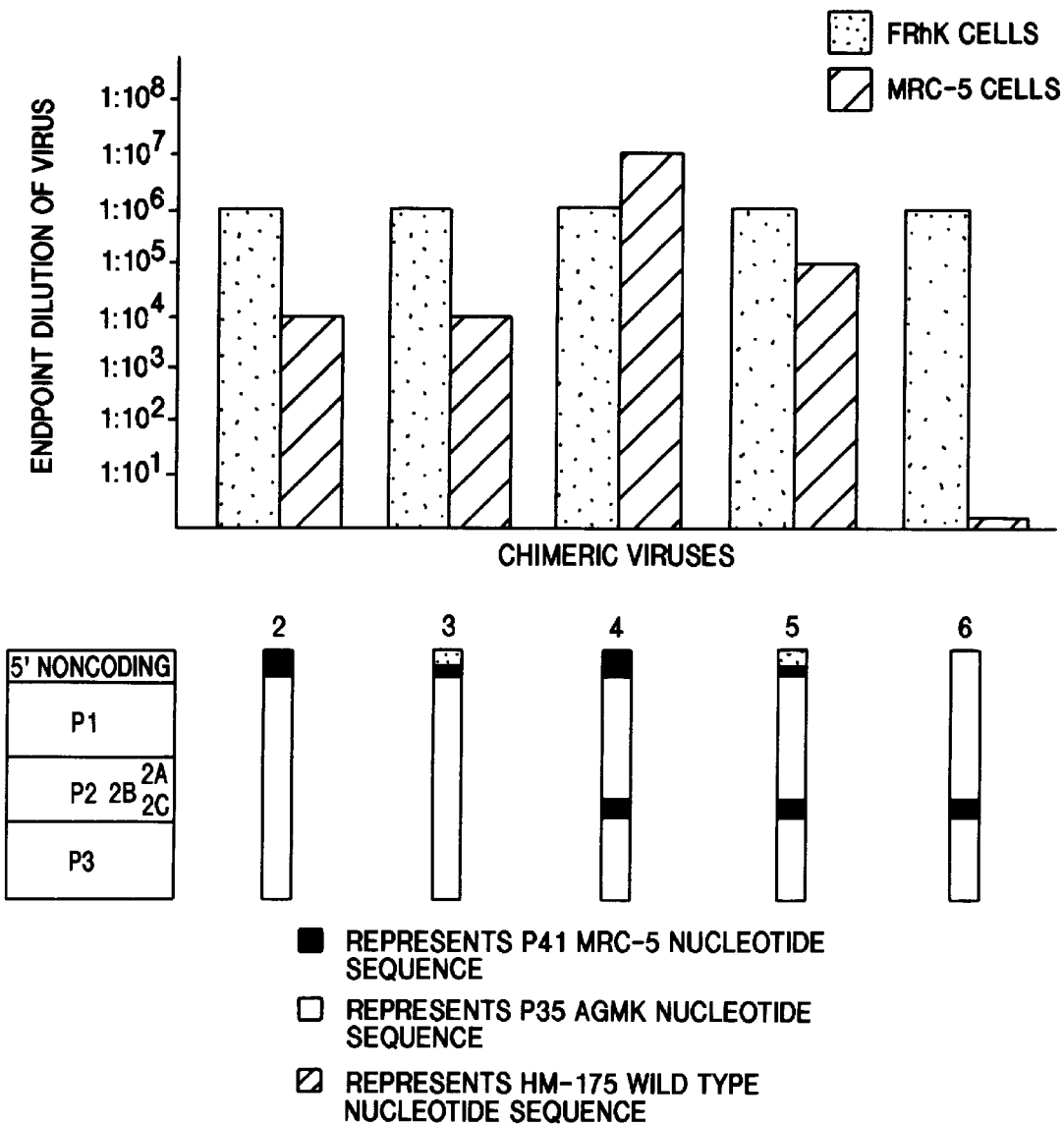
FIG. 5 is a bar graph of endpoint dilutions of several of the chimeric viruses, Viruses #2, 3, 4, 5, and 6, listed in Table VI.
Figure 7:
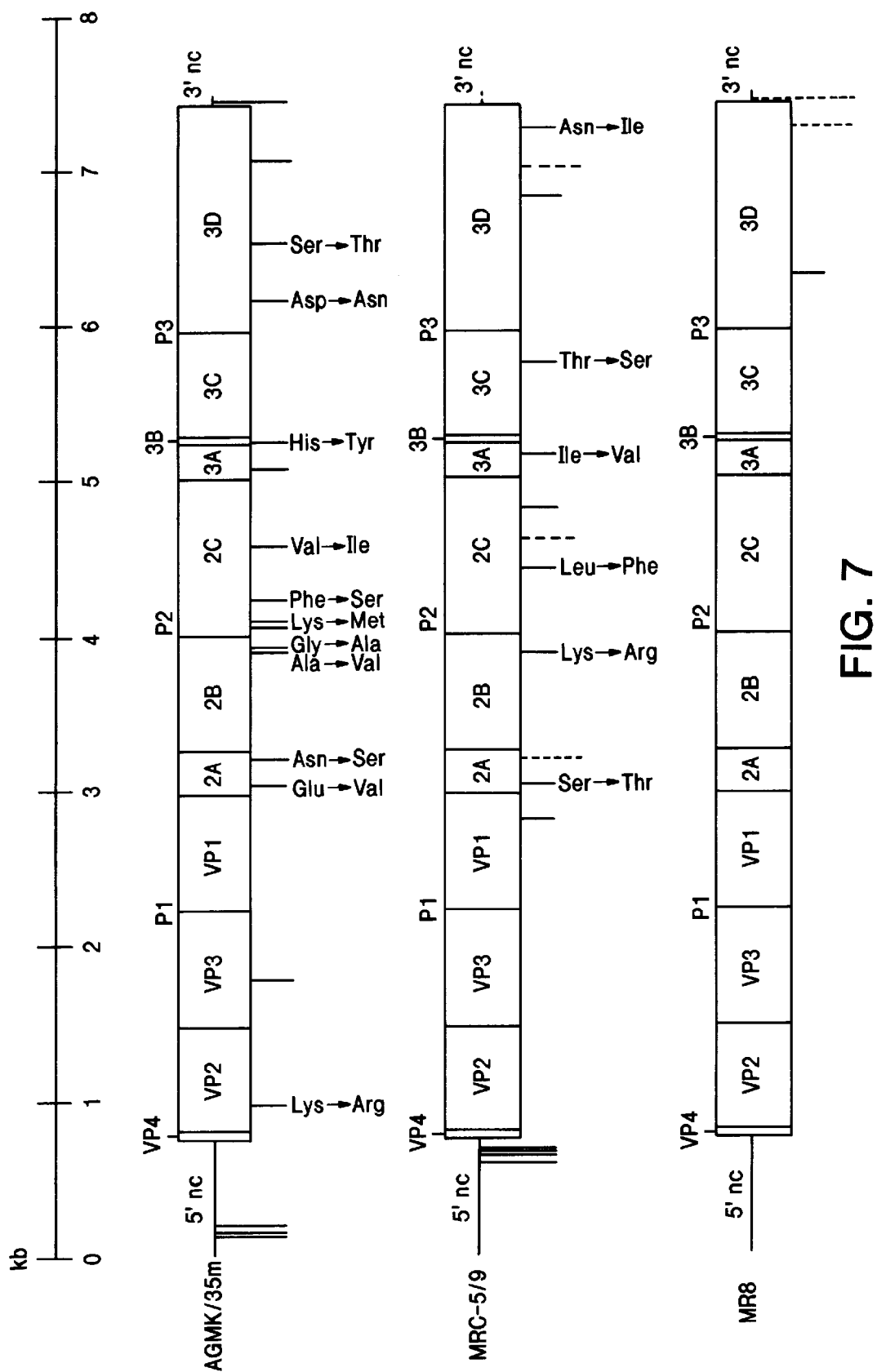
FIG. 7 provides the genomic map of the mutations that occurred during passage in AGMK cells and MRC-5 cells (both MRC5/9, which is HAV 4380; and the clone MR8 described in Example 5 below), and shows those mutations which differentiate the MR8 clone from the HAV 4380 (MRC5/9) virus. Mutations noted in each successive bar diagram represent only newly acquired mutations and resulting amino acid changes, if any, with absent mutations designed by dotted lines.

Comparison of End Point Dilution of Chimeric
Viruses in FRhK-4 Versus MRC-5 Cells Chimeric viruses with the composition described in Table VI were serially diluted in ten-fold increments, and an equal aliquot of each dilution was plated onto FRhK-4 and MRC-5 cells. After 21 days incubation at 34.5° C. to permit virus growth, the cells were lysed by the addition of a buffer solution containing sodium dodecyl sulfate. The viral RNA was extracted with phenol and quantified by slot blot hybridization using a [32P]-labeled riboprobe specific for hepatitis A virus. A radioautograph of the slot blot obtained from the FRhK-4 cells and from the MRC-5 cells illustrates that the endpoint dilution of the MRC-5-adapted virus was the same in both cell lines, indicating that this virus can grow in either cell line. In contrast, the P35 HM-175 virus had an endpoint dilution of 10–5 on FRhK-4 cells and <$10^{-1}$ on MRC-5 cells, demonstrating that this virus is unable to grow successfully on MRC-5 cells. As FIG. 5 illustrates, virus #6 was most like the pass 35 virus while virus #4 was most like the MRC-5 adapted virus and viruses #2, 3, and 5 were intermediate. These results show that certain mutations from the MRC-5-adapted virus can be introduced into the pHAV/7 cDNA clone to generate new viruses which also have acquired the ability to grow in MRC-5 cells.

EXAMPLE 5

Nucleotide Sequence of MRC-5/9 Virus Compared
with the MR8 cDNA Clone

The full length cDNA clone of an HAV chimeric virus, called MR8, was constructed by sequential replacement of AGMK/35m restriction fragments with those generated by RT-PCR amplification of the HAV 4380 (MRC-5/9) virus genome. The nucleotide sequence of the MR8 cDNA and of a subcloned PCR product from the 3' end of the viral genome (base 7000 to polyA tail) were compared to that of a PCR consensus sequence previously determined for the MRC-5/9 virus. Based on these comparisons the original list of 12 mutations believed to be unique to MRC-5/9 virus has been changed by the addition of six more coding mutations (positions 2750, 3027, 3196, 4563, 7032 and 7255) and the deletion of two mutations (position 2864 and 6216) that originally were thought to have occurred during passage in MRC-5 cells but which were actually present in a subset of HM175 wild-type cDNA clones made from virus before passage in cell culture. The two new mutations were confirmed after reamplification of the MRC-5/9 RNA by RT-PCR.

The nucleotide sequence of the MR8 clone differed from the AGMK/35m clone at nucleotide numbers 591, 646, 669 and 687 in the 5' non-coding region (identical to those in Table I). It also contained the same changes in Table I at nucleotides 2750, 3027, 3196, 3934, 4418, 4563, 4643, 5145, 5745, and 6908. It also contained at nucleotide 6383 a U, at nucleotide 7255 an A, and at nucleotide 7430 an A. Thus it contained only 7 mutations resulting in amino acid changes from AGMK/35m: (two in VP1/2A, one in 2B, two in 2C, one in 3A, and one in 3C). Only a few mutations, therefore, are responsible for a marked difference in the ability of the AGMK/35 virus and the MRC-5/9 virus to grow in MRC-5 cells.

All publications identified above are incorporated by reference. The parent applications are incorporated by reference. Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A hepatitis A virus adapted to growth in MRC-5 cells, said virus having a genome whose cDNA sequence corresponds to the cDNA sequence of HAV HM-175, Pass 35 except for nucleotide positions 591 and 687 which have guanines as bases, nucleotide position 646 which has an adenine as a base and nucleotide position 669 which has a thymine as a base; and optionally, at least one additional nucleotide selected from the group consisting of:

(a) T at position 2750;
(b) A at position 3027;
(c) A at position 3196
(d) G at position 3934;
(e) T at position 4418;
(f) G at position 4563;
(g) T at position 4643;
(h) G at position 5145;

(i) T at position 5745;
(j) C at position 6908;
(k) T at position 7032;
(l) T at position 7255;
wherein the nucleotide numbers shown above are those assigned to positions of the wild-type HM-175 sequence.

2. The virus according to claim 1 wherein the additional nucleotide is a G at position 5145.

3. The virus according to claim 1, wherein the additional nucleotide is at least one of the nucleotides (e) through (g).

4. The virus according to claim 1, wherein the additional nuclcotides are (e) through (g).

5. The virus, according to claim 1, wherein no additional nucleotides are selected.

* * * * *

SEQUENCE LISTING

<160> NUMBER OF SEQ ID NOS: 6

<210> SEQ ID NO 1
<211> LENGTH: 7493
<212> TYPE: DNA
<213> ORGANISM: WILD-TYPE HUMAN HEPATITIS A VIRUS, STRAIN HM-175

-continued

```
<220> FEATURE:
<221> NAME/KEY: CDS
<222> LOCATION: (735)..(7415)

<400> SEQUENCE: 1
ttcaagaggg gtctccggga atttccggag tccctcttgg aagtccatgg tgaggggact      60
tgatacctca ccgccgtttg cctaggctat aggctaaatt ttccctttcc cttttccctt     120
tcctattccc tttgttttgc ttgtaaatat taattcctgc aggttcaggg ttcttaaatc     180
tgtttctcta taagaacact cattttttcac gctttctgtc ttctttcttc cagggctctc    240
cccttgccct aggctctggc cgttgcgccc ggcggggtca actccatgat tagcatggag     300
ctgtaggagt ctaaattggg gacacagatg tttggaacgt caccttgcag tgttaacttg     360
gctttcatga atctctttga tcttccacaa ggggtaggct acgggtgaaa cctcttaggc     420
taatacttct atgaagagat gccttggata gggtaacagc ggcggatatt ggtgagttgt     480
taagacaaaa accattcaac gccggaggac tgactctcat ccagtggatg cattgagtgg     540
attgactgtc agggctgtct ttaggcttaa ttccagacct ctctgtgctt agggcaaaca     600
tcatttggcc ttaaatggga ttctgtgaga ggggatcccc ccattgacag ctggactgtt     660
ctttggggcc ttatgtggtg tttgcctctg aggtactcag gggcatttag gttttttcctc    720 attcttaaat aata atg aac atg tct aga caa ggt att ttc cag act gtt      770
              Met Asn Met Ser Arg Gln Gly Ile Phe Gln Thr Val
                1               5                  10 ggg agt ggt ctt gac cac atc ctg tct ttg gca gac att gag gaa gag      818
Gly Ser Gly Leu Asp His Ile Leu Ser Leu Ala Asp Ile Glu Glu Glu
         15                  20                  25 caa atg att caa tca gtt gat agg act gca gtg act ggt gct tct tat      866
Gln Met Ile Gln Ser Val Asp Arg Thr Ala Val Thr Gly Ala Ser Tyr
     30                  35                  40 ttt act tct gtg gat caa tct tca gtt cat aca gct gag gtt gga tca      914
Phe Thr Ser Val Asp Gln Ser Ser Val His Thr Ala Glu Val Gly Ser
 45                  50                  55                  60 cac cag gtt gaa cct ttg aga acc tct gtt gat aaa ccc ggt tca aag      962
His Gln Val Glu Pro Leu Arg Thr Ser Val Asp Lys Pro Gly Ser Lys
                 65                  70                  75 aag act cag gga gag aaa ttt ttc ttg att cat tct gca gat tgg ctt     1010
Lys Thr Gln Gly Glu Lys Phe Phe Leu Ile His Ser Ala Asp Trp Leu
             80                  85                  90 act aca cat gct ctt ttc cat gaa gtt gca aaa ttg gat gtg gtg aaa     1058
Thr Thr His Ala Leu Phe His Glu Val Ala Lys Leu Asp Val Val Lys
         95                 100                 105 tta tta tac aat gag cag ttt gct gtt caa ggg ttg ttg aga tac cat     1106
Leu Leu Tyr Asn Glu Gln Phe Ala Val Gln Gly Leu Leu Arg Tyr His
    110                 115                 120 aca tat gca aga ttt ggc att gaa att caa gtt cag ata aac cct aca     1154
Thr Tyr Ala Arg Phe Gly Ile Glu Ile Gln Val Gln Ile Asn Pro Thr
125                 130                 135                 140 cct ttc caa cag ggg gga ttg atc tgt gct atg gtt cct ggt gac cag     1202
Pro Phe Gln Gln Gly Gly Leu Ile Cys Ala Met Val Pro Gly Asp Gln
                145                 150                 155 agc tat ggt tct ata gca tca ttg act gtt tat cct cat ggt ttg tta     1250
Ser Tyr Gly Ser Ile Ala Ser Leu Thr Val Tyr Pro His Gly Leu Leu
            160                 165                 170 aat tgc aat att aac aat gtg gtt aga ata aag gtt cca ttt att tac     1298
Asn Cys Asn Ile Asn Asn Val Val Arg Ile Lys Val Pro Phe Ile Tyr
        175                 180                 185 aca aga ggt gct tac cac ttt aaa gat cca caa tac cca gtt tgg gaa     1346
```

-continued

```
                Thr Arg Gly Ala Tyr His Phe Lys Asp Pro Gln Tyr Pro Val Trp Glu
                    190                 195                 200 ttg aca att aga gtt tgg tca gaa tta aat att ggg aca gga act tca      1394
Leu Thr Ile Arg Val Trp Ser Glu Leu Asn Ile Gly Thr Gly Thr Ser
205                 210                 215                 220 gct tat act tca ctc aat gtt tta gct aga ttt aca gat ttg gag ttg      1442
Ala Tyr Thr Ser Leu Asn Val Leu Ala Arg Phe Thr Asp Leu Glu Leu
                225                 230                 235 cat gga tta act cct ctt tct aca caa atg atg aga aat gaa ttt agg      1490
His Gly Leu Thr Pro Leu Ser Thr Gln Met Met Arg Asn Glu Phe Arg
    240                 245                 250 gtc agt act act gag aat gtg gtg aat ctg tca aat tat gaa gat gca      1538
Val Ser Thr Thr Glu Asn Val Val Asn Leu Ser Asn Tyr Glu Asp Ala
255                 260                 265 aga gca aag atg tct ttt gct ttg gat cag gaa gat tgg aaa tct gat      1586
Arg Ala Lys Met Ser Phe Ala Leu Asp Gln Glu Asp Trp Lys Ser Asp
270                 275                 280 ccg tcc cag ggt ggt ggg atc aaa att act cat ttt act act tgg aca      1634
Pro Ser Gln Gly Gly Gly Ile Lys Ile Thr His Phe Thr Thr Trp Thr
285                 290                 295                 300 tct att cca act ttg gct gct cag ttt cca ttt aat gct tca gac tca      1682
Ser Ile Pro Thr Leu Ala Ala Gln Phe Pro Phe Asn Ala Ser Asp Ser
                305                 310                 315 gtt ggt caa caa att aaa gtt att cca gtt gac cca tat ttt ttc caa      1730
Val Gly Gln Gln Ile Lys Val Ile Pro Val Asp Pro Tyr Phe Phe Gln
                320                 325                 330 atg aca aat acg aat cct gac caa aaa tgt ata act gct ttg gct tct      1778
Met Thr Asn Thr Asn Pro Asp Gln Lys Cys Ile Thr Ala Leu Ala Ser
    335                 340                 345 att tgt cag atg ttt tgt ttt tgg aga gga gat ctt gtc ttt gat ttt      1826
Ile Cys Gln Met Phe Cys Phe Trp Arg Gly Asp Leu Val Phe Asp Phe
350                 355                 360 caa gtt ttt ccc acc aaa tat cat tca ggt aga tta ctg ttt tgt ttt      1874
Gln Val Phe Pro Thr Lys Tyr His Ser Gly Arg Leu Leu Phe Cys Phe
365                 370                 375                 380 gtt cct ggc aat gag cta ata gat gtt tct gga atc aca tta aag caa      1922
Val Pro Gly Asn Glu Leu Ile Asp Val Ser Gly Ile Thr Leu Lys Gln
                385                 390                 395 gca act act gct cct tgt gca gta atg gat att aca gga gtg cag tca      1970
Ala Thr Thr Ala Pro Cys Ala Val Met Asp Ile Thr Gly Val Gln Ser
                400                 405                 410 act ttg aga ttt cgt gtt ccc tgg att tct gac act cct tac aga gtg      2018
Thr Leu Arg Phe Arg Val Pro Trp Ile Ser Asp Thr Pro Tyr Arg Val
        415                 420                 425 aac agg tat aca aag tca gca cat cag aaa ggt gag tac act gcc att      2066
Asn Arg Tyr Thr Lys Ser Ala His Gln Lys Gly Glu Tyr Thr Ala Ile
    430                 435                 440 ggg aag ctt att gtg tat tgt tat aac aga ttg acc tct cct tct aac      2114
Gly Lys Leu Ile Val Tyr Cys Tyr Asn Arg Leu Thr Ser Pro Ser Asn
445                 450                 455                 460 gtt gct tcc cat gtc aga gtg aat gtt tat ctt tca gca att aac ttg      2162
Val Ala Ser His Val Arg Val Asn Val Tyr Leu Ser Ala Ile Asn Leu
                465                 470                 475 gaa tgt ttt gct cct ctt tat cat gct atg gat gtt act aca caa gtt      2210
Glu Cys Phe Ala Pro Leu Tyr His Ala Met Asp Val Thr Thr Gln Val
                480                 485                 490 gga gat gat tct gga ggt ttt tca aca aca gtt tct aca gaa cag aat      2258
Gly Asp Asp Ser Gly Gly Phe Ser Thr Thr Val Ser Thr Glu Gln Asn
    495                 500                 505
```

| | | |
|---|---|---|
| gtt cca gat ccc caa gtt ggt ata aca acc atg aaa gat ttg aaa gga<br>Val Pro Asp Pro Gln Val Gly Ile Thr Thr Met Lys Asp Leu Lys Gly<br>510                         515                     520 | 2306 | |
| aaa gct aac aga ggg aaa atg gat gtt tca gga gta caa gca cct gtg<br>Lys Ala Asn Arg Gly Lys Met Asp Val Ser Gly Val Gln Ala Pro Val<br>525                       530                     535                    540 | 2354 | | gga gct atc aca aca att gag gat cca gtt tta gca aag aaa gta cct   2402
Gly Ala Ile Thr Thr Ile Glu Asp Pro Val Leu Ala Lys Lys Val Pro
                  545                     550                     555 gag aca ttt cct gaa ttg aaa cct gga gaa tcc aga cat aca tca gat   2450
Glu Thr Phe Pro Glu Leu Lys Pro Gly Glu Ser Arg His Thr Ser Asp
560                       565                     570 cat atg tcc atc tac aag ttt atg gga agg tct cat ttc ttg tgc act   2498
His Met Ser Ile Tyr Lys Phe Met Gly Arg Ser His Phe Leu Cys Thr
        575                     580                     585 ttt aca ttc aat tca aat aat aaa gag tac aca ttt cct ata acc ttg   2546
Phe Thr Phe Asn Ser Asn Asn Lys Glu Tyr Thr Phe Pro Ile Thr Leu
590                       595                     600 tct tca acc tct aat cct cct cat ggt ttg cca tca aca ctg agg tgg   2594
Ser Ser Thr Ser Asn Pro Pro His Gly Leu Pro Ser Thr Leu Arg Trp
605                       610                     615                    620 ttt ttc aac ttg ttt cag ttg tat aga ggg cct tta gat ctg aca att   2642
Phe Phe Asn Leu Phe Gln Leu Tyr Arg Gly Pro Leu Asp Leu Thr Ile
                  625                     630                    635 att att aca gga gca act gat gta gat ggc atg gcc tgg ttc act cca   2690
Ile Ile Thr Gly Ala Thr Asp Val Asp Gly Met Ala Trp Phe Thr Pro
640                       645                     650 gta ggt ctt gcc gtt gat act cct tgg gta gag aag gag tca gct ttg   2738
Val Gly Leu Ala Val Asp Thr Pro Trp Val Glu Lys Glu Ser Ala Leu
        655                     660                     665 tct att gac tac aaa act gct ctt gga gct gtc aga ttt aac aca agg   2786
Ser Ile Asp Tyr Lys Thr Ala Leu Gly Ala Val Arg Phe Asn Thr Arg
670                       675                     680 aga aca ggg aac att cag att aga tta cca tgg tat tct tat tta tat   2834
Arg Thr Gly Asn Ile Gln Ile Arg Leu Pro Trp Tyr Ser Tyr Leu Tyr
685                       690                     695                    700 gct gtg tct gga gca ctg gat ggt ttg ggt gac aag aca gat tct aca   2882
Ala Val Ser Gly Ala Leu Asp Gly Leu Gly Asp Lys Thr Asp Ser Thr
                  705                     710                    715 ttt gga ttg gtt tct att cag att gca aat tac aat cat tct gat gaa   2930
Phe Gly Leu Val Ser Ile Gln Ile Ala Asn Tyr Asn His Ser Asp Glu
                720                     725                    730 tac ttg tct ttt agt tgt tat ttg tct gtc aca gaa caa tca gag ttt   2978
Tyr Leu Ser Phe Ser Cys Tyr Leu Ser Val Thr Glu Gln Ser Glu Phe
        735                     740                     745 tat ttt ccc aga gct cca ttg aac tca aat gcc atg tta tcc act gaa   3026
Tyr Phe Pro Arg Ala Pro Leu Asn Ser Asn Ala Met Leu Ser Thr Glu
750                       755                     760 tca atg atg agc aga att gca gct gga gac ttg gag tca tca gtg gat   3074
Ser Met Met Ser Arg Ile Ala Ala Gly Asp Leu Glu Ser Ser Val Asp
765                       770                     775                    780 gat cct aga tca gag gaa gat aaa aga ttt gag agt cat ata gaa tgc   3122
Asp Pro Arg Ser Glu Glu Asp Lys Arg Phe Glu Ser His Ile Glu Cys
                  785                     790                    795 agg aag cca tat aaa gaa ctg aga tta gaa gtt ggg aaa caa aga ctc   3170
Arg Lys Pro Tyr Lys Glu Leu Arg Leu Glu Val Gly Lys Gln Arg Leu
                800                     805                    810 aag tat gct cag gaa gaa ttg tca aat gaa gta ctt cca ccc cct agg   3218
Lys Tyr Ala Gln Glu Glu Leu Ser Asn Glu Val Leu Pro Pro Pro Arg
815                       820                     825

-continued

```
aaa atg aag gga ctg ttt tca caa gcc aaa att tct ctt ttt tat act    3266
Lys Met Lys Gly Leu Phe Ser Gln Ala Lys Ile Ser Leu Phe Tyr Thr
    830             835                 840 gag gag cat gaa ata atg aag ttt tcc tgg aga ggt gtg act gct gat    3314
Glu Glu His Glu Ile Met Lys Phe Ser Trp Arg Gly Val Thr Ala Asp
845             850                 855                 860 act aga gct tta agg agg ttt gga ttc tct ttg gcc gca ggc aga agt    3362
Thr Arg Ala Leu Arg Arg Phe Gly Phe Ser Leu Ala Ala Gly Arg Ser
                865                 870                 875 gtg tgg act ctt gaa atg gat gct ggg gtt ctt act ggg aga ctg att    3410
Val Trp Thr Leu Glu Met Asp Ala Gly Val Leu Thr Gly Arg Leu Ile
    880                 885                 890 aga ttg aat gat gag aaa tgg aca gaa atg aag gat gac aag att gtt    3458
Arg Leu Asn Asp Glu Lys Trp Thr Glu Met Lys Asp Asp Lys Ile Val
            895                 900                 905 tca ttg att gaa aag ttt aca agt aac aaa tat tgg tcc aaa gtg aat    3506
Ser Leu Ile Glu Lys Phe Thr Ser Asn Lys Tyr Trp Ser Lys Val Asn
910             915                 920 ttc cca cat ggg atg ttg gat ctt gaa gaa att gct gcc aat tct aag    3554
Phe Pro His Gly Met Leu Asp Leu Glu Glu Ile Ala Ala Asn Ser Lys
925             930                 935                 940 gat ttt cct aac atg tct gaa acg gat ttg tgt ttc ttg ctg cat tgg    3602
Asp Phe Pro Asn Met Ser Glu Thr Asp Leu Cys Phe Leu Leu His Trp
                945                 950                 955 tta aat cca aag aaa att aat tta gca gat aga atg ctt gga ttg tct    3650
Leu Asn Pro Lys Lys Ile Asn Leu Ala Asp Arg Met Leu Gly Leu Ser
                960                 965                 970 gga gtt cag gaa att aaa gaa caa ggt gtt gga tta ata gca gag tgt    3698
Gly Val Gln Glu Ile Lys Glu Gln Gly Val Gly Leu Ile Ala Glu Cys
            975                 980                 985 aga act ttc tta gat tct att gct gga act tta aaa tct atg atg ttt    3746
Arg Thr Phe Leu Asp Ser Ile Ala Gly Thr Leu Lys Ser Met Met Phe
        990                 995                 1000 gga ttt cat cat tct gtg act gtt gaa att ata aac act gtg ctc tgt    3794
Gly Phe His His Ser Val Thr Val Glu Ile Ile Asn Thr Val Leu Cys
1005            1010                1015                1020 ttt gtt aag agt gga att ttg ctt tat gta ata caa caa ttg aat cag    3842
Phe Val Lys Ser Gly Ile Leu Leu Tyr Val Ile Gln Gln Leu Asn Gln
                1025                1030                1035 gat gaa cat tct cac ata att ggt ttg ttg aga gtc atg aat tat gca    3890
Asp Glu His Ser His Ile Ile Gly Leu Leu Arg Val Met Asn Tyr Ala
                1040                1045                1050 gat att ggt tgt tca gtt att tca tgt ggc aaa gtt ttt tcc aaa atg    3938
Asp Ile Gly Cys Ser Val Ile Ser Cys Gly Lys Val Phe Ser Lys Met
        1055                1060                1065 ctg gaa aca gtc ttt aat tgg caa atg gac tcc aga atg atg gag tta    3986
Leu Glu Thr Val Phe Asn Trp Gln Met Asp Ser Arg Met Met Glu Leu
    1070                1075                1080 agg act cag agt ttt tcc aac tgg tta aga gat att tgt tct ggg atc    4034
Arg Thr Gln Ser Phe Ser Asn Trp Leu Arg Asp Ile Cys Ser Gly Ile
1085                1090                1095                1100 acc att ttt aaa aac ttc aag gat gca att tat tgg ctt tat aca aaa    4082
Thr Ile Phe Lys Asn Phe Lys Asp Ala Ile Tyr Trp Leu Tyr Thr Lys
                1105                1110                1115 tta aag gac ttt tat gaa gtg aat tat ggc aag aag aag gac att tta    4130
Leu Lys Asp Phe Tyr Glu Val Asn Tyr Gly Lys Lys Lys Asp Ile Leu
            1120                1125                1130 aat att ctt aaa gat aac caa caa aaa ata gag aaa gcc att gag gaa    4178
Asn Ile Leu Lys Asp Asn Gln Gln Lys Ile Glu Lys Ala Ile Glu Glu
```

-continued

```
            1135                1140                1145
gcc gat gaa ttt tgc att ttg caa atc caa gat gtg gaa aaa ttt gaa     4226
Ala Asp Glu Phe Cys Ile Leu Gln Ile Gln Asp Val Glu Lys Phe Glu
        1150                1155                1160 cag tat cag aaa ggg gtt gac ttg ata caa aaa tta aga act gtt cat     4274
Gln Tyr Gln Lys Gly Val Asp Leu Ile Gln Lys Leu Arg Thr Val His
1165                1170                1175                1180 tca atg gct cag gtt gat cca aat tta atg gtt cat ttg tca cct ttg     4322
Ser Met Ala Gln Val Asp Pro Asn Leu Met Val His Leu Ser Pro Leu
            1185                1190                1195 aga gat tgt ata gca aga gtt cat cag aaa ctt aaa aac ctt gga tct     4370
Arg Asp Cys Ile Ala Arg Val His Gln Lys Leu Lys Asn Leu Gly Ser
            1200                1205                1210 ata aat cag gca atg gta acg aga tgt gag cca gtt gtt tgt tat tta     4418
Ile Asn Gln Ala Met Val Thr Arg Cys Glu Pro Val Val Cys Tyr Leu
        1215                1220                1225 tat ggc aaa aga ggg gga gga aag agc tta aca tca att gca ttg gca     4466
Tyr Gly Lys Arg Gly Gly Gly Lys Ser Leu Thr Ser Ile Ala Leu Ala
        1230                1235                1240 acc aaa att tgt aaa cat tat ggt gtt gag cct gaa aag aat atc tat     4514
Thr Lys Ile Cys Lys His Tyr Gly Val Glu Pro Glu Lys Asn Ile Tyr
1245                1250                1255                1260 act aaa cct gtg gct tca gat tac tgg gat gga tat agt gga caa tta     4562
Thr Lys Pro Val Ala Ser Asp Tyr Trp Asp Gly Tyr Ser Gly Gln Leu
            1265                1270                1275 gtt tgc atc att gat gat att ggc caa aac aca aca gat gag gat tgg     4610
Val Cys Ile Ile Asp Asp Ile Gly Gln Asn Thr Thr Asp Glu Asp Trp
            1280                1285                1290 tca gat ttt tgt cag tta gtg tca gga tgt cca atg aga tta aac atg     4658
Ser Asp Phe Cys Gln Leu Val Ser Gly Cys Pro Met Arg Leu Asn Met
        1295                1300                1305 gcc tct ctt gag gag aag ggt agg cat ttt tct tct cct ttt ata ata     4706
Ala Ser Leu Glu Glu Lys Gly Arg His Phe Ser Ser Pro Phe Ile Ile
        1310                1315                1320 gca act tca aat tgg tca aat cca agt cca aaa aca gtt tat gtt aag     4754
Ala Thr Ser Asn Trp Ser Asn Pro Ser Pro Lys Thr Val Tyr Val Lys
1325                1330                1335                1340 gaa gca att gac cgc aga ctc cat ttc aag gtt gaa gtt aaa cct gct     4802
Glu Ala Ile Asp Arg Arg Leu His Phe Lys Val Glu Val Lys Pro Ala
            1345                1350                1355 tca ttt ttc aaa aat cct cac aat gat atg ttg aat gtt aat tta gct     4850
Ser Phe Phe Lys Asn Pro His Asn Asp Met Leu Asn Val Asn Leu Ala
            1360                1365                1370 aaa aca aat gat gca atc aaa gat atg tct tgt gtt gat tta ata atg     4898
Lys Thr Asn Asp Ala Ile Lys Asp Met Ser Cys Val Asp Leu Ile Met
        1375                1380                1385 gat gga cat aat gtt tca ttg atg gat ttg ctc agt tct tta gtc atg     4946
Asp Gly His Asn Val Ser Leu Met Asp Leu Leu Ser Ser Leu Val Met
        1390                1395                1400 aca gtt gaa att aga aaa caa aac atg act gaa ttc atg gag ttg tgg     4994
Thr Val Glu Ile Arg Lys Gln Asn Met Thr Glu Phe Met Glu Leu Trp
1405                1410                1415                1420 tct cag gga att tca gat gat gat aat gat agt gca gta gct gag ttt     5042
Ser Gln Gly Ile Ser Asp Asp Asp Asn Asp Ser Ala Val Ala Glu Phe
            1425                1430                1435 ttc cag tct ttt cca tct ggt gaa cca tcg aac tct aaa tta tct ggc     5090
Phe Gln Ser Phe Pro Ser Gly Glu Pro Ser Asn Ser Lys Leu Ser Gly
            1440                1445                1450 ttt ttc caa tct gtt act aat cac aag tgg gtt gct gtg gga gct gca     5138
```

```
Phe Phe Gln Ser Val Thr Asn His Lys Trp Val Ala Gly Ala Ala
        1455                1460                1465 gtt ggc att ctt gga gtg ctc gtt gga gga tgg ttt gtg tat aag cat         5186
Val Gly Ile Leu Gly Val Leu Val Gly Gly Trp Phe Val Tyr Lys His
1470                1475                1480 ttc tcc cgc aaa gag gag gaa cca atc cca gct gaa ggg gta tat cat         5234
Phe Ser Arg Lys Glu Glu Glu Pro Ile Pro Ala Glu Gly Val Tyr His
1485                1490                1495                1500 ggt gta act aag ccc aag caa gtg att aaa tta gat gca gat cca gta         5282
Gly Val Thr Lys Pro Lys Gln Val Ile Lys Leu Asp Ala Asp Pro Val
        1505                1510                1515 gaa tct cag tca act ttg gaa ata gca gga ctg gtt agg aag aac ttg         5330
Glu Ser Gln Ser Thr Leu Glu Ile Ala Gly Leu Val Arg Lys Asn Leu
        1520                1525                1530 gtt cag ttt gga gtt gga gag aag aat gga tgt gtg aga tgg gtt atg         5378
Val Gln Phe Gly Val Gly Glu Lys Asn Gly Cys Val Arg Trp Val Met
        1535                1540                1545 aat gcc ttg gga gtg aaa gat gat tgg ctg ctt gtg cct tcc cat gct         5426
Asn Ala Leu Gly Val Lys Asp Asp Trp Leu Leu Val Pro Ser His Ala
        1550                1555                1560 tat aaa ttt gag aaa gat tat gaa atg atg gag ttt tat ttt aat aga         5474
Tyr Lys Phe Glu Lys Asp Tyr Glu Met Met Glu Phe Tyr Phe Asn Arg
1565                1570                1575                1580 ggt gga act tac tat tca att tca gct ggt aat gtt gtt att caa tct         5522
Gly Gly Thr Tyr Tyr Ser Ile Ser Ala Gly Asn Val Val Ile Gln Ser
        1585                1590                1595 ttg gat gtg gga ttc cag gat gtt gtt ctg atg aag gtt cct aca att         5570
Leu Asp Val Gly Phe Gln Asp Val Val Leu Met Lys Val Pro Thr Ile
        1600                1605                1610 cct aag ttt aga gat att act cag cat ttt att aag aaa ggg gat gtg         5618
Pro Lys Phe Arg Asp Ile Thr Gln His Phe Ile Lys Lys Gly Asp Val
        1615                1620                1625 cct aga gct ttg aat cgc ctg gca aca tta gtg aca act gta aat gga         5666
Pro Arg Ala Leu Asn Arg Leu Ala Thr Leu Val Thr Thr Val Asn Gly
        1630                1635                1640 acc cct atg tta att tct gag ggc cca cta aag atg gaa gag aaa gct         5714
Thr Pro Met Leu Ile Ser Glu Gly Pro Leu Lys Met Glu Glu Lys Ala
1645                1650                1655                1660 act tat gtt cat aag aaa aat gat ggt aca aca gtt gat tta act gtg         5762
Thr Tyr Val His Lys Lys Asn Asp Gly Thr Thr Val Asp Leu Thr Val
        1665                1670                1675 gat cag gca tgg aga gga aaa ggc gaa ggt ctt cct gga atg tgt ggt         5810
Asp Gln Ala Trp Arg Gly Lys Gly Glu Gly Leu Pro Gly Met Cys Gly
        1680                1685                1690 ggg gcc ttg gtt tca tcg aat caa tct ata cag aat gca atc ttg ggc         5858
Gly Ala Leu Val Ser Ser Asn Gln Ser Ile Gln Asn Ala Ile Leu Gly
        1695                1700                1705 atc cat gtt gct gga gga aat tca att ctt gtt gca aaa ttg gtt act         5906
Ile His Val Ala Gly Gly Asn Ser Ile Leu Val Ala Lys Leu Val Thr
        1710                1715                1720 caa gaa atg ttc caa aat att gat aag aaa att gaa agt cag aga att         5954
Gln Glu Met Phe Gln Asn Ile Asp Lys Lys Ile Glu Ser Gln Arg Ile
1725                1730                1735                1740 atg aaa gtg gag ttt act cag tgt tca atg aat gtg gtc tcc aaa acg         6002
Met Lys Val Glu Phe Thr Gln Cys Ser Met Asn Val Val Ser Lys Thr
                1745                1750                1755 ctt ttt aga aag agt ccc att tat cat cac att gat aaa acc atg att         6050
Leu Phe Arg Lys Ser Pro Ile Tyr His His Ile Asp Lys Thr Met Ile
        1760                1765                1770
```

```
aat ttt cct gca gct atg ccc ttt tct aaa gct gaa att gat cca atg    6098
Asn Phe Pro Ala Ala Met Pro Phe Ser Lys Ala Glu Ile Asp Pro Met
            1775                1780                1785 gct gtg atg tta tct aag tat tca tta cct att gta gaa gaa cca gag    6146
Ala Val Met Leu Ser Lys Tyr Ser Leu Pro Ile Val Glu Glu Pro Glu
            1790                1795                1800 gat tat aaa gag gct tca att ttt tat caa aat aaa ata gtg ggt aag    6194
Asp Tyr Lys Glu Ala Ser Ile Phe Tyr Gln Asn Lys Ile Val Gly Lys
1805                1810                1815                1820 act cag tta gtt gat gat ttt tta gat ctt gat atg gcc att aca ggg    6242
Thr Gln Leu Val Asp Asp Phe Leu Asp Leu Asp Met Ala Ile Thr Gly
                1825                1830                1835 gcc cca gga att gat gct atc aac atg gat tca tct cct gga ttt cct    6290
Ala Pro Gly Ile Asp Ala Ile Asn Met Asp Ser Ser Pro Gly Phe Pro
            1840                1845                1850 tat gtc cag gag aag ttg acc aaa aga gat tta att tgg ttg gat gaa    6338
Tyr Val Gln Glu Lys Leu Thr Lys Arg Asp Leu Ile Trp Leu Asp Glu
            1855                1860                1865 aat ggt tta ttg ctg gga gtt cat cca aga ttg gct cag aga atc tta    6386
Asn Gly Leu Leu Leu Gly Val His Pro Arg Leu Ala Gln Arg Ile Leu
            1870                1875                1880 ttc aat act gtc atg atg gaa aat tgt tct gat ttg gat gtt gtt ttt    6434
Phe Asn Thr Val Met Met Glu Asn Cys Ser Asp Leu Asp Val Val Phe
1885                1890                1895                1900 aca acc tgt cca aaa gat gaa ttg aga cca tta gag aaa gtg ttg gaa    6482
Thr Thr Cys Pro Lys Asp Glu Leu Arg Pro Leu Glu Lys Val Leu Glu
                1905                1910                1915 tca aaa aca aga gct att gat gct tgt cct ctg gat tac tca att ttg    6530
Ser Lys Thr Arg Ala Ile Asp Ala Cys Pro Leu Asp Tyr Ser Ile Leu
            1920                1925                1930 tgc cga atg tat tgg ggt cca gct att agt tat ttt cat ttg aat cca    6578
Cys Arg Met Tyr Trp Gly Pro Ala Ile Ser Tyr Phe His Leu Asn Pro
            1935                1940                1945 ggt ttc cat aca ggt gtt gct att ggc ata gat cct gat aga cag tgg    6626
Gly Phe His Thr Gly Val Ala Ile Gly Ile Asp Pro Asp Arg Gln Trp
            1950                1955                1960 gat gaa tta ttt aaa aca atg ata aga ttc gga gat gtt ggt ctt gat    6674
Asp Glu Leu Phe Lys Thr Met Ile Arg Phe Gly Asp Val Gly Leu Asp
1965                1970                1975                1980 tta gat ttc tct gct ttt gat gct agt ctt agt cca ttt atg att aga    6722
Leu Asp Phe Ser Ala Phe Asp Ala Ser Leu Ser Pro Phe Met Ile Arg
                1985                1990                1995 gaa gca ggt aga atc atg agt gaa cta tct gga act cca tcc cat ttt    6770
Glu Ala Gly Arg Ile Met Ser Glu Leu Ser Gly Thr Pro Ser His Phe
            2000                2005                2010 ggc aca gct ctt atc aat act atc att tat tcc aag cat ttg ctg tat    6818
Gly Thr Ala Leu Ile Asn Thr Ile Ile Tyr Ser Lys His Leu Leu Tyr
            2015                2020                2025 aac tgt tgt tac cat gtc tgt ggt tca atg ccc tct ggg tct cct tgt    6866
Asn Cys Cys Tyr His Val Cys Gly Ser Met Pro Ser Gly Ser Pro Cys
            2030                2035                2040 aca gct ttg cta aat tca att att aat aat gtc aat ttg tat tat gtg    6914
Thr Ala Leu Leu Asn Ser Ile Ile Asn Asn Val Asn Leu Tyr Tyr Val
2045                2050                2055                2060 ttt tcc aag ata ttt gga aag tct cca gtt ttc ttt tgt cag gct ttg    6962
Phe Ser Lys Ile Phe Gly Lys Ser Pro Val Phe Phe Cys Gln Ala Leu
                2065                2070                2075 aag att ctc tgt tat gga gat gat gtt tta ata gtt ttc tct cga gat    7010
Lys Ile Leu Cys Tyr Gly Asp Asp Val Leu Ile Val Phe Ser Arg Asp
            2080                2085                2090
```

-continued

```
gtt cag att gat aat ctt gat ttg att gga caa aaa att gta gat gag     7058
Val Gln Ile Asp Asn Leu Asp Leu Ile Gly Gln Lys Ile Val Asp Glu
        2095                2100                2105 ttt aag aaa ctt ggc atg aca gct act tct gct gac aag aat gta cct     7106
Phe Lys Lys Leu Gly Met Thr Ala Thr Ser Ala Asp Lys Asn Val Pro
    2110                2115                2120 cag ctg aaa cca gtt tcg gaa ttg act ttt ctc aaa aga tct ttc aat     7154
Gln Leu Lys Pro Val Ser Glu Leu Thr Phe Leu Lys Arg Ser Phe Asn
2125                2130                2135                2140 ttg gta gag gat aga att aga cct gca att tcg gaa aaa aca att tgg     7202
Leu Val Glu Asp Arg Ile Arg Pro Ala Ile Ser Glu Lys Thr Ile Trp
                2145                2150                2155 tct tta ata gca tgg cag aga agt aac gct gag ttt gag cag aat tta     7250
Ser Leu Ile Ala Trp Gln Arg Ser Asn Ala Glu Phe Glu Gln Asn Leu
            2160                2165                2170 gaa aat gct cag tgg ttt gct ttt atg cat ggc tat gag ttt tat cag     7298
Glu Asn Ala Gln Trp Phe Ala Phe Met His Gly Tyr Glu Phe Tyr Gln
        2175                2180                2185 aaa ttt tat tat ttt gtt cag tcc tgt ttg gag aaa gag atg ata gaa     7346
Lys Phe Tyr Tyr Phe Val Gln Ser Cys Leu Glu Lys Glu Met Ile Glu
    2190                2195                2200 tac aga ctt aaa tct tat gat tgg tgg aga atg aga ttt tat gac cag     7394
Tyr Arg Leu Lys Ser Tyr Asp Trp Trp Arg Met Arg Phe Tyr Asp Gln
2205                2210                2215                2220 tgt ttc att tgt gac ctt tca tgatttgttt aaacaaattt tcttaaaatt       7445
Cys Phe Ile Cys Asp Leu Ser
                2225 tctgaggttt gtttatttct tttatcagta aataaaaaaa aaaaaaaa                7493

<210> SEQ ID NO 2
<211> LENGTH: 2227
<212> TYPE: PRT
<213> ORGANISM: WILD-TYPE HUMAN HEPATITIS A VIRUS, STRAIN HM-175

<400> SEQUENCE: 2

Met Asn Met Ser Arg Gln Gly Ile Phe Gln Thr Val Gly Ser Gly Leu
  1               5                  10                  15

Asp His Ile Leu Ser Leu Ala Asp Ile Glu Glu Glu Gln Met Ile Gln
            20                  25                  30

Ser Val Asp Arg Thr Ala Val Thr Gly Ala Ser Tyr Phe Thr Ser Val
        35                  40                  45

Asp Gln Ser Ser Val His Thr Ala Glu Val Gly Ser His Gln Val Glu
    50                  55                  60

Pro Leu Arg Thr Ser Val Asp Lys Pro Gly Ser Lys Lys Thr Gln Gly
 65                  70                  75                  80

Glu Lys Phe Phe Leu Ile His Ser Ala Asp Trp Leu Thr Thr His Ala
                85                  90                  95

Leu Phe His Glu Val Ala Lys Leu Asp Val Val Lys Leu Leu Tyr Asn
            100                 105                 110

Glu Gln Phe Ala Val Gln Gly Leu Leu Arg Tyr His Thr Tyr Ala Arg
        115                 120                 125

Phe Gly Ile Glu Ile Gln Val Gln Ile Asn Pro Thr Pro Phe Gln Gln
    130                 135                 140

Gly Gly Leu Ile Cys Ala Met Val Pro Gly Asp Gln Ser Tyr Gly Ser
145                 150                 155                 160

Ile Ala Ser Leu Thr Val Tyr Pro His Gly Leu Leu Asn Cys Asn Ile
                165                 170                 175
```

-continued

```
Asn Asn Val Val Arg Ile Lys Val Pro Phe Ile Tyr Thr Arg Gly Ala
            180                 185                 190

Tyr His Phe Lys Asp Pro Gln Tyr Pro Val Trp Glu Leu Thr Ile Arg
        195                 200                 205

Val Trp Ser Glu Leu Asn Ile Gly Thr Gly Thr Ser Ala Tyr Thr Ser
    210                 215                 220

Leu Asn Val Leu Ala Arg Phe Thr Asp Leu Glu Leu His Gly Leu Thr
225                 230                 235                 240

Pro Leu Ser Thr Gln Met Met Arg Asn Glu Phe Arg Val Ser Thr Thr
                245                 250                 255

Glu Asn Val Val Asn Leu Ser Asn Tyr Glu Asp Ala Arg Ala Lys Met
            260                 265                 270

Ser Phe Ala Leu Asp Gln Glu Asp Trp Lys Ser Asp Pro Ser Gln Gly
        275                 280                 285

Gly Gly Ile Lys Ile Thr His Phe Thr Thr Trp Thr Ser Ile Pro Thr
    290                 295                 300

Leu Ala Ala Gln Phe Pro Phe Asn Ala Ser Asp Ser Val Gly Gln Gln
305                 310                 315                 320

Ile Lys Val Ile Pro Val Asp Pro Tyr Phe Phe Gln Met Thr Asn Thr
                325                 330                 335

Asn Pro Asp Gln Lys Cys Ile Thr Ala Leu Ala Ser Ile Cys Gln Met
            340                 345                 350

Phe Cys Phe Trp Arg Gly Asp Leu Val Phe Asp Phe Gln Val Phe Pro
        355                 360                 365

Thr Lys Tyr His Ser Gly Arg Leu Leu Phe Cys Phe Val Pro Gly Asn
    370                 375                 380

Glu Leu Ile Asp Val Ser Gly Ile Thr Leu Lys Gln Ala Thr Thr Ala
385                 390                 395                 400

Pro Cys Ala Val Met Asp Ile Thr Gly Val Gln Ser Thr Leu Arg Phe
                405                 410                 415

Arg Val Pro Trp Ile Ser Asp Thr Pro Tyr Arg Val Asn Arg Tyr Thr
            420                 425                 430

Lys Ser Ala His Gln Lys Gly Glu Tyr Thr Ala Ile Gly Lys Leu Ile
        435                 440                 445

Val Tyr Cys Tyr Asn Arg Leu Thr Ser Pro Ser Asn Val Ala Ser His
    450                 455                 460

Val Arg Val Asn Val Tyr Leu Ser Ala Ile Asn Leu Glu Cys Phe Ala
465                 470                 475                 480

Pro Leu Tyr His Ala Met Asp Val Thr Thr Gln Val Gly Asp Asp Ser
                485                 490                 495

Gly Gly Phe Ser Thr Thr Val Ser Thr Glu Gln Asn Val Pro Asp Pro
            500                 505                 510

Gln Val Gly Ile Thr Thr Met Lys Asp Leu Lys Gly Lys Ala Asn Arg
        515                 520                 525

Gly Lys Met Asp Val Ser Gly Val Gln Ala Pro Val Gly Ala Ile Thr
    530                 535                 540

Thr Ile Glu Asp Pro Val Leu Ala Lys Lys Val Pro Glu Thr Phe Pro
545                 550                 555                 560

Glu Leu Lys Pro Gly Glu Ser Arg His Thr Ser Asp His Met Ser Ile
                565                 570                 575

Tyr Lys Phe Met Gly Arg Ser His Phe Leu Cys Thr Phe Thr Phe Asn
            580                 585                 590
```

-continued

```
Ser Asn Asn Lys Glu Tyr Thr Phe Pro Ile Thr Leu Ser Ser Thr Ser
            595                 600                 605

Asn Pro Pro His Gly Leu Pro Ser Thr Leu Arg Trp Phe Asn Leu
    610                 615                 620

Phe Gln Leu Tyr Arg Gly Pro Leu Asp Leu Thr Ile Ile Thr Gly
625                 630                 635                 640

Ala Thr Asp Val Asp Gly Met Ala Trp Phe Thr Pro Val Gly Leu Ala
                645                 650                 655

Val Asp Thr Pro Trp Val Glu Lys Glu Ser Ala Leu Ser Ile Asp Tyr
                660                 665                 670

Lys Thr Ala Leu Gly Ala Val Arg Phe Asn Thr Arg Arg Thr Gly Asn
            675                 680                 685

Ile Gln Ile Arg Leu Pro Trp Tyr Ser Tyr Leu Tyr Ala Val Ser Gly
            690                 695                 700

Ala Leu Asp Gly Leu Gly Asp Lys Thr Asp Ser Thr Phe Gly Leu Val
705                 710                 715                 720

Ser Ile Gln Ile Ala Asn Tyr Asn His Ser Asp Glu Tyr Leu Ser Phe
                725                 730                 735

Ser Cys Tyr Leu Ser Val Thr Glu Gln Ser Glu Phe Tyr Phe Pro Arg
                740                 745                 750

Ala Pro Leu Asn Ser Asn Ala Met Leu Ser Thr Glu Ser Met Met Ser
            755                 760                 765

Arg Ile Ala Ala Gly Asp Leu Glu Ser Ser Val Asp Asp Pro Arg Ser
770                 775                 780

Glu Glu Asp Lys Arg Phe Glu Ser His Ile Glu Cys Arg Lys Pro Tyr
785                 790                 795                 800

Lys Glu Leu Arg Leu Glu Val Gly Lys Gln Arg Leu Lys Tyr Ala Gln
                805                 810                 815

Glu Glu Leu Ser Asn Glu Val Leu Pro Pro Arg Lys Met Lys Gly
            820                 825                 830

Leu Phe Ser Gln Ala Lys Ile Ser Leu Phe Tyr Thr Glu Glu His Glu
            835                 840                 845

Ile Met Lys Phe Ser Trp Arg Gly Val Thr Ala Asp Thr Arg Ala Leu
850                 855                 860

Arg Arg Phe Gly Phe Ser Leu Ala Ala Gly Arg Ser Val Trp Thr Leu
865                 870                 875                 880

Glu Met Asp Ala Gly Val Leu Thr Gly Arg Leu Ile Arg Leu Asn Asp
                885                 890                 895

Glu Lys Trp Thr Glu Met Lys Asp Asp Lys Ile Val Ser Leu Ile Glu
            900                 905                 910

Lys Phe Thr Ser Asn Lys Tyr Trp Ser Lys Val Asn Phe Pro His Gly
            915                 920                 925

Met Leu Asp Leu Glu Glu Ile Ala Ala Asn Ser Lys Asp Phe Pro Asn
    930                 935                 940

Met Ser Glu Thr Asp Leu Cys Phe Leu Leu His Trp Leu Asn Pro Lys
945                 950                 955                 960

Lys Ile Asn Leu Ala Asp Arg Met Leu Gly Leu Ser Gly Val Gln Glu
                965                 970                 975

Ile Lys Glu Gln Gly Val Gly Leu Ile Ala Glu Cys Arg Thr Phe Leu
            980                 985                 990

Asp Ser Ile Ala Gly Thr Leu Lys Ser Met Met Phe Gly Phe His His
            995                 1000                1005

Ser Val Thr Val Glu Ile Ile Asn Thr Val Leu Cys Phe Val Lys Ser
```

-continued

```
            1010                1015                1020
Gly Ile Leu Leu Tyr Val Ile Gln Gln Leu Asn Gln Asp Glu His Ser
1025                1030                1035                1040

His Ile Ile Gly Leu Leu Arg Val Met Asn Tyr Ala Asp Ile Gly Cys
                1045                1050                1055

Ser Val Ile Ser Cys Gly Lys Val Phe Ser Lys Met Leu Glu Thr Val
                1060                1065                1070

Phe Asn Trp Gln Met Asp Ser Arg Met Met Glu Leu Arg Thr Gln Ser
                1075                1080                1085

Phe Ser Asn Trp Leu Arg Asp Ile Cys Ser Gly Ile Thr Ile Phe Lys
                1090                1095                1100

Asn Phe Lys Asp Ala Ile Tyr Trp Leu Tyr Thr Lys Leu Lys Asp Phe
1105                1110                1115                1120

Tyr Glu Val Asn Tyr Gly Lys Lys Lys Asp Ile Leu Asn Ile Leu Lys
                1125                1130                1135

Asp Asn Gln Gln Lys Ile Glu Lys Ala Ile Glu Glu Ala Asp Glu Phe
                1140                1145                1150

Cys Ile Leu Gln Ile Gln Asp Val Glu Lys Phe Glu Gln Tyr Gln Lys
                1155                1160                1165

Gly Val Asp Leu Ile Gln Lys Leu Arg Thr Val His Ser Met Ala Gln
                1170                1175                1180

Val Asp Pro Asn Leu Met Val His Leu Ser Pro Leu Arg Asp Cys Ile
1185                1190                1195                1200

Ala Arg Val His Gln Lys Leu Lys Asn Leu Gly Ser Ile Asn Gln Ala
                1205                1210                1215

Met Val Thr Arg Cys Glu Pro Val Val Cys Tyr Leu Tyr Gly Lys Arg
                1220                1225                1230

Gly Gly Gly Lys Ser Leu Thr Ser Ile Ala Leu Ala Thr Lys Ile Cys
                1235                1240                1245

Lys His Tyr Gly Val Glu Pro Glu Lys Asn Ile Tyr Thr Lys Pro Val
                1250                1255                1260

Ala Ser Asp Tyr Trp Asp Gly Tyr Ser Gly Gln Leu Val Cys Ile Ile
1265                1270                1275                1280

Asp Asp Ile Gly Gln Asn Thr Thr Asp Glu Asp Trp Ser Asp Phe Cys
                1285                1290                1295

Gln Leu Val Ser Gly Cys Pro Met Arg Leu Asn Met Ala Ser Leu Glu
                1300                1305                1310

Glu Lys Gly Arg His Phe Ser Ser Pro Phe Ile Ile Ala Thr Ser Asn
                1315                1320                1325

Trp Ser Asn Pro Ser Pro Lys Thr Val Tyr Val Lys Glu Ala Ile Asp
                1330                1335                1340

Arg Arg Leu His Phe Lys Val Glu Val Lys Pro Ala Ser Phe Phe Lys
1345                1350                1355                1360

Asn Pro His Asn Asp Met Leu Asn Val Asn Leu Ala Lys Thr Asn Asp
                1365                1370                1375

Ala Ile Lys Asp Met Ser Cys Val Asp Leu Ile Met Asp Gly His Asn
                1380                1385                1390

Val Ser Leu Met Asp Leu Leu Ser Ser Leu Val Met Thr Val Glu Ile
                1395                1400                1405

Arg Lys Gln Asn Met Thr Glu Phe Met Glu Leu Trp Ser Gln Gly Ile
                1410                1415                1420

Ser Asp Asp Asp Asn Asp Ser Ala Val Ala Glu Phe Phe Gln Ser Phe
1425                1430                1435                1440
```

-continued

```
Pro Ser Gly Glu Pro Ser Asn Ser Lys Leu Ser Gly Phe Phe Gln Ser
            1445                1450                1455
Val Thr Asn His Lys Trp Val Ala Val Gly Ala Ala Val Gly Ile Leu
            1460                1465                1470
Gly Val Leu Val Gly Gly Trp Phe Val Tyr Lys His Phe Ser Arg Lys
            1475                1480                1485
Glu Glu Glu Pro Ile Pro Ala Glu Gly Val Tyr His Gly Val Thr Lys
            1490                1495                1500
Pro Lys Gln Val Ile Lys Leu Asp Ala Asp Pro Val Glu Ser Gln Ser
1505                1510                1515                1520
Thr Leu Glu Ile Ala Gly Leu Val Arg Lys Asn Leu Val Gln Phe Gly
            1525                1530                1535
Val Gly Glu Lys Asn Gly Cys Val Arg Trp Val Met Asn Ala Leu Gly
            1540                1545                1550
Val Lys Asp Asp Trp Leu Leu Val Pro Ser His Ala Tyr Lys Phe Glu
            1555                1560                1565
Lys Asp Tyr Glu Met Met Glu Phe Tyr Phe Asn Arg Gly Gly Thr Tyr
            1570                1575                1580
Tyr Ser Ile Ser Ala Gly Asn Val Val Ile Gln Ser Leu Asp Val Gly
1585                1590                1595                1600
Phe Gln Asp Val Val Leu Met Lys Val Pro Thr Ile Pro Lys Phe Arg
            1605                1610                1615
Asp Ile Thr Gln His Phe Ile Lys Lys Gly Asp Val Pro Arg Ala Leu
            1620                1625                1630
Asn Arg Leu Ala Thr Leu Val Thr Thr Val Asn Gly Thr Pro Met Leu
            1635                1640                1645
Ile Ser Glu Gly Pro Leu Lys Met Glu Glu Lys Ala Thr Tyr Val His
            1650                1655                1660
Lys Lys Asn Asp Gly Thr Thr Val Asp Leu Thr Val Asp Gln Ala Trp
1665                1670                1675                1680
Arg Gly Lys Gly Glu Gly Leu Pro Gly Met Cys Gly Gly Ala Leu Val
            1685                1690                1695
Ser Ser Asn Gln Ser Ile Gln Asn Ala Ile Leu Gly Ile His Val Ala
            1700                1705                1710
Gly Gly Asn Ser Ile Leu Val Ala Lys Leu Val Thr Gln Glu Met Phe
            1715                1720                1725
Gln Asn Ile Asp Lys Lys Ile Glu Ser Gln Arg Ile Met Lys Val Glu
            1730                1735                1740
Phe Thr Gln Cys Ser Met Asn Val Val Ser Lys Thr Leu Phe Arg Lys
1745                1750                1755                1760
Ser Pro Ile Tyr His His Ile Asp Lys Thr Met Ile Asn Phe Pro Ala
            1765                1770                1775
Ala Met Pro Phe Ser Lys Ala Glu Ile Asp Pro Met Ala Val Met Leu
            1780                1785                1790
Ser Lys Tyr Ser Leu Pro Ile Val Glu Glu Pro Glu Asp Tyr Lys Glu
            1795                1800                1805
Ala Ser Ile Phe Tyr Gln Asn Lys Ile Val Gly Lys Thr Gln Leu Val
            1810                1815                1820
Asp Asp Phe Leu Asp Leu Asp Met Ala Ile Thr Gly Ala Pro Gly Ile
1825                1830                1835                1840
Asp Ala Ile Asn Met Asp Ser Ser Pro Gly Phe Pro Tyr Val Gln Glu
            1845                1850                1855
```

```
Lys Leu Thr Lys Arg Asp Leu Ile Trp Leu Asp Glu Asn Gly Leu Leu
            1860                1865                1870

Leu Gly Val His Pro Arg Leu Ala Gln Arg Ile Leu Phe Asn Thr Val
        1875                1880                1885

Met Met Glu Asn Cys Ser Asp Leu Asp Val Val Phe Thr Thr Cys Pro
    1890                1895                1900

Lys Asp Glu Leu Arg Pro Leu Glu Lys Val Leu Glu Ser Lys Thr Arg
1905                1910                1915                1920

Ala Ile Asp Ala Cys Pro Leu Asp Tyr Ser Ile Leu Cys Arg Met Tyr
                1925                1930                1935

Trp Gly Pro Ala Ile Ser Tyr Phe His Leu Asn Pro Gly Phe His Thr
            1940                1945                1950

Gly Val Ala Ile Gly Ile Asp Pro Asp Arg Gln Trp Asp Glu Leu Phe
        1955                1960                1965

Lys Thr Met Ile Arg Phe Gly Asp Val Gly Leu Asp Leu Asp Phe Ser
    1970                1975                1980

Ala Phe Asp Ala Ser Leu Ser Pro Phe Met Ile Arg Glu Ala Gly Arg
1985                1990                1995                2000

Ile Met Ser Glu Leu Ser Gly Thr Pro Ser His Phe Gly Thr Ala Leu
                2005                2010                2015

Ile Asn Thr Ile Ile Tyr Ser Lys His Leu Leu Tyr Asn Cys Cys Tyr
            2020                2025                2030

His Val Cys Gly Ser Met Pro Ser Gly Ser Pro Cys Thr Ala Leu Leu
        2035                2040                2045

Asn Ser Ile Ile Asn Asn Val Asn Leu Tyr Tyr Val Phe Ser Lys Ile
    2050                2055                2060

Phe Gly Lys Ser Pro Val Phe Phe Cys Gln Ala Leu Lys Ile Leu Cys
1065                2070                2075                2080

Tyr Gly Asp Asp Val Leu Ile Val Phe Ser Arg Asp Val Gln Ile Asp
                2085                2090                2095

Asn Leu Asp Leu Ile Gly Gln Lys Ile Val Asp Glu Phe Lys Lys Leu
            2100                2105                2110

Gly Met Thr Ala Thr Ser Ala Asp Lys Asn Val Pro Gln Leu Lys Pro
        2115                2120                2125

Val Ser Glu Leu Thr Phe Leu Lys Arg Ser Phe Asn Leu Val Glu Asp
    2130                2135                2140

Arg Ile Arg Pro Ala Ile Ser Glu Lys Thr Ile Trp Ser Leu Ile Ala
2145                2150                2155                2160

Trp Gln Arg Ser Asn Ala Glu Phe Glu Gln Asn Leu Glu Asn Ala Gln
                2165                2170                2175

Trp Phe Ala Phe Met His Gly Tyr Glu Phe Tyr Gln Lys Phe Tyr Tyr
            2180                2185                2190

Phe Val Gln Ser Cys Leu Glu Lys Glu Met Ile Glu Tyr Arg Leu Lys
        2195                2200                2205

Ser Tyr Asp Trp Trp Arg Met Arg Phe Tyr Asp Gln Cys Phe Ile Cys
    2210                2215                2220

Asp Leu Ser
2225

<210> SEQ ID NO 3
<211> LENGTH: 7488
<212> TYPE: DNA
<213> ORGANISM: Attenuated (Pass 35) HAV, strain HM-175
<220> FEATURE:
<221> NAME/KEY: CDS
```

-continued

<222> LOCATION: (730)..(7410)

<400> SEQUENCE: 3

```
ttcaagaggg gtctccggga atttccggag tccctcttgg aagtccatgg tgagggact      60
tgatacctca ccgccgtttg cctaggctat aggctaaatt ttcccttcc cttttcccctt   120
tcccattccc ttttgcttgt aaatattgat tcctgcaggt tcagggttct taaatctgtt   180
tctctataag aacactcatt ttcacgcttt ctgtcttctt tcttccaggg ctctccccttt  240
gccctaggct ctggccgttg cgcccggcgg ggtcaactcc atgattagca tggagctgta   300
ggagtctaaa ttggggacac agatgtttgg aacgtcacct tgcagtgtta acttggcttt   360
catgaatctc tttgatcttc cacaaggggt aggctacggg tgaaacctct taggctaata   420
cttctatgaa gagatgcctt ggatagggta acagcggcgg atattggtga gttgttaaga   480
caaaaaccat tcaacgccgg aggactgact ctcatccagt ggatgcattg agtggattga   540
ctgtcagggc tgtctttagg cttaattcca gacctctctg tgcttagggc aaacatcatt   600
tggccttaaa tgggattctg tgagagggga tccctccatt gacagctgga ctgttctttg   660
gggccttatg tggtgtttgc ctctgaggta ctcaggggca tttaggtttt tcctcattct   720 taaataata atg aac atg tct aga caa ggt att ttc cag act gtt ggg agt   771
              Met Asn Met Ser Arg Gln Gly Ile Phe Gln Thr Val Gly Ser
                1               5                  10 ggt ctt gac cac atc ctg tct ttg gca gac att gag gaa gag caa atg     819
Gly Leu Asp His Ile Leu Ser Leu Ala Asp Ile Glu Glu Glu Gln Met
 15                  20                  25                  30 att caa tca gtt gat agg act gca gtg act ggt gct tct tat ttt act     867
Ile Gln Ser Val Asp Arg Thr Ala Val Thr Gly Ala Ser Tyr Phe Thr
                 35                  40                  45 tct gtg gat caa tct tca gtt cat aca gct gag gtt gga tca cac cag     915
Ser Val Asp Gln Ser Ser Val His Thr Ala Glu Val Gly Ser His Gln
             50                  55                  60 gtt gaa cct ttg aga acc tct gtt gat aaa ccc ggt tca aag agg act     963
Val Glu Pro Leu Arg Thr Ser Val Asp Lys Pro Gly Ser Lys Arg Thr
 65                  70                  75 cag gga gag aaa ttt ttc ttg att cat tct gca gat tgg ctt act aca    1011
Gln Gly Glu Lys Phe Phe Leu Ile His Ser Ala Asp Trp Leu Thr Thr
         80                  85                  90 cat gct ctt ttc cat gaa gtt gca aaa ttg gat gtg gtg aaa tta tta    1059
His Ala Leu Phe His Glu Val Ala Lys Leu Asp Val Val Lys Leu Leu
 95                 100                 105                 110 tac aat gag cag ttt gct gtt caa ggg ttg ttg aga tac cat aca tat    1107
Tyr Asn Glu Gln Phe Ala Val Gln Gly Leu Leu Arg Tyr His Thr Tyr
                115                 120                 125 gca aga ttt ggc att gaa att caa gtt cag ata aac cct aca cct ttc    1155
Ala Arg Phe Gly Ile Glu Ile Gln Val Gln Ile Asn Pro Thr Pro Phe
            130                 135                 140 caa cag ggg gga ttg atc tgt gct atg gtt cct ggt gac cag agc tat    1203
Gln Gln Gly Gly Leu Ile Cys Ala Met Val Pro Gly Asp Gln Ser Tyr
145                 150                 155 ggt tct ata gca tca ttg act gtt tat cct cat ggt ttg tta aat tgc    1251
Gly Ser Ile Ala Ser Leu Thr Val Tyr Pro His Gly Leu Leu Asn Cys
        160                 165                 170 aat att aac aat gtg gtt aga ata aag gtt cca ttt att tac aca aga    1299
Asn Ile Asn Asn Val Val Arg Ile Lys Val Pro Phe Ile Tyr Thr Arg
175                 180                 185                 190 ggt gct tac cac ttt aaa gat cca caa tac cca gtt tgg gaa ttg aca    1347
Gly Ala Tyr His Phe Lys Asp Pro Gln Tyr Pro Val Trp Glu Leu Thr
                195                 200                 205
```

-continued

```
att aga gtt tgg tca gaa tta aat att ggg aca gga act tca gct tat      1395
Ile Arg Val Trp Ser Glu Leu Asn Ile Gly Thr Gly Thr Ser Ala Tyr
        210                 215                 220 act tca ctc aat gtt tta gct aga ttt aca gat ttg gag ttg cat gga      1443
Thr Ser Leu Asn Val Leu Ala Arg Phe Thr Asp Leu Glu Leu His Gly
225                 230                 235 tta act cct ctt tct aca caa atg atg aga aat gaa ttt agg gtc agt      1491
Leu Thr Pro Leu Ser Thr Gln Met Met Arg Asn Glu Phe Arg Val Ser
    240                 245                 250 act act gag aat gtg gtg aat ctg tca aat tat gaa gat gca aga gca      1539
Thr Thr Glu Asn Val Val Asn Leu Ser Asn Tyr Glu Asp Ala Arg Ala
255                 260                 265                 270 aag atg tct ttt gct ttg gat cag gaa gat tgg aaa tct gat ccg tcc      1587
Lys Met Ser Phe Ala Leu Asp Gln Glu Asp Trp Lys Ser Asp Pro Ser
                275                 280                 285 cag ggt ggt ggg atc aaa att act cat ttt act act tgg aca tct att      1635
Gln Gly Gly Gly Ile Lys Ile Thr His Phe Thr Thr Trp Thr Ser Ile
            290                 295                 300 cca act ttg gct gct cag ttt cca ttt aat gct tca gac tca gtt ggt      1683
Pro Thr Leu Ala Ala Gln Phe Pro Phe Asn Ala Ser Asp Ser Val Gly
        305                 310                 315 caa caa att aaa gtt att cca gtt gac cca tat ttt ttc caa atg aca      1731
Gln Gln Ile Lys Val Ile Pro Val Asp Pro Tyr Phe Phe Gln Met Thr
    320                 325                 330 aat aca aat cct gac caa aaa tgt ata act gct ttg gct tct att tgt      1779
Asn Thr Asn Pro Asp Gln Lys Cys Ile Thr Ala Leu Ala Ser Ile Cys
335                 340                 345                 350 cag atg ttt tgt ttt tgg aga gga gat ctt gtc ttt gat ttt caa gtt      1827
Gln Met Phe Cys Phe Trp Arg Gly Asp Leu Val Phe Asp Phe Gln Val
                355                 360                 365 ttt ccc acc aaa tat cat tca ggt aga tta ctg ttt tgt ttt gtt cct      1875
Phe Pro Thr Lys Tyr His Ser Gly Arg Leu Leu Phe Cys Phe Val Pro
            370                 375                 380 ggc aat gag cta ata gat gtt tct gga atc aca tta aag caa gca act      1923
Gly Asn Glu Leu Ile Asp Val Ser Gly Ile Thr Leu Lys Gln Ala Thr
        385                 390                 395 act gct cct tgt gca gta atg gat att aca gga gtg cag tca act ttg      1971
Thr Ala Pro Cys Ala Val Met Asp Ile Thr Gly Val Gln Ser Thr Leu
    400                 405                 410 aga ttt cgt gtt ccc tgg att tct gac act cct tac aga gtg aac agg      2019
Arg Phe Arg Val Pro Trp Ile Ser Asp Thr Pro Tyr Arg Val Asn Arg
415                 420                 425                 430 tat aca aag tca gca cat cag aaa ggt gag tac act gcc att ggg aag      2067
Tyr Thr Lys Ser Ala His Gln Lys Gly Glu Tyr Thr Ala Ile Gly Lys
                435                 440                 445 ctt att gtg tat tgt tat aac aga ttg acc tct cct tct aac gtt gct      2115
Leu Ile Val Tyr Cys Tyr Asn Arg Leu Thr Ser Pro Ser Asn Val Ala
            450                 455                 460 tcc cat gtc aga gtg aat gtt tat ctt tca gca att aac ttg gaa tgt      2163
Ser His Val Arg Val Asn Val Tyr Leu Ser Ala Ile Asn Leu Glu Cys
        465                 470                 475 ttt gct cct ctt tat cat gct atg gat gtt act aca caa gtt gga gat      2211
Phe Ala Pro Leu Tyr His Ala Met Asp Val Thr Thr Gln Val Gly Asp
    480                 485                 490 gat tct gga ggt ttt tca aca aca gtt tct aca gaa cag aat gtt cca      2259
Asp Ser Gly Gly Phe Ser Thr Thr Val Ser Thr Glu Gln Asn Val Pro
495                 500                 505                 510 gat ccc caa gtt ggt ata aca acc atg aaa gat ttg aaa gga aaa gct      2307
Asp Pro Gln Val Gly Ile Thr Thr Met Lys Asp Leu Lys Gly Lys Ala
```

-continued

|  |  | 515 |  |  |  | 520 |  |  |  | 525 |  |  |  |  |
|---|---|---|---|---|---|---|---|---|---|---|---|---|---|---|
| aac | aga | ggg | aaa | atg | gat | gtt | tca | gga | gta | caa | gca | cct | gtg | gga | gct | 2355 |
| Asn | Arg | Gly | Lys | Met | Asp | Val | Ser | Gly | Val | Gln | Ala | Pro | Val | Gly | Ala |  |
|  |  | 530 |  |  |  | 535 |  |  |  | 540 |  |  |  |  |

```
aac aga ggg aaa atg gat gtt tca gga gta caa gca cct gtg gga gct    2355
Asn Arg Gly Lys Met Asp Val Ser Gly Val Gln Ala Pro Val Gly Ala
            530                 535                 540 atc aca aca att gag gat cca gtt tta gca aag aaa gta cct gag aca    2403
Ile Thr Thr Ile Glu Asp Pro Val Leu Ala Lys Lys Val Pro Glu Thr
                545                 550                 555 ttt cct gaa ttg aaa cct gga gaa tcc aga cat aca tca gat cat atg    2451
Phe Pro Glu Leu Lys Pro Gly Glu Ser Arg His Thr Ser Asp His Met
    560                 565                 570 tcc atc tac aag ttt atg gga agg tct cat ttc ttg tgc act ttt aca    2499
Ser Ile Tyr Lys Phe Met Gly Arg Ser His Phe Leu Cys Thr Phe Thr
575                 580                 585                 590 ttc aat tca aat aat aaa gag tac aca ttt cct ata acc ttg tct tca    2547
Phe Asn Ser Asn Asn Lys Glu Tyr Thr Phe Pro Ile Thr Leu Ser Ser
                595                 600                 605 acc tct aat cct cct cat ggt ttg cca tca aca ctg agg tgg ttt ttc    2595
Thr Ser Asn Pro Pro His Gly Leu Pro Ser Thr Leu Arg Trp Phe Phe
            610                 615                 620 aac ttg ttt cag ttg tat aga ggg cct tta gat ctg aca att att att    2643
Asn Leu Phe Gln Leu Tyr Arg Gly Pro Leu Asp Leu Thr Ile Ile Ile
        625                 630                 635 aca gga gca act gat gta gat ggc atg gcc tgg ttc act cca gta ggt    2691
Thr Gly Ala Thr Asp Val Asp Gly Met Ala Trp Phe Thr Pro Val Gly
640                 645                 650 ctt gcc gtt gat act cct tgg gta gag aag gag tca gct ttg tct att    2739
Leu Ala Val Asp Thr Pro Trp Val Glu Lys Glu Ser Ala Leu Ser Ile
655                 660                 665                 670 gac tac aaa act gct ctt gga gct gtc aga ttt aac aca agg aga aca    2787
Asp Tyr Lys Thr Ala Leu Gly Ala Val Arg Phe Asn Thr Arg Arg Thr
                675                 680                 685 ggg aac att cag att aga tta cca tgg tat tct tat tta tat gct gtg    2835
Gly Asn Ile Gln Ile Arg Leu Pro Trp Tyr Ser Tyr Leu Tyr Ala Val
            690                 695                 700 tct gga gca ctg gat ggt ttg gga gac aag aca gat tct aca ttt gga    2883
Ser Gly Ala Leu Asp Gly Leu Gly Asp Lys Thr Asp Ser Thr Phe Gly
        705                 710                 715 ttg gtt tct att cag att gca aat tac aat cat tct gat gaa tac ttg    2931
Leu Val Ser Ile Gln Ile Ala Asn Tyr Asn His Ser Asp Glu Tyr Leu
    720                 725                 730 tct ttt agt tgt tat ttg tct gtc aca gaa caa tca gag ttt tat ttt    2979
Ser Phe Ser Cys Tyr Leu Ser Val Thr Glu Gln Ser Glu Phe Tyr Phe
735                 740                 745                 750 ccc aga gct cca ttg aac tca aat gcc atg tta tcc act gta tca atg    3027
Pro Arg Ala Pro Leu Asn Ser Asn Ala Met Leu Ser Thr Val Ser Met
                755                 760                 765 atg agc aga att gca gct gga gac ttg gag tca tca gtg gat gat cct    3075
Met Ser Arg Ile Ala Ala Gly Asp Leu Glu Ser Ser Val Asp Asp Pro
            770                 775                 780 aga tca gag gaa gat aaa aga ttt gag agt cat ata gaa tgc agg aag    3123
Arg Ser Glu Glu Asp Lys Arg Phe Glu Ser His Ile Glu Cys Arg Lys
        785                 790                 795 cca tat aaa gaa ctg aga tta gaa gtt ggg aaa caa aga ctc aag tat    3171
Pro Tyr Lys Glu Leu Arg Leu Glu Val Gly Lys Gln Arg Leu Lys Tyr
    800                 805                 810 gct cag gaa gaa ttg tca agt gaa gta ctt cca ccc cct agg aaa atg    3219
Ala Gln Glu Glu Leu Ser Ser Glu Val Leu Pro Pro Pro Arg Lys Met
815                 820                 825                 830 aag gga ctg ttt tca caa gcc aaa att tct ctt ttt tat act gag gag    3267
```

```
                   Lys Gly Leu Phe Ser Gln Ala Lys Ile Ser Leu Phe Tyr Thr Glu Glu
                                   835                 840                 845 cat gaa ata atg aag ttt tcc tgg aga ggt gtg act gct gat act aga        3315
His Glu Ile Met Lys Phe Ser Trp Arg Gly Val Thr Ala Asp Thr Arg
                850                 855                 860 gct tta agg agg ttt gga ttc tct ttg gcc gca ggc aga agt gtg tgg        3363
Ala Leu Arg Arg Phe Gly Phe Ser Leu Ala Ala Gly Arg Ser Val Trp
            865                 870                 875 act ctt gaa atg gat gct ggg gtt ctt act ggg aga ctg att aga ttg        3411
Thr Leu Glu Met Asp Ala Gly Val Leu Thr Gly Arg Leu Ile Arg Leu
        880                 885                 890 aat gat gag aaa tgg aca gaa atg aag gat gac aag att gtt tca ttg        3459
Asn Asp Glu Lys Trp Thr Glu Met Lys Asp Asp Lys Ile Val Ser Leu
895                 900                 905                 910 att gaa aag ttt aca agt aac aaa tat tgg tcc aaa gtg aat ttc cca        3507
Ile Glu Lys Phe Thr Ser Asn Lys Tyr Trp Ser Lys Val Asn Phe Pro
                915                 920                 925 cat ggg atg ttg gat ctt gaa gaa att gct gcc aat tct aag gat ttt        3555
His Gly Met Leu Asp Leu Glu Glu Ile Ala Ala Asn Ser Lys Asp Phe
                930                 935                 940 cct aac atg tct gaa acg gat ttg tgt ttc ttg ctg cat tgg tta aat        3603
Pro Asn Met Ser Glu Thr Asp Leu Cys Phe Leu Leu His Trp Leu Asn
            945                 950                 955 cca aag aaa att aat tta gca gat aga atg ctt gga ttg tct gga gtt        3651
Pro Lys Lys Ile Asn Leu Ala Asp Arg Met Leu Gly Leu Ser Gly Val
        960                 965                 970 cag gaa att aaa gaa caa ggt gtt gga tta ata gca gag tgt aga act        3699
Gln Glu Ile Lys Glu Gln Gly Val Gly Leu Ile Ala Glu Cys Arg Thr
975                 980                 985                 990 ttc tta gat tct att gct gga act tta aaa tct atg atg ttt gga ttt        3747
Phe Leu Asp Ser Ile Ala Gly Thr Leu Lys Ser Met Met Phe Gly Phe
                995                 1000                1005 cat cat tct gtg act gtt gaa att ata aac act gtg ctc tgt ttt gtt        3795
His His Ser Val Thr Val Glu Ile Ile Asn Thr Val Leu Cys Phe Val
                1010                1015                1020 aag agt gga att ttg ctt tat gta ata caa caa ttg aat cag gat gaa        3843
Lys Ser Gly Ile Leu Leu Tyr Val Ile Gln Gln Leu Asn Gln Asp Glu
            1025                1030                1035 cat tct cac ata att ggt ttg ttg aga gtc atg aat tat gta gat att        3891
His Ser His Ile Ile Gly Leu Leu Arg Val Met Asn Tyr Val Asp Ile
        1040                1045                1050 ggt tgt tca gtt att tca tgt gcc aaa gtt ttt tcc aaa atg ctg gaa        3939
Gly Cys Ser Val Ile Ser Cys Ala Lys Val Phe Ser Lys Met Leu Glu
1055                1060                1065                1070 aca gtc ttt aat tgg caa atg gac tcc aga atg atg gag tta agg act        3987
Thr Val Phe Asn Trp Gln Met Asp Ser Arg Met Met Glu Leu Arg Thr
                1075                1080                1085 cag agt ttt tcc aac tgg tta aga gat att tgt tct ggg atc acc att        4035
Gln Ser Phe Ser Asn Trp Leu Arg Asp Ile Cys Ser Gly Ile Thr Ile
                1090                1095                1100 ttc aaa aac ttc aag gat gca att tat tgg ctt tat aca aaa tta atg        4083
Phe Lys Asn Phe Lys Asp Ala Ile Tyr Trp Leu Tyr Thr Lys Leu Met
            1105                1110                1115 gac ttt tat gaa gtg aat tat ggc aag aag aag gac att tta aat att        4131
Asp Phe Tyr Glu Val Asn Tyr Gly Lys Lys Lys Asp Ile Leu Asn Ile
        1120                1125                1130 ctt aaa gat aac caa caa aaa ata gag aaa gcc att gag gaa gcc gat        4179
Leu Lys Asp Asn Gln Gln Lys Ile Glu Lys Ala Ile Glu Glu Ala Asp
1135                1140                1145                1150
```

-continued

| | |
|---|---|
| aaa ttt tgc att ttg caa atc caa gat gtg gaa aaa tct gaa cag tat<br>Lys Phe Cys Ile Leu Gln Ile Gln Asp Val Glu Lys Ser Glu Gln Tyr<br>                1155                    1160                 1165 | 4227 |
| cag aaa ggg gtt gac ttg ata caa aaa ttg aga act gtt cat tca atg<br>Gln Lys Gly Val Asp Leu Ile Gln Lys Leu Arg Thr Val His Ser Met<br>1170                    1175                    1180 | 4275 |
| gct cag gtt gat cca aat tta atg gtt cat ttg tca cct ttg aga gat<br>Ala Gln Val Asp Pro Asn Leu Met Val His Leu Ser Pro Leu Arg Asp<br>                1185                    1190                 1195 | 4323 |
| tgt ata gca aga gtt cat cag aaa ctt aaa aac ctt gga tct ata aat<br>Cys Ile Ala Arg Val His Gln Lys Leu Lys Asn Leu Gly Ser Ile Asn<br>1200                    1205                    1210 | 4371 |
| cag gca atg gta acg aga tgt gag cca gtt gtt tgt tat tta tat ggc<br>Gln Ala Met Val Thr Arg Cys Glu Pro Val Val Cys Tyr Leu Tyr Gly<br>1215                    1220                    1225                 1230 | 4419 |
| aaa aga ggg gga gga aag agc tta aca tca att gca ttg gca acc aaa<br>Lys Arg Gly Gly Gly Lys Ser Leu Thr Ser Ile Ala Leu Ala Thr Lys<br>                1235                    1240                    1245 | 4467 |
| att tgt aaa cat tat ggt gtt gag cct gaa aag aat atc tat act aaa<br>Ile Cys Lys His Tyr Gly Val Glu Pro Glu Lys Asn Ile Tyr Thr Lys<br>                1250                    1255                    1260 | 4515 |
| cct gtg gct tca gat tac tgg gat gga tat agt gga caa tta att tgc<br>Pro Val Ala Ser Asp Tyr Trp Asp Gly Tyr Ser Gly Gln Leu Ile Cys<br>                1265                    1270                    1275 | 4563 |
| atc att gat gat att ggc caa aac aca aca gat gag gat tgg tca gat<br>Ile Ile Asp Asp Ile Gly Gln Asn Thr Thr Asp Glu Asp Trp Ser Asp<br>1280                    1285                    1290 | 4611 |
| ttt tgt cag tta gtg tca gga tgt cca atg aga tta aac atg gcc tct<br>Phe Cys Gln Leu Val Ser Gly Cys Pro Met Arg Leu Asn Met Ala Ser<br>1295                    1300                    1305                    1310 | 4659 |
| ctt gag gag aag ggt agg cat ttt tct tct cct ttt ata ata gca act<br>Leu Glu Glu Lys Gly Arg His Phe Ser Ser Pro Phe Ile Ile Ala Thr<br>                1315                    1320                    1325 | 4707 |
| tca aat tgg tca aat cca agt cca aaa aca gtt tat gtt aag gaa gca<br>Ser Asn Trp Ser Asn Pro Ser Pro Lys Thr Val Tyr Val Lys Glu Ala<br>                1330                    1335                    1340 | 4755 |
| att gac cgc aga ctc cat ttc aag gtt gaa gtt aaa cct gct tca ttt<br>Ile Asp Arg Arg Leu His Phe Lys Val Glu Val Lys Pro Ala Ser Phe<br>                1345                    1350                    1355 | 4803 |
| ttc aaa aat cct cac aat gat atg ttg aat gtt aat tta gct aaa aca<br>Phe Lys Asn Pro His Asn Asp Met Leu Asn Val Asn Leu Ala Lys Thr<br>1360                    1365                    1370 | 4851 |
| aat gat gca atc aaa gat atg tct tgt gtt gat ttg ata atg gat gga<br>Asn Asp Ala Ile Lys Asp Met Ser Cys Val Asp Leu Ile Met Asp Gly<br>1375                    1380                    1385                    1390 | 4899 |
| cat aat gtt tca ttg atg gat ttg ctc agt tct tta gtc atg aca gtt<br>His Asn Val Ser Leu Met Asp Leu Leu Ser Ser Leu Val Met Thr Val<br>                1395                    1400                    1405 | 4947 |
| gaa att aga aaa caa aac atg act gaa ttc atg gag ttg tgg tct cag<br>Glu Ile Arg Lys Gln Asn Met Thr Glu Phe Met Glu Leu Trp Ser Gln<br>                1410                    1415                    1420 | 4995 |
| gga att tca gat gat gat aat gat agt gca gta gct gag ttt ttc cag<br>Gly Ile Ser Asp Asp Asp Asn Asp Ser Ala Val Ala Glu Phe Phe Gln<br>                1425                    1430                    1435 | 5043 |
| tct ttt cca tct ggt gaa cca tcg aac tct aaa tta tct ggc ttt ttc<br>Ser Phe Pro Ser Gly Glu Pro Ser Asn Ser Lys Leu Ser Gly Phe Phe<br>1440                    1445                    1450 | 5091 |
| caa tct gtt act aat cac aag tgg gtt gct gtg gga gct gca gtt ggc<br>Gln Ser Val Thr Asn His Lys Trp Val Ala Val Gly Ala Ala Val Gly<br>1455                    1460                    1465                    1470 | 5139 |

```
att ctt gga gtg ctc gtt gga gga tgg ttt gtg tat aag cat ttc tcc      5187
Ile Leu Gly Val Leu Val Gly Gly Trp Phe Val Tyr Lys His Phe Ser
            1475                1480                1485 cgc aaa gag gaa gaa cca atc cca gct gaa ggg gta tat tat ggt gta      5235
Arg Lys Glu Glu Glu Pro Ile Pro Ala Glu Gly Val Tyr Tyr Gly Val
        1490                1495                1500 act aag ccc aag caa gtg att aaa tta gat gca gat cca gta gaa tct      5283
Thr Lys Pro Lys Gln Val Ile Lys Leu Asp Ala Asp Pro Val Glu Ser
    1505                1510                1515 cag tca act ttg gaa ata gca gga ctg gtt agg aag aac ttg gtt cag      5331
Gln Ser Thr Leu Glu Ile Ala Gly Leu Val Arg Lys Asn Leu Val Gln
1520                1525                1530 ttt gga gtt gga gag aag aat gga tgt gtg aga tgg gtt atg aat gcc      5379
Phe Gly Val Gly Glu Lys Asn Gly Cys Val Arg Trp Val Met Asn Ala
1535                1540                1545                1550 ttg gga gtg aaa gat gat tgg ctg ctt gtg cct tcc cat gct tat aaa      5427
Leu Gly Val Lys Asp Asp Trp Leu Leu Val Pro Ser His Ala Tyr Lys
            1555                1560                1565 ttt gag aaa gat tat gaa atg atg gag ttt tat ttt aat aga ggt gga      5475
Phe Glu Lys Asp Tyr Glu Met Met Glu Phe Tyr Phe Asn Arg Gly Gly
        1570                1575                1580 act tac tat tca att tca gct ggt aat gtt gtt att caa tct ttg gat      5523
Thr Tyr Tyr Ser Ile Ser Ala Gly Asn Val Val Ile Gln Ser Leu Asp
    1585                1590                1595 gtg gga ttc cag gat gtt gtt ctg atg aag gtt cct aca att cct aag      5571
Val Gly Phe Gln Asp Val Val Leu Met Lys Val Pro Thr Ile Pro Lys
1600                1605                1610 ttt aga gat att act cag cat ttt att aag aaa ggg gat gtg cct aga      5619
Phe Arg Asp Ile Thr Gln His Phe Ile Lys Lys Gly Asp Val Pro Arg
1615                1620                1625                1630 gct ttg aat cgc ctg gca aca tta gtg aca act gta aat gga acc cct      5667
Ala Leu Asn Arg Leu Ala Thr Leu Val Thr Thr Val Asn Gly Thr Pro
            1635                1640                1645 atg tta att tct gag ggc cca cta aag atg gaa gag aaa gct act tat      5715
Met Leu Ile Ser Glu Gly Pro Leu Lys Met Glu Glu Lys Ala Thr Tyr
        1650                1655                1660 gtt cat aag aaa aat gat ggt aca aca gtt gat tta act gtg gat cag      5763
Val His Lys Lys Asn Asp Gly Thr Thr Val Asp Leu Thr Val Asp Gln
    1665                1670                1675 gca tgg aga gga aaa ggc gaa ggt ctt cct gga atg tgt ggt ggg gcc      5811
Ala Trp Arg Gly Lys Gly Glu Gly Leu Pro Gly Met Cys Gly Gly Ala
1680                1685                1690 ttg gtt tca tcg aat caa tct ata cag aat gca atc ttg ggc atc cat      5859
Leu Val Ser Ser Asn Gln Ser Ile Gln Asn Ala Ile Leu Gly Ile His
1695                1700                1705                1710 gtt gct gga gga aat tca att ctt gtt gca aaa ttg gtt act caa gaa      5907
Val Ala Gly Gly Asn Ser Ile Leu Val Ala Lys Leu Val Thr Gln Glu
            1715                1720                1725 atg ttc caa aat att gat aag aaa att gaa agt cag aga att atg aaa      5955
Met Phe Gln Asn Ile Asp Lys Lys Ile Glu Ser Gln Arg Ile Met Lys
        1730                1735                1740 gtg gag ttt act cag tgt tca atg aat gtg gtc tcc aaa acg ctt ttt      6003
Val Glu Phe Thr Gln Cys Ser Met Asn Val Val Ser Lys Thr Leu Phe
    1745                1750                1755 aga aag agt ccc att tat cat cac att gat aaa acc atg att aat ttt      6051
Arg Lys Ser Pro Ile Tyr His His Ile Asp Lys Thr Met Ile Asn Phe
1760                1765                1770 cct gca gct atg ccc ttt tct aaa gct gaa att gat cca atg gct gtg      6099
Pro Ala Ala Met Pro Phe Ser Lys Ala Glu Ile Asp Pro Met Ala Val
```

-continued

```
      1775                1780                1785                1790
atg tta tct aag tat tca tta cct att gta gaa gaa cca gag aat tat          6147
Met Leu Ser Lys Tyr Ser Leu Pro Ile Val Glu Glu Pro Glu Asn Tyr
                1795                1800                1805 aaa gag gct tca att ttt tat caa aat aaa ata gtg ggt aag act cag          6195
Lys Glu Ala Ser Ile Phe Tyr Gln Asn Lys Ile Val Gly Lys Thr Gln
        1810                1815                1820 tta gtt gat gat ttt tta gat ctt gat atg gcc att aca ggg gcc cca          6243
Leu Val Asp Asp Phe Leu Asp Leu Asp Met Ala Ile Thr Gly Ala Pro
    1825                1830                1835 gga att gat gct atc aac atg gat tca tct cct gga ttt cct tat gtc          6291
Gly Ile Asp Ala Ile Asn Met Asp Ser Ser Pro Gly Phe Pro Tyr Val
        1840                1845                1850 cag gag aag ttg acc aaa aga gat tta att tgg ttg gat gaa aat ggt          6339
Gln Glu Lys Leu Thr Lys Arg Asp Leu Ile Trp Leu Asp Glu Asn Gly
1855                1860                1865                1870 tta ttg ctg gga gtt cat cca aga ttg gct cag aga atc tta ttc aat          6387
Leu Leu Leu Gly Val His Pro Arg Leu Ala Gln Arg Ile Leu Phe Asn
                1875                1880                1885 act gtc atg atg gaa aat tgt tct gat ttg gat gtt gtt ttt aca acc          6435
Thr Val Met Met Glu Asn Cys Ser Asp Leu Asp Val Val Phe Thr Thr
        1890                1895                1900 tgt cca aaa gat gaa ttg aga cca tta gag aaa gtg ttg gaa tca aaa          6483
Cys Pro Lys Asp Glu Leu Arg Pro Leu Glu Lys Val Leu Glu Ser Lys
    1905                1910                1915 aca aga gct att gat gct tgt cct ctg gat tac aca att ttg tgc cga          6531
Thr Arg Ala Ile Asp Ala Cys Pro Leu Asp Tyr Thr Ile Leu Cys Arg
        1920                1925                1930 atg tat tgg ggt cca gct att agt tat ttt cat ttg aat cca ggt ttc          6579
Met Tyr Trp Gly Pro Ala Ile Ser Tyr Phe His Leu Asn Pro Gly Phe
1935                1940                1945                1950 cat aca ggt gtt gct att ggc ata gat cct gat aga cag tgg gat gaa          6627
His Thr Gly Val Ala Ile Gly Ile Asp Pro Asp Arg Gln Trp Asp Glu
                1955                1960                1965 tta ttt aaa aca atg ata aga ttc gga gat gtt ggt ctt gat tta gat          6675
Leu Phe Lys Thr Met Ile Arg Phe Gly Asp Val Gly Leu Asp Leu Asp
        1970                1975                1980 ttc tct gct ttt gat gct agt ctt agt cca ttt atg att aga gaa gca          6723
Phe Ser Ala Phe Asp Ala Ser Leu Ser Pro Phe Met Ile Arg Glu Ala
    1985                1990                1995 ggt aga atc atg agt gaa cta tct gga act cca tcc cat ttt ggc aca          6771
Gly Arg Ile Met Ser Glu Leu Ser Gly Thr Pro Ser His Phe Gly Thr
2000                2005                2010 gct ctt atc aat act atc att tat tcc aag cat ttg ctg tat aac tgt          6819
Ala Leu Ile Asn Thr Ile Ile Tyr Ser Lys His Leu Leu Tyr Asn Cys
2015                2020                2025                2030 tgt tac cat gtc tgt ggt tca atg ccc tct ggg tct cct tgt aca gct          6867
Cys Tyr His Val Cys Gly Ser Met Pro Ser Gly Ser Pro Cys Thr Ala
                2035                2040                2045 ttg cta aat tca att att aat aat gtc aat ttg tat tat gtg ttt tcc          6915
Leu Leu Asn Ser Ile Ile Asn Asn Val Asn Leu Tyr Tyr Val Phe Ser
        2050                2055                2060 aag ata ttt gga aag tct cca gtt ttc ttt tgt cag gct ttg aag att          6963
Lys Ile Phe Gly Lys Ser Pro Val Phe Phe Cys Gln Ala Leu Lys Ile
    2065                2070                2075 ctc tgt tat gga gat gat gtt tta ata gtt ttc tct cga gat gtt cag          7011
Leu Cys Tyr Gly Asp Asp Val Leu Ile Val Phe Ser Arg Asp Val Gln
2080                2085                2090 att gat aat ctt gat ctg att gga caa aaa att gta gat gag ttt aag          7059
```

-continued

```
Ile Asp Asn Leu Asp Leu Ile Gly Gln Lys Ile Val Asp Glu Phe Lys
2095                2100                2105                2110 aaa ctt ggc atg aca gct act tct gct gac aag aat gta cct cag ctg     7107
Lys Leu Gly Met Thr Ala Thr Ser Ala Asp Lys Asn Val Pro Gln Leu
                2115                2120                2125 aaa cca gtt tcg gaa ttg act ttt ctc aaa aga tct ttc aat ttg gta     7155
Lys Pro Val Ser Glu Leu Thr Phe Leu Lys Arg Ser Phe Asn Leu Val
2130                2135                2140 gag gat aga att aga cct gca att tcg gaa aaa aca att tgg tct tta     7203
Glu Asp Arg Ile Arg Pro Ala Ile Ser Glu Lys Thr Ile Trp Ser Leu
                2145                2150                2155 ata gca tgg cag aga agt aac gct gag ttt gag cag aat tta gaa aat     7251
Ile Ala Trp Gln Arg Ser Asn Ala Glu Phe Glu Gln Asn Leu Glu Asn
2160                2165                2170 gct cag tgg ttt gct ttt atg cat ggc tat gag ttt tat cag aaa ttt     7299
Ala Gln Trp Phe Ala Phe Met His Gly Tyr Glu Phe Tyr Gln Lys Phe
2175                2180                2185                2190 tat tat ttt gtt cag tcc tgt ttg gag aaa gag atg ata gaa tac aga     7347
Tyr Tyr Phe Val Gln Ser Cys Leu Glu Lys Glu Met Ile Glu Tyr Arg
                2195                2200                2205 ctt aaa tct tat gat tgg tgg aga atg aga ttt tat gac cag tgt ttc     7395
Leu Lys Ser Tyr Asp Trp Trp Arg Met Arg Phe Tyr Asp Gln Cys Phe
                2210                2215                2220 att tgt gac ctt tca tgatttgttt aaacgaattt tcttaaaatt tctgaggttt     7450
Ile Cys Asp Leu Ser
           2225 gtttatttct tttatcagta aataaaaaaa aaaaaaaa                           7488

<210> SEQ ID NO 4
<211> LENGTH: 2227
<212> TYPE: PRT
<213> ORGANISM: Attenuated HAV (Pass 35), strain HM-175

<400> SEQUENCE: 4

Met Asn Met Ser Arg Gln Gly Ile Phe Gln Thr Val Gly Ser Gly Leu
 1               5                  10                  15

Asp His Ile Leu Ser Leu Ala Asp Ile Glu Glu Gln Met Ile Gln
                20                  25                  30

Ser Val Asp Arg Thr Ala Val Thr Gly Ala Ser Tyr Phe Thr Ser Val
            35                  40                  45

Asp Gln Ser Ser Val His Thr Ala Glu Val Gly Ser His Gln Val Glu
        50                  55                  60

Pro Leu Arg Thr Ser Val Asp Lys Pro Gly Ser Lys Arg Thr Gln Gly
 65                  70                  75                  80

Glu Lys Phe Phe Leu Ile His Ser Ala Asp Trp Leu Thr Thr His Ala
                85                  90                  95

Leu Phe His Glu Val Ala Lys Leu Asp Val Val Lys Leu Leu Tyr Asn
            100                 105                 110

Glu Gln Phe Ala Val Gln Gly Leu Leu Arg Tyr His Thr Tyr Ala Arg
        115                 120                 125

Phe Gly Ile Glu Ile Gln Val Gln Ile Asn Pro Thr Pro Phe Gln Gln
    130                 135                 140

Gly Gly Leu Ile Cys Ala Met Val Pro Gly Asp Gln Ser Tyr Gly Ser
145                 150                 155                 160

Ile Ala Ser Leu Thr Val Tyr Pro His Gly Leu Leu Asn Cys Asn Ile
                165                 170                 175

Asn Asn Val Val Arg Ile Lys Val Pro Phe Ile Tyr Thr Arg Gly Ala
```

-continued

```
                180                 185                 190
Tyr His Phe Lys Asp Pro Gln Tyr Pro Val Trp Glu Leu Thr Ile Arg
                195                 200                 205
Val Trp Ser Glu Leu Asn Ile Gly Thr Gly Thr Ser Ala Tyr Thr Ser
210                 215                 220
Leu Asn Val Leu Ala Arg Phe Thr Asp Leu Glu Leu His Gly Leu Thr
225                 230                 235                 240
Pro Leu Ser Thr Gln Met Met Arg Asn Glu Phe Arg Val Ser Thr Thr
                245                 250                 255
Glu Asn Val Val Asn Leu Ser Asn Tyr Glu Asp Ala Arg Ala Lys Met
                260                 265                 270
Ser Phe Ala Leu Asp Gln Glu Asp Trp Lys Ser Asp Pro Ser Gln Gly
                275                 280                 285
Gly Gly Ile Lys Ile Thr His Phe Thr Thr Trp Thr Ser Ile Pro Thr
                290                 295                 300
Leu Ala Ala Gln Phe Pro Phe Asn Ala Ser Asp Ser Val Gly Gln Gln
305                 310                 315                 320
Ile Lys Val Ile Pro Val Asp Pro Tyr Phe Phe Gln Met Thr Asn Thr
                325                 330                 335
Asn Pro Asp Gln Lys Cys Ile Thr Ala Leu Ala Ser Ile Cys Gln Met
                340                 345                 350
Phe Cys Phe Trp Arg Gly Asp Leu Val Phe Asp Phe Gln Val Phe Pro
                355                 360                 365
Thr Lys Tyr His Ser Gly Arg Leu Leu Phe Cys Phe Val Pro Gly Asn
                370                 375                 380
Glu Leu Ile Asp Val Ser Gly Ile Thr Leu Lys Gln Ala Thr Thr Ala
385                 390                 395                 400
Pro Cys Ala Val Met Asp Ile Thr Gly Val Gln Ser Thr Leu Arg Phe
                405                 410                 415
Arg Val Pro Trp Ile Ser Asp Thr Pro Tyr Arg Val Asn Arg Tyr Thr
                420                 425                 430
Lys Ser Ala His Gln Lys Gly Glu Tyr Thr Ala Ile Gly Lys Leu Ile
                435                 440                 445
Val Tyr Cys Tyr Asn Arg Leu Thr Ser Pro Ser Asn Val Ala Ser His
450                 455                 460
Val Arg Val Asn Val Tyr Leu Ser Ala Ile Asn Leu Glu Cys Phe Ala
465                 470                 475                 480
Pro Leu Tyr His Ala Met Asp Val Thr Thr Gln Val Gly Asp Asp Ser
                485                 490                 495
Gly Gly Phe Ser Thr Thr Val Ser Thr Glu Gln Asn Val Pro Asp Pro
                500                 505                 510
Gln Val Gly Ile Thr Thr Met Lys Asp Leu Lys Gly Lys Ala Asn Arg
                515                 520                 525
Gly Lys Met Asp Val Ser Gly Val Gln Ala Pro Val Gly Ala Ile Thr
                530                 535                 540
Thr Ile Glu Asp Pro Val Leu Ala Lys Lys Val Pro Glu Thr Phe Pro
545                 550                 555                 560
Glu Leu Lys Pro Gly Glu Ser Arg His Thr Ser Asp His Met Ser Ile
                565                 570                 575
Tyr Lys Phe Met Gly Arg Ser His Phe Leu Cys Thr Phe Thr Phe Asn
                580                 585                 590
Ser Asn Asn Lys Glu Tyr Thr Phe Pro Ile Thr Leu Ser Ser Thr Ser
                595                 600                 605
```

```
Asn Pro Pro His Gly Leu Pro Ser Thr Leu Arg Trp Phe Phe Asn Leu
    610                 615                 620
Phe Gln Leu Tyr Arg Gly Pro Leu Asp Leu Thr Ile Ile Ile Thr Gly
625                 630                 635                 640
Ala Thr Asp Val Asp Gly Met Ala Trp Phe Thr Pro Val Gly Leu Ala
                645                 650                 655
Val Asp Thr Pro Trp Val Glu Lys Glu Ser Ala Leu Ser Ile Asp Tyr
                660                 665                 670
Lys Thr Ala Leu Gly Ala Val Arg Phe Asn Thr Arg Thr Gly Asn
                675                 680                 685
Ile Gln Ile Arg Leu Pro Trp Tyr Ser Tyr Leu Tyr Ala Val Ser Gly
    690                 695                 700
Ala Leu Asp Gly Leu Gly Asp Lys Thr Asp Ser Thr Phe Gly Leu Val
705                 710                 715                 720
Ser Ile Gln Ile Ala Asn Tyr Asn His Ser Asp Glu Tyr Leu Ser Phe
                725                 730                 735
Ser Cys Tyr Leu Ser Val Thr Glu Gln Ser Glu Phe Tyr Phe Pro Arg
                740                 745                 750
Ala Pro Leu Asn Ser Asn Ala Met Leu Ser Thr Val Ser Met Met Ser
                755                 760                 765
Arg Ile Ala Ala Gly Asp Leu Glu Ser Ser Val Asp Asp Pro Arg Ser
770                 775                 780
Glu Glu Asp Lys Arg Phe Glu Ser His Ile Glu Cys Arg Lys Pro Tyr
785                 790                 795                 800
Lys Glu Leu Arg Leu Glu Val Gly Lys Gln Arg Leu Lys Tyr Ala Gln
                805                 810                 815
Glu Glu Leu Ser Ser Glu Val Leu Pro Pro Arg Lys Met Lys Gly
                820                 825                 830
Leu Phe Ser Gln Ala Lys Ile Ser Leu Phe Tyr Thr Glu His Glu
    835                 840                 845
Ile Met Lys Phe Ser Trp Arg Gly Val Thr Ala Asp Thr Arg Ala Leu
    850                 855                 860
Arg Arg Phe Gly Phe Ser Leu Ala Ala Gly Arg Ser Val Trp Thr Leu
865                 870                 875                 880
Glu Met Asp Ala Gly Val Leu Thr Gly Arg Leu Ile Arg Leu Asn Asp
                885                 890                 895
Glu Lys Trp Thr Glu Met Lys Asp Asp Lys Ile Val Ser Leu Ile Glu
                900                 905                 910
Lys Phe Thr Ser Asn Lys Tyr Trp Ser Lys Val Asn Phe Pro His Gly
                915                 920                 925
Met Leu Asp Leu Glu Glu Ile Ala Ala Asn Ser Lys Asp Phe Pro Asn
    930                 935                 940
Met Ser Glu Thr Asp Leu Cys Phe Leu Leu His Trp Leu Asn Pro Lys
945                 950                 955                 960
Lys Ile Asn Leu Ala Asp Arg Met Leu Gly Leu Ser Gly Val Gln Glu
                965                 970                 975
Ile Lys Glu Gln Gly Val Gly Leu Ile Ala Glu Cys Arg Thr Phe Leu
                980                 985                 990
Asp Ser Ile Ala Gly Thr Leu Lys Ser Met Met Phe Gly Phe His His
                995                 1000                1005
Ser Val Thr Val Glu Ile Ile Asn Thr Val Leu Cys Phe Val Lys Ser
    1010                1015                1020
```

-continued

```
Gly Ile Leu Leu Tyr Val Ile Gln Gln Leu Asn Gln Asp Glu His Ser
1025                1030                1035                1040

His Ile Ile Gly Leu Leu Arg Val Met Asn Tyr Val Asp Ile Gly Cys
            1045                1050                1055

Ser Val Ile Ser Cys Ala Lys Val Phe Ser Lys Met Leu Glu Thr Val
                1060                1065                1070

Phe Asn Trp Gln Met Asp Ser Arg Met Met Glu Leu Arg Thr Gln Ser
        1075                1080                1085

Phe Ser Asn Trp Leu Arg Asp Ile Cys Ser Gly Ile Thr Ile Phe Lys
    1090                1095                1100

Asn Phe Lys Asp Ala Ile Tyr Trp Leu Tyr Thr Lys Leu Met Asp Phe
1105                1110                1115                1120

Tyr Glu Val Asn Tyr Gly Lys Lys Lys Asp Ile Leu Asn Ile Leu Lys
                1125                1130                1135

Asp Asn Gln Gln Lys Ile Glu Lys Ala Ile Glu Glu Ala Asp Lys Phe
            1140                1145                1150

Cys Ile Leu Gln Ile Gln Asp Val Glu Lys Ser Glu Gln Tyr Gln Lys
        1155                1160                1165

Gly Val Asp Leu Ile Gln Lys Leu Arg Thr Val His Ser Met Ala Gln
    1170                1175                1180

Val Asp Pro Asn Leu Met Val His Leu Ser Pro Leu Arg Asp Cys Ile
1185                1190                1195                1200

Ala Arg Val His Gln Lys Leu Lys Asn Leu Gly Ser Ile Asn Gln Ala
                1205                1210                1215

Met Val Thr Arg Cys Glu Pro Val Val Cys Tyr Leu Tyr Gly Lys Arg
            1220                1225                1230

Gly Gly Gly Lys Ser Leu Thr Ser Ile Ala Leu Ala Thr Lys Ile Cys
        1235                1240                1245

Lys His Tyr Gly Val Glu Pro Glu Lys Asn Ile Tyr Thr Lys Pro Val
    1250                1255                1260

Ala Ser Asp Tyr Trp Asp Gly Tyr Ser Gly Gln Leu Ile Cys Ile Ile
1265                1270                1275                1280

Asp Asp Ile Gly Gln Asn Thr Thr Asp Glu Asp Trp Ser Asp Phe Cys
                1285                1290                1295

Gln Leu Val Ser Gly Cys Pro Met Arg Leu Asn Met Ala Ser Leu Glu
            1300                1305                1310

Glu Lys Gly Arg His Phe Ser Ser Pro Phe Ile Ile Ala Thr Ser Asn
        1315                1320                1325

Trp Ser Asn Pro Ser Pro Lys Thr Val Tyr Val Lys Glu Ala Ile Asp
    1330                1335                1340

Arg Arg Leu His Phe Lys Val Glu Val Lys Pro Ala Ser Phe Phe Lys
1345                1350                1355                1360

Asn Pro His Asn Asp Met Leu Asn Val Asn Leu Ala Lys Thr Asn Asp
                1365                1370                1375

Ala Ile Lys Asp Met Ser Cys Val Asp Leu Ile Met Asp Gly His Asn
            1380                1385                1390

Val Ser Leu Met Asp Leu Leu Ser Ser Leu Val Met Thr Val Glu Ile
        1395                1400                1405

Arg Lys Gln Asn Met Thr Glu Phe Met Glu Leu Trp Ser Gln Gly Ile
    1410                1415                1420

Ser Asp Asp Asp Asn Asp Ser Ala Val Ala Glu Phe Phe Gln Ser Phe
1425                1430                1435                1440

Pro Ser Gly Glu Pro Ser Asn Ser Lys Leu Ser Gly Phe Phe Gln Ser
```

-continued

```
              1445                1450                1455
Val Thr Asn His Lys Trp Val Ala Gly Ala Ala Val Gly Ile Leu
            1460                1465                1470
Gly Val Leu Val Gly Gly Trp Phe Val Tyr Lys His Phe Ser Arg Lys
        1475                1480                1485
Glu Glu Glu Pro Ile Pro Ala Glu Gly Val Tyr Tyr Gly Val Thr Lys
        1490                1495                1500
Pro Lys Gln Val Ile Lys Leu Asp Ala Asp Pro Val Glu Ser Gln Ser
1505                1510                1515                1520
Thr Leu Glu Ile Ala Gly Leu Val Arg Lys Asn Leu Val Gln Phe Gly
            1525                1530                1535
Val Gly Glu Lys Asn Gly Cys Val Arg Trp Val Met Asn Ala Leu Gly
            1540                1545                1550
Val Lys Asp Asp Trp Leu Leu Val Pro Ser His Ala Tyr Lys Phe Glu
        1555                1560                1565
Lys Asp Tyr Glu Met Met Glu Phe Tyr Phe Asn Arg Gly Gly Thr Tyr
    1570                1575                1580
Tyr Ser Ile Ser Ala Gly Asn Val Val Ile Gln Ser Leu Asp Val Gly
1585                1590                1595                1600
Phe Gln Asp Val Val Leu Met Lys Val Pro Thr Ile Pro Lys Phe Arg
            1605                1610                1615
Asp Ile Thr Gln His Phe Ile Lys Lys Gly Asp Val Pro Arg Ala Leu
            1620                1625                1630
Asn Arg Leu Ala Thr Leu Val Thr Thr Val Asn Gly Thr Pro Met Leu
        1635                1640                1645
Ile Ser Glu Gly Pro Leu Lys Met Glu Glu Lys Ala Thr Tyr Val His
    1650                1655                1660
Lys Lys Asn Asp Gly Thr Thr Val Asp Leu Thr Val Asp Gln Ala Trp
1665                1670                1675                1680
Arg Gly Lys Gly Glu Gly Leu Pro Gly Met Cys Gly Gly Ala Leu Val
            1685                1690                1695
Ser Ser Asn Gln Ser Ile Gln Asn Ala Ile Leu Gly Ile His Val Ala
        1700                1705                1710
Gly Gly Asn Ser Ile Leu Val Ala Lys Leu Val Thr Gln Glu Met Phe
        1715                1720                1725
Gln Asn Ile Asp Lys Lys Ile Glu Ser Gln Arg Ile Met Lys Val Glu
    1730                1735                1740
Phe Thr Gln Cys Ser Met Asn Val Val Ser Lys Thr Leu Phe Arg Lys
1745                1750                1755                1760
Ser Pro Ile Tyr His His Ile Asp Lys Thr Met Ile Asn Phe Pro Ala
            1765                1770                1775
Ala Met Pro Phe Ser Lys Ala Glu Ile Asp Pro Met Ala Val Met Leu
        1780                1785                1790
Ser Lys Tyr Ser Leu Pro Ile Val Glu Glu Pro Glu Asn Tyr Lys Glu
        1795                1800                1805
Ala Ser Ile Phe Tyr Gln Asn Lys Ile Val Gly Lys Thr Gln Leu Val
        1810                1815                1820
Asp Asp Phe Leu Asp Leu Asp Met Ala Ile Thr Gly Ala Pro Gly Ile
1825                1830                1835                1840
Asp Ala Ile Asn Met Asp Ser Ser Pro Gly Phe Pro Tyr Val Gln Glu
            1845                1850                1855
Lys Leu Thr Lys Arg Asp Leu Ile Trp Leu Asp Glu Asn Gly Leu Leu
        1860                1865                1870
```

```
Leu Gly Val His Pro Arg Leu Ala Gln Arg Ile Leu Phe Asn Thr Val
        1875                1880                1885

Met Met Glu Asn Cys Ser Asp Leu Asp Val Val Phe Thr Thr Cys Pro
        1890                1895                1900

Lys Asp Glu Leu Arg Pro Leu Glu Lys Val Leu Glu Ser Lys Thr Arg
1905                1910                1915                1920

Ala Ile Asp Ala Cys Pro Leu Asp Tyr Thr Ile Leu Cys Arg Met Tyr
                1925                1930                1935

Trp Gly Pro Ala Ile Ser Tyr Phe His Leu Asn Pro Gly Phe His Thr
                1940                1945                1950

Gly Val Ala Ile Gly Ile Asp Pro Asp Arg Gln Trp Asp Glu Leu Phe
                1955                1960                1965

Lys Thr Met Ile Arg Phe Gly Asp Val Gly Leu Asp Leu Asp Phe Ser
        1970                1975                1980

Ala Phe Asp Ala Ser Leu Ser Pro Phe Met Ile Arg Glu Ala Gly Arg
1985                1990                1995                2000

Ile Met Ser Glu Leu Ser Gly Thr Pro Ser His Phe Gly Thr Ala Leu
                2005                2010                2015

Ile Asn Thr Ile Ile Tyr Ser Lys His Leu Leu Tyr Asn Cys Cys Tyr
                2020                2025                2030

His Val Cys Gly Ser Met Pro Ser Gly Ser Pro Cys Thr Ala Leu Leu
                2035                2040                2045

Asn Ser Ile Ile Asn Asn Val Asn Leu Tyr Tyr Val Phe Ser Lys Ile
        2050                2055                2060

Phe Gly Lys Ser Pro Val Phe Phe Cys Gln Ala Leu Lys Ile Leu Cys
2065                2070                2075                2080

Tyr Gly Asp Asp Val Leu Ile Val Phe Ser Arg Asp Val Gln Ile Asp
                2085                2090                2095

Asn Leu Asp Leu Ile Gly Gln Lys Ile Val Asp Glu Phe Lys Lys Leu
                2100                2105                2110

Gly Met Thr Ala Thr Ser Ala Asp Lys Asn Val Pro Gln Leu Lys Pro
                2115                2120                2125

Val Ser Glu Leu Thr Phe Leu Lys Arg Ser Phe Asn Leu Val Glu Asp
        2130                2135                2140

Arg Ile Arg Pro Ala Ile Ser Glu Lys Thr Ile Trp Ser Leu Ile Ala
2145                2150                2155                2160

Trp Gln Arg Ser Asn Ala Glu Phe Glu Gln Asn Leu Glu Asn Ala Gln
                2165                2170                2175

Trp Phe Ala Phe Met His Gly Tyr Glu Phe Tyr Gln Lys Phe Tyr Tyr
                2180                2185                2190

Phe Val Gln Ser Cys Leu Glu Lys Glu Met Ile Glu Tyr Arg Leu Lys
                2195                2200                2205

Ser Tyr Asp Trp Trp Arg Met Arg Phe Tyr Asp Gln Cys Phe Ile Cys
        2210                2215                2220

Asp Leu Ser
2225

<210> SEQ ID NO 5
<211> LENGTH: 7486
<212> TYPE: DNA
<213> ORGANISM: Attenuated HAV (4380), strain HM-175
<220> FEATURE:
<221> NAME/KEY: CDS
<222> LOCATION: (730)..(7410)
```

-continued

```
<400> SEQUENCE: 5
ttcaagaggg gtctccggga atttccggag tccctcttgg aagtccatgg tgaggggact        60
tgatacctca ccgccgtttg cctaggctat aggctaaatt ttcccttcc cttttccctt       120 tcccattccc ttttgcttgt aaatattgat tcctgcaggt tcaggttct taaatctgtt       180 tctctataag aacactcatt ttcacgcttt ctgtcttctt tcttccaggg ctctccctt       240 gccctaggct ctggccgttg cgcccggcgg ggtcaactcc atgattagca tggagctgta       300
ggagtctaaa ttggggacac agatgtttgg aacgtcacct tgcagtgtta acttggcttt       360
catgaatctc tttgatcttc cacaagggt aggctacggg tgaaacctct taggctaata       420
cttctatgaa gagatgcctt ggataggta acagcggcgg atattggtga gttgttaaga       480 caaaaccat tcaacgccgg aggactgact ctcatccagt ggatgcattg agtggattga       540 ctgtcaggc tgtctttagg cttaattcca gacctctctg tgcttgggc aaacatcatt       600 tggccttaaa tgggattctg tgagagggga tccctccatt aacagctgga ctgttctttg       660
gggtcttatg tggtgtttgc cgctgaggta ctcaggggca tttaggtttt tcctcattct       720 taaataata atg aac atg tct aga caa ggt att ttc cag act gtt ggg agt       771
            Met Asn Met Ser Arg Gln Gly Ile Phe Gln Thr Val Gly Ser
            1               5                   10 ggt ctt gac cac atc ctg tct ttg gca gac att gag gaa gag caa atg       819
Gly Leu Asp His Ile Leu Ser Leu Ala Asp Ile Glu Glu Glu Gln Met
15                  20                  25                  30 att caa tca gtt gat agg act gca gtg act ggt gct tct tat ttt act       867
Ile Gln Ser Val Asp Arg Thr Ala Val Thr Gly Ala Ser Tyr Phe Thr
                35                  40                  45 tct gtg gat caa tct tca gtt cat aca gct gag gtt gga tca cac cag       915
Ser Val Asp Gln Ser Ser Val His Thr Ala Glu Val Gly Ser His Gln
            50                  55                  60 gtt gaa cct ttg aga acc tct gtt gat aaa ccc ggt tca aag agg act       963
Val Glu Pro Leu Arg Thr Ser Val Asp Lys Pro Gly Ser Lys Arg Thr
        65                  70                  75 cag gga gag aaa ttt ttc ttg att cat tct gca gat tgg ctt act aca      1011
Gln Gly Glu Lys Phe Phe Leu Ile His Ser Ala Asp Trp Leu Thr Thr
    80                  85                  90 cat gct ctt ttc cat gaa gtt gca aaa ttg gat gtg gtg aaa tta tta      1059
His Ala Leu Phe His Glu Val Ala Lys Leu Asp Val Val Lys Leu Leu
95                  100                 105                 110 tac aat gag cag ttt gct gtt caa ggg ttg ttg aga tac cat aca tat      1107
Tyr Asn Glu Gln Phe Ala Val Gln Gly Leu Leu Arg Tyr His Thr Tyr
                115                 120                 125 gca aga ttt ggc att gaa att caa gtt cag ata aac cct aca cct ttc      1155
Ala Arg Phe Gly Ile Glu Ile Gln Val Gln Ile Asn Pro Thr Pro Phe
            130                 135                 140 caa cag ggg gga ttg atc tgt gct atg gtt cct ggt gac cag agc tat      1203
Gln Gln Gly Gly Leu Ile Cys Ala Met Val Pro Gly Asp Gln Ser Tyr
        145                 150                 155 ggt tct ata gca tca ttg act gtt tat cct cat ggt ttg tta aat tgc      1251
Gly Ser Ile Ala Ser Leu Thr Val Tyr Pro His Gly Leu Leu Asn Cys
    160                 165                 170 aat att aac aat gtg gtt aga ata aag gtt cca ttt att tac aca aga      1299
Asn Ile Asn Asn Val Val Arg Ile Lys Val Pro Phe Ile Tyr Thr Arg
175                 180                 185                 190 ggt gct tac cac ttt aaa gat cca caa tac cca gtt tgg gaa ttg aca      1347
Gly Ala Tyr His Phe Lys Asp Pro Gln Tyr Pro Val Trp Glu Leu Thr
                195                 200                 205 att aga gtt tgg tca gaa tta aat att ggg aca gga act tca gct tat      1395
Ile Arg Val Trp Ser Glu Leu Asn Ile Gly Thr Gly Thr Ser Ala Tyr
```

```
                 Ile Arg Val Trp Ser Glu Leu Asn Ile Gly Thr Gly Thr Ser Ala Tyr
                             210                 215                 220 act tca ctc aat gtt tta gct aga ttt aca gat ttg gag ttg cat gga            1443
Thr Ser Leu Asn Val Leu Ala Arg Phe Thr Asp Leu Glu Leu His Gly
            225                 230                 235 tta act cct ctt tct aca caa atg atg aga aat gaa ttt agg gtc agt            1491
Leu Thr Pro Leu Ser Thr Gln Met Met Arg Asn Glu Phe Arg Val Ser
240                 245                 250 act act gag aat gtg gtg aat ctg tca aat tat gaa gat gca aga gca            1539
Thr Thr Glu Asn Val Val Asn Leu Ser Asn Tyr Glu Asp Ala Arg Ala
255                 260                 265                 270 aag atg tct ttt gct ttg gat cag gaa gat tgg aaa tct gat ccg tcc            1587
Lys Met Ser Phe Ala Leu Asp Gln Glu Asp Trp Lys Ser Asp Pro Ser
                275                 280                 285 cag ggt ggt ggg atc aaa att act cat ttt act act tgg aca tct att            1635
Gln Gly Gly Gly Ile Lys Ile Thr His Phe Thr Thr Trp Thr Ser Ile
            290                 295                 300 cca act ttg gct gct cag ttt cca ttt aat gct tca gac tca gtt ggt            1683
Pro Thr Leu Ala Ala Gln Phe Pro Phe Asn Ala Ser Asp Ser Val Gly
            305                 310                 315 caa caa att aaa gtt att cca gtt gac cca tat ttt ttc caa atg aca            1731
Gln Gln Ile Lys Val Ile Pro Val Asp Pro Tyr Phe Phe Gln Met Thr
        320                 325                 330 aat aca aat cct gac caa aaa tgt ata act gct ttg gct tct att tgt            1779
Asn Thr Asn Pro Asp Gln Lys Cys Ile Thr Ala Leu Ala Ser Ile Cys
335                 340                 345                 350 cag atg ttt tgt ttt tgg aga gga gat ctt gtc ttt gat ttt caa gtt            1827
Gln Met Phe Cys Phe Trp Arg Gly Asp Leu Val Phe Asp Phe Gln Val
                355                 360                 365 ttt ccc acc aaa tat cat tca ggt aga tta ctg ttt tgt ttt gtt cct            1875
Phe Pro Thr Lys Tyr His Ser Gly Arg Leu Leu Phe Cys Phe Val Pro
            370                 375                 380 ggc aat gag cta ata gat gtt tct gga atc aca tta aag caa gca act            1923
Gly Asn Glu Leu Ile Asp Val Ser Gly Ile Thr Leu Lys Gln Ala Thr
            385                 390                 395 act gct cct tgt gca gta atg gat att aca gga gtg cag tca act ttg            1971
Thr Ala Pro Cys Ala Val Met Asp Ile Thr Gly Val Gln Ser Thr Leu
        400                 405                 410 aga ttt cgt gtt ccc tgg att tct gac act cct tac aga gtg aac agg            2019
Arg Phe Arg Val Pro Trp Ile Ser Asp Thr Pro Tyr Arg Val Asn Arg
415                 420                 425                 430 tat aca aag tca gca cat cag aaa ggt gag tac act gcc att ggg aag            2067
Tyr Thr Lys Ser Ala His Gln Lys Gly Glu Tyr Thr Ala Ile Gly Lys
                435                 440                 445 ctt att gtg tat tgt tat aac aga ttg acc tct cct tct aac gtt gct            2115
Leu Ile Val Tyr Cys Tyr Asn Arg Leu Thr Ser Pro Ser Asn Val Ala
            450                 455                 460 tcc cat gtc aga gtg aat gtt tat ctt tca gca att aac ttg gaa tgt            2163
Ser His Val Arg Val Asn Val Tyr Leu Ser Ala Ile Asn Leu Glu Cys
            465                 470                 475 ttt gct cct ctt tat cat gct atg gat gtt act aca caa gtt gga gat            2211
Phe Ala Pro Leu Tyr His Ala Met Asp Val Thr Thr Gln Val Gly Asp
        480                 485                 490 gat tct gga ggt ttt tca aca aca gtt tct aca gaa cag aat gtt cca            2259
Asp Ser Gly Gly Phe Ser Thr Thr Val Ser Thr Glu Gln Asn Val Pro
495                 500                 505                 510 gat ccc caa gtt ggt ata aca acc atg aaa gat ttg aaa gga aaa gct            2307
Asp Pro Gln Val Gly Ile Thr Thr Met Lys Asp Leu Lys Gly Lys Ala
                515                 520                 525
```

-continued

| | |
|---|---|
| aac aga ggg aaa atg gat gtt tca gga gta caa gca cct gtg gga gct<br>Asn Arg Gly Lys Met Asp Val Ser Gly Val Gln Ala Pro Val Gly Ala<br>530                  535                540 | 2355 |
| atc aca aca att gag gat cca gtt tta gca aag aaa gta cct gag aca<br>Ile Thr Thr Ile Glu Asp Pro Val Leu Ala Lys Lys Val Pro Glu Thr<br>545                  550                555 | 2403 |
| ttt cct gaa ttg aaa cct gga gaa tcc aga cat aca tca gat cat atg<br>Phe Pro Glu Leu Lys Pro Gly Glu Ser Arg His Thr Ser Asp His Met<br>560                  565                570 | 2451 |
| tcc atc tac aag ttt atg gga agg tct cat ttc ttg tgc act ttt aca<br>Ser Ile Tyr Lys Phe Met Gly Arg Ser His Phe Leu Cys Thr Phe Thr<br>575                  580                585                590 | 2499 |
| ttc aat tca aat aat aaa gag tac aca ttt cct ata acc ttg tct tca<br>Phe Asn Ser Asn Asn Lys Glu Tyr Thr Phe Pro Ile Thr Leu Ser Ser<br>595                  600                605 | 2547 |
| acc tct aat cct cct cat ggt ttg cca tca aca ctg agg tgg ttt ttc<br>Thr Ser Asn Pro Pro His Gly Leu Pro Ser Thr Leu Arg Trp Phe Phe<br>610                  615                620 | 2595 |
| aac ttg ttt cag ttg tat aga ggg cct tta gat ctg aca att att att<br>Asn Leu Phe Gln Leu Tyr Arg Gly Pro Leu Asp Leu Thr Ile Ile Ile<br>625                  630                635 | 2643 |
| aca gga gca act gat gta gat ggc atg gcc tgg ttc act cca gta ggt<br>Thr Gly Ala Thr Asp Val Asp Gly Met Ala Trp Phe Thr Pro Val Gly<br>640                  645                650 | 2691 |
| ctt gcc gtt gat act cct tgg gta gag aag gag tca gct ttg tct att<br>Leu Ala Val Asp Thr Pro Trp Val Glu Lys Glu Ser Ala Leu Ser Ile<br>655                  660                665                670 | 2739 |
| gac tat aaa act gct ctt gga gct gtc aga ttt aac aca agg aga aca<br>Asp Tyr Lys Thr Ala Leu Gly Ala Val Arg Phe Asn Thr Arg Arg Thr<br>675                  680                685 | 2787 |
| ggg aac att cag att aga tta cca tgg tat tct tat tta tat gct gtg<br>Gly Asn Ile Gln Ile Arg Leu Pro Trp Tyr Ser Tyr Leu Tyr Ala Val<br>690                  695                700 | 2835 |
| tct gga gca ctg gat ggt ttg gga gac aag aca gat tct aca ttt gga<br>Ser Gly Ala Leu Asp Gly Leu Gly Asp Lys Thr Asp Ser Thr Phe Gly<br>705                  710                715 | 2883 |
| ttg gtt tct att cag att gca aat tac aat cat tct gat gaa tac ttg<br>Leu Val Ser Ile Gln Ile Ala Asn Tyr Asn His Ser Asp Glu Tyr Leu<br>720                  725                730 | 2931 |
| tct ttt agt tgt tat ttg tct gtc aca gaa caa tca gag ttt tat ttt<br>Ser Phe Ser Cys Tyr Leu Ser Val Thr Glu Gln Ser Glu Phe Tyr Phe<br>735                  740                745                750 | 2979 |
| ccc aga gct cca ttg aac tca aat gcc atg tta tcc act gta aca atg<br>Pro Arg Ala Pro Leu Asn Ser Asn Ala Met Leu Ser Thr Val Thr Met<br>755                  760                765 | 3027 |
| atg agc aga att gca gct gga gac ttg gag tca tca gtg gat gat cct<br>Met Ser Arg Ile Ala Ala Gly Asp Leu Glu Ser Ser Val Asp Asp Pro<br>770                  775                780 | 3075 |
| aga tca gag gaa gat aaa aga ttt gag agt cat ata gaa tgc agg aag<br>Arg Ser Glu Glu Asp Lys Arg Phe Glu Ser His Ile Glu Cys Arg Lys<br>785                  790                795 | 3123 |
| cca tat aaa gaa ctg aga tta gaa gtt ggg aaa caa aga ctc aag tat<br>Pro Tyr Lys Glu Leu Arg Leu Glu Val Gly Lys Gln Arg Leu Lys Tyr<br>800                  805                810 | 3171 |
| gct cag gaa gaa ttg tca aat gaa gta ctt cca ccc cct agg aaa atg<br>Ala Gln Glu Glu Leu Ser Asn Glu Val Leu Pro Pro Pro Arg Lys Met<br>815                  820                825                830 | 3219 |
| aag gga ctg ttt tca caa gcc aaa att tct ctt ttt tat act gag gag<br>Lys Gly Leu Phe Ser Gln Ala Lys Ile Ser Leu Phe Tyr Thr Glu Glu<br>835                  840                845 | 3267 |

```
cat gaa ata atg aag ttt tcc tgg aga ggt gtg act gct gat act aga      3315
His Glu Ile Met Lys Phe Ser Trp Arg Gly Val Thr Ala Asp Thr Arg
            850                 855                 860 gct tta agg agg ttt gga ttc tct ttg gcc gca ggc aga agt gtg tgg      3363
Ala Leu Arg Arg Phe Gly Phe Ser Leu Ala Ala Gly Arg Ser Val Trp
        865                 870                 875 act ctt gaa atg gat gct ggg gtt ctt act ggg aga ctg att aga ttg      3411
Thr Leu Glu Met Asp Ala Gly Val Leu Thr Gly Arg Leu Ile Arg Leu
    880                 885                 890 aat gat gag aaa tgg aca gaa atg aag gat gac aag att gtt tca ttg      3459
Asn Asp Glu Lys Trp Thr Glu Met Lys Asp Asp Lys Ile Val Ser Leu
895                 900                 905                 910 att gaa aag ttt aca agt aac aaa tat tgg tcc aaa gtg aat ttc cca      3507
Ile Glu Lys Phe Thr Ser Asn Lys Tyr Trp Ser Lys Val Asn Phe Pro
                915                 920                 925 cat ggg atg ttg gat ctt gaa gaa att gct gcc aat tct aag gat ttt      3555
His Gly Met Leu Asp Leu Glu Glu Ile Ala Ala Asn Ser Lys Asp Phe
            930                 935                 940 cct aac atg tct gaa acg gat ttg tgt ttc ttg ctg cat tgg tta aat      3603
Pro Asn Met Ser Glu Thr Asp Leu Cys Phe Leu Leu His Trp Leu Asn
        945                 950                 955 cca aag aaa att aat tta gca gat aga atg ctt gga ttg tct gga gtt      3651
Pro Lys Lys Ile Asn Leu Ala Asp Arg Met Leu Gly Leu Ser Gly Val
    960                 965                 970 cag gaa att aaa gaa caa ggt gtt gga tta ata gca gag tgt aga act      3699
Gln Glu Ile Lys Glu Gln Gly Val Gly Leu Ile Ala Glu Cys Arg Thr
975                 980                 985                 990 ttc tta gat tct att gct gga act tta aaa tct atg atg ttt gga ttt      3747
Phe Leu Asp Ser Ile Ala Gly Thr Leu Lys Ser Met Met Phe Gly Phe
                995                 1000                1005 cat cat tct gtg act gtt gaa att ata aac act gtg ctc tgt ttt gtt      3795
His His Ser Val Thr Val Glu Ile Ile Asn Thr Val Leu Cys Phe Val
            1010                1015                1020 aag agt gga att ttg ctt tat gta ata caa caa ttg aat cag gat gaa      3843
Lys Ser Gly Ile Leu Leu Tyr Val Ile Gln Gln Leu Asn Gln Asp Glu
        1025                1030                1035 cat tct cac ata att ggt ttg ttg aga gtc atg aat tat gta gat att      3891
His Ser His Ile Ile Gly Leu Leu Arg Val Met Asn Tyr Val Asp Ile
    1040                1045                1050 ggt tgt tca gtt att tca tgt gcc aaa gtt ttt tcc aga atg ctg gaa      3939
Gly Cys Ser Val Ile Ser Cys Ala Lys Val Phe Ser Arg Met Leu Glu
1055                1060                1065                1070 aca gtc ttt aat tgg caa atg gac tcc aga atg atg gag tta agg act      3987
Thr Val Phe Asn Trp Gln Met Asp Ser Arg Met Met Glu Leu Arg Thr
                1075                1080                1085 cag agt ttt tcc aac tgg tta aga gat att tgt tct ggg atc acc att      4035
Gln Ser Phe Ser Asn Trp Leu Arg Asp Ile Cys Ser Gly Ile Thr Ile
            1090                1095                1100 ttc aaa aac ttc aag gat gca att tat tgg ctt tat aca aaa tta atg      4083
Phe Lys Asn Phe Lys Asp Ala Ile Tyr Trp Leu Tyr Thr Lys Leu Met
        1105                1110                1115 gac ttt tat gaa gtg aat tat ggc aag aag aag gac att tta aat att      4131
Asp Phe Tyr Glu Val Asn Tyr Gly Lys Lys Lys Asp Ile Leu Asn Ile
    1120                1125                1130 ctt aaa gat aac caa caa aaa ata gag aaa gcc att gag gaa gcc gat      4179
Leu Lys Asp Asn Gln Gln Lys Ile Glu Lys Ala Ile Glu Glu Ala Asp
1135                1140                1145                1150 aaa ttt tgc att ttg caa atc caa gat gtg gaa aaa tct gaa cag tat      4227
Lys Phe Cys Ile Leu Gln Ile Gln Asp Val Glu Lys Ser Glu Gln Tyr
```

-continued

```
        1155                1160                1165
cag aaa ggg gtt gac ttg ata caa aaa ttg aga act gtt cat tca atg      4275
Gln Lys Gly Val Asp Leu Ile Gln Lys Leu Arg Thr Val His Ser Met
            1170                1175                1180 gct cag gtt gat cca aat tta atg gtt cat ttg tca cct ttg aga gat      4323
Ala Gln Val Asp Pro Asn Leu Met Val His Leu Ser Pro Leu Arg Asp
        1185                1190                1195 tgt ata gca aga gtt cat cag aaa ctt aaa aac ctt gga tct ata aat      4371
Cys Ile Ala Arg Val His Gln Lys Leu Lys Asn Leu Gly Ser Ile Asn
    1200                1205                1210 cag gca atg gta acg aga tgt gag cca gtt gtt tgt tat ttt tat ggc      4419
Gln Ala Met Val Thr Arg Cys Glu Pro Val Val Cys Tyr Phe Tyr Gly
1215                1220                1225                1230 aaa aga ggg gga gga aag agc tta aca tca att gca ttg gca acc aaa      4467
Lys Arg Gly Gly Gly Lys Ser Leu Thr Ser Ile Ala Leu Ala Thr Lys
                1235                1240                1245 att tgt aaa cat tat ggt gtt gag cct gaa aag aat atc tat act aaa      4515
Ile Cys Lys His Tyr Gly Val Glu Pro Glu Lys Asn Ile Tyr Thr Lys
            1250                1255                1260 cct gtg gct tca gat tac tgg gat gga tat agt gga caa tta gtt tgc      4563
Pro Val Ala Ser Asp Tyr Trp Asp Gly Tyr Ser Gly Gln Leu Val Cys
        1265                1270                1275 atc att gat gat att ggc caa aac aca aca gat gag gat tgg tca gat      4611
Ile Ile Asp Asp Ile Gly Gln Asn Thr Thr Asp Glu Asp Trp Ser Asp
    1280                1285                1290 ttt tgt cag tta gtg tca gga tgt cct atg aga tta aac atg gcc tct      4659
Phe Cys Gln Leu Val Ser Gly Cys Pro Met Arg Leu Asn Met Ala Ser
1295                1300                1305                1310 ctt gag gag aag ggt agg cat ttt tct tct cct ttt ata ata gca act      4707
Leu Glu Glu Lys Gly Arg His Phe Ser Ser Pro Phe Ile Ile Ala Thr
                1315                1320                1325 tca aat tgg tca aat cca agt cca aaa aca gtt tat gtt aag gaa gca      4755
Ser Asn Trp Ser Asn Pro Ser Pro Lys Thr Val Tyr Val Lys Glu Ala
            1330                1335                1340 att gac cgc aga ctc cat ttc aag gtt gaa gtt aaa cct gct tca ttt      4803
Ile Asp Arg Arg Leu His Phe Lys Val Glu Val Lys Pro Ala Ser Phe
        1345                1350                1355 ttc aaa aat cct cac aat gat atg ttg aat gtt aat tta gct aaa aca      4851
Phe Lys Asn Pro His Asn Asp Met Leu Asn Val Asn Leu Ala Lys Thr
    1360                1365                1370 aat gat gca atc aaa gat atg tct tgt gtt gat ttg ata atg gat gga      4899
Asn Asp Ala Ile Lys Asp Met Ser Cys Val Asp Leu Ile Met Asp Gly
1375                1380                1385                1390 cat aat gtt tca ttg atg gat ttg ctc agt tct tta gtc atg aca gtt      4947
His Asn Val Ser Leu Met Asp Leu Leu Ser Ser Leu Val Met Thr Val
                1395                1400                1405 gaa att aga aaa caa aac atg act gaa ttc atg gag ttg tgg tct cag      4995
Glu Ile Arg Lys Gln Asn Met Thr Glu Phe Met Glu Leu Trp Ser Gln
            1410                1415                1420 gga att tca gat gat gat aat gat agt gca gta gct gag ttt ttc cag      5043
Gly Ile Ser Asp Asp Asp Asn Asp Ser Ala Val Ala Glu Phe Phe Gln
        1425                1430                1435 tct ttt cca tct ggt gaa cca tcg aac tct aaa tta tct ggc ttt ttc      5091
Ser Phe Pro Ser Gly Glu Pro Ser Asn Ser Lys Leu Ser Gly Phe Phe
    1440                1445                1450 caa tct gtt act aat cac aag tgg gtt gct gtg gga gct gca gtt ggc      5139
Gln Ser Val Thr Asn His Lys Trp Val Ala Val Gly Ala Ala Val Gly
1455                1460                1465                1470 gtt ctt gga gtg ctc gtt gga gga tgg ttt gtg tat aag cat ttc tcc      5187
```

-continued

| | | |
|---|---|---|
| Val Leu Gly Val Leu Val Gly Gly Trp Phe Val Tyr Lys His Phe Ser<br>　　　　　　1475　　　　　　　　1480　　　　　　　　1485 | | |
| cgc aaa gag gaa gaa cca atc cca gct gaa ggg gta tat tat ggt gta<br>Arg Lys Glu Glu Glu Pro Ile Pro Ala Glu Gly Val Tyr Tyr Gly Val<br>　　　1490　　　　　　　　1495　　　　　　　　1500 | | 5235 |
| act aag ccc aag caa gtg att aaa tta gat gca gat cca gta gaa tct<br>Thr Lys Pro Lys Gln Val Ile Lys Leu Asp Ala Asp Pro Val Glu Ser<br>1505　　　　　　　　1510　　　　　　　　1515 | | 5283 |
| cag tca act ttg gaa ata gca gga ctg gtt agg aag aac ttg gtt cag<br>Gln Ser Thr Leu Glu Ile Ala Gly Leu Val Arg Lys Asn Leu Val Gln<br>　　　1520　　　　　　　　1525　　　　　　　　1530 | | 5331 |
| ttt gga gtt gga gag aag aat gga tgt gtg aga tgg gtt atg aat gcc<br>Phe Gly Val Gly Glu Lys Asn Gly Cys Val Arg Trp Val Met Asn Ala<br>1535　　　　　　　　1540　　　　　　　　1545　　　　　　　　1550 | | 5379 |
| ttg gga gtg aaa gat gat tgg ctg ctt gtg cct tcc cat gct tat aaa<br>Leu Gly Val Lys Asp Asp Trp Leu Leu Val Pro Ser His Ala Tyr Lys<br>　　　　　　　　1555　　　　　　　　1560　　　　　　　　1565 | | 5427 |
| ttt gag aaa gat tat gaa atg atg gag ttt tat ttt aat aga ggt gga<br>Phe Glu Lys Asp Tyr Glu Met Met Glu Phe Tyr Phe Asn Arg Gly Gly<br>　　　1570　　　　　　　　1575　　　　　　　　1580 | | 5475 |
| act tac tat tca att tca gct ggt aat gtt gtt att caa tct ttg gat<br>Thr Tyr Tyr Ser Ile Ser Ala Gly Asn Val Val Ile Gln Ser Leu Asp<br>1585　　　　　　　　1590　　　　　　　　1595 | | 5523 |
| gtg gga ttc cag gat gtt gtt ctg atg aag gtt cct aca att cct aag<br>Val Gly Phe Gln Asp Val Val Leu Met Lys Val Pro Thr Ile Pro Lys<br>　　　1600　　　　　　　　1605　　　　　　　　1610 | | 5571 |
| ttt aga gat att act cag cat ttt att aag aaa ggg gat gtg cct aga<br>Phe Arg Asp Ile Thr Gln His Phe Ile Lys Lys Gly Asp Val Pro Arg<br>1615　　　　　　　　1620　　　　　　　　1625　　　　　　　　1630 | | 5619 |
| gct ttg aat cgc ctg gca aca tta gtg aca act gta aat gga acc cct<br>Ala Leu Asn Arg Leu Ala Thr Leu Val Thr Thr Val Asn Gly Thr Pro<br>　　　　　　　　1635　　　　　　　　1640　　　　　　　　1645 | | 5667 |
| atg tta att tct gag ggc cca cta aag atg gaa gag aaa gct act tat<br>Met Leu Ile Ser Glu Gly Pro Leu Lys Met Glu Glu Lys Ala Thr Tyr<br>　　　1650　　　　　　　　1655　　　　　　　　1660 | | 5715 |
| gtt cat aag aaa aat gat ggt aca tca gtt gat tta act gtg gat cag<br>Val His Lys Lys Asn Asp Gly Thr Ser Val Asp Leu Thr Val Asp Gln<br>1665　　　　　　　　1670　　　　　　　　1675 | | 5763 |
| gca tgg aga gga aaa ggc gaa ggt ctt cct gga atg tgt ggt ggg gcc<br>Ala Trp Arg Gly Lys Gly Glu Gly Leu Pro Gly Met Cys Gly Gly Ala<br>　　　1680　　　　　　　　1685　　　　　　　　1690 | | 5811 |
| ttg gtt tca tcg aat caa tct ata cag aat gca atc ttg ggc atc cat<br>Leu Val Ser Ser Asn Gln Ser Ile Gln Asn Ala Ile Leu Gly Ile His<br>1695　　　　　　　　1700　　　　　　　　1705　　　　　　　　1710 | | 5859 |
| gtt gct gga gga aat tca att ctt gtt gca aaa ttg gtt act caa gaa<br>Val Ala Gly Gly Asn Ser Ile Leu Val Ala Lys Leu Val Thr Gln Glu<br>　　　　　　　　1715　　　　　　　　1720　　　　　　　　1725 | | 5907 |
| atg ttc caa aat att gat aag aaa att gaa agt cag aga att atg aaa<br>Met Phe Gln Asn Ile Asp Lys Lys Ile Glu Ser Gln Arg Ile Met Lys<br>　　　1730　　　　　　　　1735　　　　　　　　1740 | | 5955 |
| gtg gag ttt act cag tgt tca atg aat gtg gtc tcc aaa acg ctt ttt<br>Val Glu Phe Thr Gln Cys Ser Met Asn Val Val Ser Lys Thr Leu Phe<br>1745　　　　　　　　1750　　　　　　　　1755 | | 6003 |
| aga aag agt ccc att tat cat cac att gat aaa acc atg att aat ttt<br>Arg Lys Ser Pro Ile Tyr His His Ile Asp Lys Thr Met Ile Asn Phe<br>　　　1760　　　　　　　　1765　　　　　　　　1770 | | 6051 |
| cct gca gct atg ccc ttt tct aaa gct gaa att gat cca atg gct gtg<br>Pro Ala Ala Met Pro Phe Ser Lys Ala Glu Ile Asp Pro Met Ala Val<br>1775　　　　　　　　1780　　　　　　　　1785　　　　　　　　1790 | | 6099 |

-continued

| | |
|---|---|
| atg tta tct aag tat tca tta cct att gta gaa gaa cca gag aat tat<br>Met Leu Ser Lys Tyr Ser Leu Pro Ile Val Glu Glu Pro Glu Asn Tyr<br>                1795                      1800                      1805 | 6147 |
| aaa gag gct tca att ttt tat caa aat aaa ata gtg ggt aag act cag<br>Lys Glu Ala Ser Ile Phe Tyr Gln Asn Lys Ile Val Gly Lys Thr Gln<br>            1810                      1815                      1820 | 6195 |
| tta gtt gat gat ttt cta gat ctt gat atg gcc att aca ggg gcc cca<br>Leu Val Asp Asp Phe Leu Asp Leu Asp Met Ala Ile Thr Gly Ala Pro<br>1825                      1830                      1835 | 6243 |
| gga att gat gct atc aac atg gat tca tct cct gga ttt cct tat gtc<br>Gly Ile Asp Ala Ile Asn Met Asp Ser Ser Pro Gly Phe Pro Tyr Val<br>        1840                      1845                      1850 | 6291 |
| cag gag aag ttg acc aaa aga gat tta att tgg ttg gat gaa aat ggt<br>Gln Glu Lys Leu Thr Lys Arg Asp Leu Ile Trp Leu Asp Glu Asn Gly<br>1855                      1860                      1865                      1870 | 6339 |
| tta ttg ctg gga gtt cat cca aga ttg gct cag aga atc tta ttc aat<br>Leu Leu Leu Gly Val His Pro Arg Leu Ala Gln Arg Ile Leu Phe Asn<br>                1875                      1880                      1885 | 6387 |
| act gtc atg atg gaa aat tgt tct gat ttg gat gtt gtt ttt aca acc<br>Thr Val Met Met Glu Asn Cys Ser Asp Leu Asp Val Val Phe Thr Thr<br>            1890                      1895                      1900 | 6435 |
| tgt cca aaa gat gaa ttg aga cca tta gag aaa gtg ttg gaa tca aaa<br>Cys Pro Lys Asp Glu Leu Arg Pro Leu Glu Lys Val Leu Glu Ser Lys<br>        1905                      1910                      1915 | 6483 |
| aca aga gct att gat gct tgt cct ctg gat tac aca att ttg tgc cga<br>Thr Arg Ala Ile Asp Ala Cys Pro Leu Asp Tyr Thr Ile Leu Cys Arg<br>1920                      1925                      1930 | 6531 |
| atg tat tgg ggt cca gct att agt tat ttt cat ttg aat cca ggt ttc<br>Met Tyr Trp Gly Pro Ala Ile Ser Tyr Phe His Leu Asn Pro Gly Phe<br>1935                      1940                      1945                      1950 | 6579 |
| cat aca ggt gtt gct att ggc ata gat cct gat aga cag tgg gat gaa<br>His Thr Gly Val Ala Ile Gly Ile Asp Pro Asp Arg Gln Trp Asp Glu<br>            1955                      1960                      1965 | 6627 |
| tta ttt aaa aca atg ata aga ttc gga gat gtt ggt ctt gat tta gat<br>Leu Phe Lys Thr Met Ile Arg Phe Gly Asp Val Gly Leu Asp Leu Asp<br>        1970                      1975                      1980 | 6675 |
| ttc tct gct ttt gat gct agt ctt agt cca ttt atg att aga gaa gca<br>Phe Ser Ala Phe Asp Ala Ser Leu Ser Pro Phe Met Ile Arg Glu Ala<br>            1985                      1990                      1995 | 6723 |
| ggt aga atc atg agt gaa cta tct gga act cca tcc cat ttt ggc aca<br>Gly Arg Ile Met Ser Glu Leu Ser Gly Thr Pro Ser His Phe Gly Thr<br>        2000                      2005                      2010 | 6771 |
| gct ctt atc aat act atc att tat tcc aag cat ttg ctg tat aac tgt<br>Ala Leu Ile Asn Thr Ile Ile Tyr Ser Lys His Leu Leu Tyr Asn Cys<br>2015                      2020                      2025                      2030 | 6819 |
| tgt tac cat gtc tgt ggt tca atg ccc tct ggg tct cct tgt aca gct<br>Cys Tyr His Val Cys Gly Ser Met Pro Ser Gly Ser Pro Cys Thr Ala<br>            2035                      2040                      2045 | 6867 |
| ttg cta aat tca att att aat aat gtc aat ttg tac tat gtg ttt tcc<br>Leu Leu Asn Ser Ile Ile Asn Asn Val Asn Leu Tyr Tyr Val Phe Ser<br>        2050                      2055                      2060 | 6915 |
| aag ata ttt gga aag tct cca gtt ttc ttt tgt cag gct ttg aag att<br>Lys Ile Phe Gly Lys Ser Pro Val Phe Phe Cys Gln Ala Leu Lys Ile<br>            2065                      2070                      2075 | 6963 |
| ctc tgt tat gga gat gat gtt tta ata gtt ttc tct cga gat gtt cag<br>Leu Cys Tyr Gly Asp Asp Val Leu Ile Val Phe Ser Arg Asp Val Gln<br>        2080                      2085                      2090 | 7011 |
| att gat aat ctt gat ttg att gga caa aaa att gta gat gag ttt aag<br>Ile Asp Asn Leu Asp Leu Ile Gly Gln Lys Ile Val Asp Glu Phe Lys<br>2095                      2100                      2105                      2110 | 7059 |

-continued

| | | |
|---|---|---|
| aaa ctt ggc atg aca gct act tct gct gac aag aat gta cct cag ctg<br>Lys Leu Gly Met Thr Ala Thr Ser Ala Asp Lys Asn Val Pro Gln Leu<br>                              2115                          2120                        2125 | 7107 | aaa cca gtt tcg gaa ttg act ttt ctc aaa aga tct ttc aat ttg gta    7155
Lys Pro Val Ser Glu Leu Thr Phe Leu Lys Arg Ser Phe Asn Leu Val
              2130                     2135                      2140 gag gat aga att aga cct gca att tcg gaa aaa aca att tgg tct tta    7203
Glu Asp Arg Ile Arg Pro Ala Ile Ser Glu Lys Thr Ile Trp Ser Leu
             2145                      2150                    2155 ata gca tgg cag aga agt aac gct gag ttt gag cag aat tta gaa att    7251
Ile Ala Trp Gln Arg Ser Asn Ala Glu Phe Glu Gln Asn Leu Glu Ile
          2160                     2165                    2170 gct cag tgg ttt gct ttt atg cat ggc tat gag ttt tat cag aaa ttt    7299
Ala Gln Trp Phe Ala Phe Met His Gly Tyr Glu Phe Tyr Gln Lys Phe
2175                   2180                     2185                   2190 tat tat ttt gtt cag tcc tgt ttg gag aaa gag atg ata gaa tac aga    7347
Tyr Tyr Phe Val Gln Ser Cys Leu Glu Lys Glu Met Ile Glu Tyr Arg
             2195                    2200                    2205 ctt aaa tct tat gat tgg tgg aga atg aga ttt tat gac cag tgt ttc    7395
Leu Lys Ser Tyr Asp Trp Trp Arg Met Arg Phe Tyr Asp Gln Cys Phe
          2210                     2215                    2220 att tgt gac ctt tca tgatttgttt aaacgaattt tcttaaaatt tctgaggttt    7450
Ile Cys Asp Leu Ser
          2225 gtttatttct tttatcagta aataaaaaaa aaaaaa    7486

<210> SEQ ID NO 6
<211> LENGTH: 2227
<212> TYPE: PRT
<213> ORGANISM: Attenuated (4380) HAV, strain HM-175

<400> SEQUENCE: 6

Met Asn Met Ser Arg Gln Gly Ile Phe Gln Thr Val Gly Ser Gly Leu
  1                  5                  10                 15

Asp His Ile Leu Ser Leu Ala Asp Ile Glu Glu Glu Gln Met Ile Gln
              20                  25                  30

Ser Val Asp Arg Thr Ala Val Thr Gly Ala Ser Tyr Phe Thr Ser Val
          35                   40                  45

Asp Gln Ser Ser Val His Thr Ala Glu Val Gly Ser His Gln Val Glu
    50                  55                  60

Pro Leu Arg Thr Ser Val Asp Lys Pro Gly Ser Lys Arg Thr Gln Gly
65                   70                  75                 80

Glu Lys Phe Phe Leu Ile His Ser Ala Asp Trp Leu Thr Thr His Ala
              85                  90                  95

Leu Phe His Glu Val Ala Lys Leu Asp Val Val Lys Leu Leu Tyr Asn
            100                 105                110

Glu Gln Phe Ala Val Gln Gly Leu Leu Arg Tyr His Thr Tyr Ala Arg
        115                 120                125

Phe Gly Ile Glu Ile Gln Val Gln Ile Asn Pro Thr Pro Phe Gln Gln
    130                 135                140

Gly Gly Leu Ile Cys Ala Met Val Pro Gly Asp Gln Ser Tyr Gly Ser
145               150                155              160

Ile Ala Ser Leu Thr Val Tyr Pro His Gly Leu Leu Asn Cys Asn Ile
            165                 170                175

Asn Asn Val Val Arg Ile Lys Val Pro Phe Ile Tyr Thr Arg Gly Ala
        180                 185                190

-continued

```
Tyr His Phe Lys Asp Pro Gln Tyr Pro Val Trp Glu Leu Thr Ile Arg
            195                 200                 205
Val Trp Ser Glu Leu Asn Ile Gly Thr Gly Thr Ser Ala Tyr Thr Ser
210                 215                 220
Leu Asn Val Leu Ala Arg Phe Thr Asp Leu Glu Leu His Gly Leu Thr
225                 230                 235                 240
Pro Leu Ser Thr Gln Met Met Arg Asn Glu Phe Arg Val Ser Thr Thr
                245                 250                 255
Glu Asn Val Val Asn Leu Ser Asn Tyr Glu Asp Ala Arg Ala Lys Met
            260                 265                 270
Ser Phe Ala Leu Asp Gln Glu Asp Trp Lys Ser Asp Pro Ser Gln Gly
            275                 280                 285
Gly Gly Ile Lys Ile Thr His Phe Thr Thr Trp Thr Ser Ile Pro Thr
290                 295                 300
Leu Ala Ala Gln Phe Pro Phe Asn Ala Ser Asp Ser Val Gly Gln Gln
305                 310                 315                 320
Ile Lys Val Ile Pro Val Asp Pro Tyr Phe Phe Gln Met Thr Asn Thr
                325                 330                 335
Asn Pro Asp Gln Lys Cys Ile Thr Ala Leu Ala Ser Ile Cys Gln Met
            340                 345                 350
Phe Cys Phe Trp Arg Gly Asp Leu Val Phe Asp Phe Gln Val Phe Pro
            355                 360                 365
Thr Lys Tyr His Ser Gly Arg Leu Leu Phe Cys Phe Val Pro Gly Asn
            370                 375                 380
Glu Leu Ile Asp Val Ser Gly Ile Thr Leu Lys Gln Ala Thr Thr Ala
385                 390                 395                 400
Pro Cys Ala Val Met Asp Ile Thr Gly Val Gln Ser Thr Leu Arg Phe
                405                 410                 415
Arg Val Pro Trp Ile Ser Asp Thr Pro Tyr Arg Val Asn Arg Tyr Thr
                420                 425                 430
Lys Ser Ala His Gln Lys Gly Glu Tyr Thr Ala Ile Gly Lys Leu Ile
            435                 440                 445
Val Tyr Cys Tyr Asn Arg Leu Thr Ser Pro Ser Asn Val Ala Ser His
450                 455                 460
Val Arg Val Asn Val Tyr Leu Ser Ala Ile Asn Leu Glu Cys Phe Ala
465                 470                 475                 480
Pro Leu Tyr His Ala Met Asp Val Thr Thr Gln Val Gly Asp Asp Ser
                485                 490                 495
Gly Gly Phe Ser Thr Thr Val Ser Thr Glu Gln Asn Val Pro Asp Pro
            500                 505                 510
Gln Val Gly Ile Thr Thr Met Lys Asp Leu Lys Gly Lys Ala Asn Arg
            515                 520                 525
Gly Lys Met Asp Val Ser Gly Val Gln Ala Pro Val Gly Ala Ile Thr
530                 535                 540
Thr Ile Glu Asp Pro Val Leu Ala Lys Lys Val Pro Glu Thr Phe Pro
545                 550                 555                 560
Glu Leu Lys Pro Gly Glu Ser Arg His Thr Ser Asp His Met Ser Ile
                565                 570                 575
Tyr Lys Phe Met Gly Arg Ser His Phe Leu Cys Thr Phe Thr Phe Asn
                580                 585                 590
Ser Asn Asn Lys Glu Tyr Thr Phe Pro Ile Thr Leu Ser Ser Thr Ser
            595                 600                 605
Asn Pro Pro His Gly Leu Pro Ser Thr Leu Arg Trp Phe Phe Asn Leu
```

-continued

```
            610                 615                 620
Phe Gln Leu Tyr Arg Gly Pro Leu Asp Leu Thr Ile Ile Ile Thr Gly
625                 630                 635                 640
Ala Thr Asp Val Asp Gly Met Ala Trp Phe Thr Pro Val Gly Leu Ala
                645                 650                 655
Val Asp Thr Pro Trp Val Glu Lys Glu Ser Ala Leu Ser Ile Asp Tyr
            660                 665                 670
Lys Thr Ala Leu Gly Ala Val Arg Phe Asn Thr Arg Arg Thr Gly Asn
        675                 680                 685
Ile Gln Ile Arg Leu Pro Trp Tyr Ser Tyr Leu Tyr Ala Val Ser Gly
    690                 695                 700
Ala Leu Asp Gly Leu Gly Asp Lys Thr Asp Ser Thr Phe Gly Leu Val
705                 710                 715                 720
Ser Ile Gln Ile Ala Asn Tyr Asn His Ser Asp Glu Tyr Leu Ser Phe
                725                 730                 735
Ser Cys Tyr Leu Ser Val Thr Glu Gln Ser Glu Phe Tyr Phe Pro Arg
            740                 745                 750
Ala Pro Leu Asn Ser Asn Ala Met Leu Ser Thr Val Thr Met Met Ser
        755                 760                 765
Arg Ile Ala Ala Gly Asp Leu Glu Ser Ser Val Asp Asp Pro Arg Ser
770                 775                 780
Glu Glu Asp Lys Arg Phe Glu Ser His Ile Glu Cys Arg Lys Pro Tyr
785                 790                 795                 800
Lys Glu Leu Arg Leu Glu Val Gly Lys Gln Arg Leu Lys Tyr Ala Gln
                805                 810                 815
Glu Glu Leu Ser Asn Glu Val Leu Pro Pro Arg Lys Met Lys Gly
            820                 825                 830
Leu Phe Ser Gln Ala Lys Ile Ser Leu Phe Tyr Thr Glu Glu His Glu
        835                 840                 845
Ile Met Lys Phe Ser Trp Arg Gly Val Thr Ala Asp Thr Arg Ala Leu
    850                 855                 860
Arg Arg Phe Gly Phe Ser Leu Ala Ala Gly Arg Ser Val Trp Thr Leu
865                 870                 875                 880
Glu Met Asp Ala Gly Val Leu Thr Gly Arg Leu Ile Arg Leu Asn Asp
                885                 890                 895
Glu Lys Trp Thr Glu Met Lys Asp Asp Lys Ile Val Ser Leu Ile Glu
            900                 905                 910
Lys Phe Thr Ser Asn Lys Tyr Trp Ser Lys Val Asn Phe Pro His Gly
        915                 920                 925
Met Leu Asp Leu Glu Glu Ile Ala Ala Asn Ser Lys Asp Phe Pro Asn
    930                 935                 940
Met Ser Glu Thr Asp Leu Cys Phe Leu Leu His Trp Leu Asn Pro Lys
945                 950                 955                 960
Lys Ile Asn Leu Ala Asp Arg Met Leu Gly Leu Ser Gly Val Gln Glu
                965                 970                 975
Ile Lys Glu Gln Gly Val Gly Leu Ile Ala Glu Cys Arg Thr Phe Leu
            980                 985                 990
Asp Ser Ile Ala Gly Thr Leu Lys Ser Met Met Phe Gly Phe His His
        995                 1000                1005
Ser Val Thr Val Glu Ile Ile Asn Thr Val Leu Cys Phe Val Lys Ser
    1010                1015                1020
Gly Ile Leu Leu Tyr Val Ile Gln Gln Leu Asn Gln Asp Glu His Ser
1025                1030                1035                1040
```

```
His Ile Ile Gly Leu Leu Arg Val Met Asn Tyr Val Asp Ile Gly Cys
            1045                1050                1055
Ser Val Ile Ser Cys Ala Lys Val Phe Ser Arg Met Leu Glu Thr Val
            1060                1065                1070
Phe Asn Trp Gln Met Asp Ser Arg Met Met Glu Leu Arg Thr Gln Ser
            1075                1080                1085
Phe Ser Asn Trp Leu Arg Asp Ile Cys Ser Gly Ile Thr Ile Phe Lys
            1090                1095                1100
Asn Phe Lys Asp Ala Ile Tyr Trp Leu Tyr Thr Lys Leu Met Asp Phe
1105                1110                1115                1120
Tyr Glu Val Asn Tyr Gly Lys Lys Lys Asp Ile Leu Asn Ile Leu Lys
            1125                1130                1135
Asp Asn Gln Gln Lys Ile Glu Lys Ala Ile Glu Ala Asp Lys Phe
            1140                1145                1150
Cys Ile Leu Gln Ile Gln Asp Val Glu Lys Ser Glu Gln Tyr Gln Lys
            1155                1160                1165
Gly Val Asp Leu Ile Gln Lys Leu Arg Thr Val His Ser Met Ala Gln
            1170                1175                1180
Val Asp Pro Asn Leu Met Val His Leu Ser Pro Leu Arg Asp Cys Ile
1185                1190                1195                1200
Ala Arg Val His Gln Lys Leu Lys Asn Leu Gly Ser Ile Asn Gln Ala
            1205                1210                1215
Met Val Thr Arg Cys Glu Pro Val Cys Tyr Phe Tyr Gly Lys Arg
            1220                1225                1230
Gly Gly Gly Lys Ser Leu Thr Ser Ile Ala Leu Ala Thr Lys Ile Cys
            1235                1240                1245
Lys His Tyr Gly Val Glu Pro Glu Lys Asn Ile Tyr Thr Lys Pro Val
            1250                1255                1260
Ala Ser Asp Tyr Trp Asp Gly Tyr Ser Gly Gln Leu Val Cys Ile Ile
1265                1270                1275                1280
Asp Asp Ile Gly Gln Asn Thr Thr Asp Glu Asp Trp Ser Asp Phe Cys
            1285                1290                1295
Gln Leu Val Ser Gly Cys Pro Met Arg Leu Asn Met Ala Ser Leu Glu
            1300                1305                1310
Glu Lys Gly Arg His Phe Ser Ser Pro Phe Ile Ile Ala Thr Ser Asn
            1315                1320                1325
Trp Ser Asn Pro Ser Pro Lys Thr Val Tyr Val Lys Glu Ala Ile Asp
            1330                1335                1340
Arg Arg Leu His Phe Lys Val Glu Val Lys Pro Ala Ser Phe Phe Lys
1345                1350                1355                1360
Asn Pro His Asn Asp Met Leu Asn Val Asn Leu Ala Lys Thr Asn Asp
            1365                1370                1375
Ala Ile Lys Asp Met Ser Cys Val Asp Leu Ile Met Asp Gly His Asn
            1380                1385                1390
Val Ser Leu Met Asp Leu Leu Ser Ser Leu Val Met Thr Val Glu Ile
            1395                1400                1405
Arg Lys Gln Asn Met Thr Glu Phe Met Glu Leu Trp Ser Gln Gly Ile
            1410                1415                1420
Ser Asp Asp Asp Asn Asp Ser Ala Val Ala Glu Phe Phe Gln Ser Phe
1425                1430                1435                1440
Pro Ser Gly Glu Pro Ser Asn Ser Lys Leu Ser Gly Phe Phe Gln Ser
            1445                1450                1455
```

-continued

```
Val Thr Asn His Lys Trp Val Ala Val Gly Ala Ala Val Gly Val Leu
            1460                1465                1470

Gly Val Leu Val Gly Gly Trp Phe Val Tyr Lys His Phe Ser Arg Lys
            1475                1480                1485

Glu Glu Glu Pro Ile Pro Ala Glu Gly Val Tyr Tyr Gly Val Thr Lys
            1490                1495                1500

Pro Lys Gln Val Ile Lys Leu Asp Ala Asp Pro Val Glu Ser Gln Ser
1505                1510                1515                1520

Thr Leu Glu Ile Ala Gly Leu Val Arg Lys Asn Leu Val Gln Phe Gly
            1525                1530                1535

Val Gly Glu Lys Asn Gly Cys Val Arg Trp Val Met Asn Ala Leu Gly
            1540                1545                1550

Val Lys Asp Asp Trp Leu Leu Val Pro Ser His Ala Tyr Lys Phe Glu
            1555                1560                1565

Lys Asp Tyr Glu Met Met Glu Phe Tyr Phe Asn Arg Gly Gly Thr Tyr
            1570                1575                1580

Tyr Ser Ile Ser Ala Gly Asn Val Val Ile Gln Ser Leu Asp Val Gly
1585                1590                1595                1600

Phe Gln Asp Val Val Leu Met Lys Val Pro Thr Ile Pro Lys Phe Arg
            1605                1610                1615

Asp Ile Thr Gln His Phe Ile Lys Lys Gly Asp Val Pro Arg Ala Leu
            1620                1625                1630

Asn Arg Leu Ala Thr Leu Val Thr Thr Val Asn Gly Thr Pro Met Leu
            1635                1640                1645

Ile Ser Glu Gly Pro Leu Lys Met Glu Glu Lys Ala Thr Tyr Val His
            1650                1655                1660

Lys Lys Asn Asp Gly Thr Ser Val Asp Leu Thr Val Asp Gln Ala Trp
1665                1670                1675                1680

Arg Gly Lys Gly Glu Gly Leu Pro Gly Met Cys Gly Gly Ala Leu Val
            1685                1690                1695

Ser Ser Asn Gln Ser Ile Gln Asn Ala Ile Leu Gly Ile His Val Ala
            1700                1705                1710

Gly Gly Asn Ser Ile Leu Val Ala Lys Leu Val Thr Gln Glu Met Phe
            1715                1720                1725

Gln Asn Ile Asp Lys Lys Ile Glu Ser Gln Arg Ile Met Lys Val Glu
            1730                1735                1740

Phe Thr Gln Cys Ser Met Asn Val Val Ser Lys Thr Leu Phe Arg Lys
1745                1750                1755                1760

Ser Pro Ile Tyr His His Ile Asp Lys Thr Met Ile Asn Phe Pro Ala
            1765                1770                1775

Ala Met Pro Phe Ser Lys Ala Glu Ile Asp Pro Met Ala Val Met Leu
            1780                1785                1790

Ser Lys Tyr Ser Leu Pro Ile Val Glu Glu Pro Glu Asn Tyr Lys Glu
            1795                1800                1805

Ala Ser Ile Phe Tyr Gln Asn Lys Ile Val Gly Lys Thr Gln Leu Val
            1810                1815                1820

Asp Asp Phe Leu Asp Leu Asp Met Ala Ile Thr Gly Ala Pro Gly Ile
1825                1830                1835                1840

Asp Ala Ile Asn Met Asp Ser Ser Pro Gly Phe Pro Tyr Val Gln Glu
            1845                1850                1855

Lys Leu Thr Lys Arg Asp Leu Ile Trp Leu Asp Glu Asn Gly Leu Leu
            1860                1865                1870

Leu Gly Val His Pro Arg Leu Ala Gln Arg Ile Leu Phe Asn Thr Val
```

―continued

```
                1875              1880               1885
Met Met Glu Asn Cys Ser Asp Leu Asp Val Val Phe Thr Thr Cys Pro
    1890              1895               1900

Lys Asp Glu Leu Arg Pro Leu Glu Lys Val Leu Glu Ser Lys Thr Arg
1905              1910              1915              1920

Ala Ile Asp Ala Cys Pro Leu Asp Tyr Thr Ile Leu Cys Arg Met Tyr
            1925              1930              1935

Trp Gly Pro Ala Ile Ser Tyr Phe His Leu Asn Pro Gly Phe His Thr
            1940              1945              1950

Gly Val Ala Ile Gly Ile Asp Pro Asp Arg Gln Trp Asp Glu Leu Phe
            1955              1960              1965

Lys Thr Met Ile Arg Phe Gly Asp Val Gly Leu Asp Leu Asp Phe Ser
    1970              1975              1980

Ala Phe Asp Ala Ser Leu Ser Pro Phe Met Ile Arg Glu Ala Gly Arg
1985              1990              1995              2000

Ile Met Ser Glu Leu Ser Gly Thr Pro Ser His Phe Gly Thr Ala Leu
                2005              2010              2015

Ile Asn Thr Ile Ile Tyr Ser Lys His Leu Leu Tyr Asn Cys Cys Tyr
            2020              2025              2030

His Val Cys Gly Ser Met Pro Ser Gly Ser Pro Cys Thr Ala Leu Leu
            2035              2040              2045

Asn Ser Ile Ile Asn Asn Val Asn Leu Tyr Tyr Val Phe Ser Lys Ile
    2050              2055              2060

Phe Gly Lys Ser Pro Val Phe Phe Cys Gln Ala Leu Lys Ile Leu Cys
2065              2070              2075              2080

Tyr Gly Asp Asp Val Leu Ile Val Phe Ser Arg Asp Val Gln Ile Asp
            2085              2090              2095

Asn Leu Asp Leu Ile Gly Gln Lys Ile Val Asp Glu Phe Lys Lys Leu
            2100              2105              2110

Gly Met Thr Ala Thr Ser Ala Asp Lys Asn Val Pro Gln Leu Lys Pro
            2115              2120              2125

Val Ser Glu Leu Thr Phe Leu Lys Arg Ser Phe Asn Leu Val Glu Asp
    2130              2135              2140

Arg Ile Arg Pro Ala Ile Ser Glu Lys Thr Ile Trp Ser Leu Ile Ala
2145              2150              2155              2160

Trp Gln Arg Ser Asn Ala Glu Phe Glu Gln Asn Leu Glu Ile Ala Gln
            2165              2170              2175

Trp Phe Ala Phe Met His Gly Tyr Glu Phe Tyr Gln Lys Phe Tyr Tyr
            2180              2185              2190

Phe Val Gln Ser Cys Leu Glu Lys Glu Met Ile Glu Tyr Arg Leu Lys
            2195              2200              2205

Ser Tyr Asp Trp Trp Arg Met Arg Phe Tyr Asp Gln Cys Phe Ile Cys
    2210              2215              2220

Asp Leu Ser
2225
```